United States Patent
Duggal et al.

(10) Patent No.: US 10,786,362 B2
(45) Date of Patent: Sep. 29, 2020

(54) SYSTEMS AND METHODS FOR VERTEBRAL DISC REPLACEMENT

(71) Applicant: Synergy Disc Replacement, Inc., Kitchener (CA)

(72) Inventors: Neil Duggal, London (CA); Dylan Matthew Hushka, Niwot, CO (US); Joshua A. Butters, Chandler, AZ (US); Jeffery D. Arnett, Gilbert, AZ (US)

(73) Assignee: SYNERGY DISC REPLACEMENT, INC., Ontario (CA)

( * ) Notice: Subject to any disclaimer, the term of this patent is extended or adjusted under 35 U.S.C. 154(b) by 191 days.

(21) Appl. No.: 16/051,483

(22) Filed: Aug. 1, 2018

(65) Prior Publication Data
US 2018/0368988 A1    Dec. 27, 2018

Related U.S. Application Data

(63) Continuation of application No. 14/505,972, filed on Oct. 3, 2014, now Pat. No. 10,064,739, which is a
(Continued)

(51) Int. Cl.
*A61F 2/46*    (2006.01)
*A61F 2/44*    (2006.01)
(Continued)

(52) U.S. Cl.
CPC ........ *A61F 2/4425* (2013.01); *A61B 17/1604* (2013.01); *A61B 17/1671* (2013.01);
(Continued)

(58) Field of Classification Search
CPC .................. A61F 2002/443; A61F 2/4611
See application file for complete search history.

(56) References Cited

U.S. PATENT DOCUMENTS

| | | | |
|---|---|---|---|
| 3,798,679 A | 3/1974 | Ewald |
| 3,867,728 A | 2/1975 | Stubstad |
| (Continued) | | | |

FOREIGN PATENT DOCUMENTS

| | | |
|---|---|---|
| AU | 2005260554 | 10/2010 |
| AU | 2008316600 | 9/2014 |
| (Continued) | | |

*Primary Examiner* — Samuel S Hanna
(74) *Attorney, Agent, or Firm* — Maywood IP Law; G. Jo Hays; David W. Meibos

(57) ABSTRACT

The present invention provides artificial disc prostheses, methods and instrumentation for implantation and revision thereof. Each prosthesis may comprise superior and inferior end plates and a nucleus positioned between articular surfaces of the end plates. The end plates may have planar bone engagement surfaces with a plurality of self-cutting teeth. The articular surfaces of the end plates may be planar or include a flattened portion. The nucleus includes superior and inferior articular surfaces which may comprise flattened portions such that when the articular surfaces of the nucleus and the end plates are placed in cooperation in a preferred orientation, the flattened and/or planar portions are aligned. Each prosthesis may provide flexion/extension, anterior/posterior translation, lateral bending, and/or axial rotation degrees of freedom. One embodiment comprises a prosthesis with a first joint providing flexion/extension and anterior/posterior translation, and a second joint providing lateral bending and axial rotation.

18 Claims, 44 Drawing Sheets

Related U.S. Application Data continuation of application No. 12/323,068, filed on Nov. 25, 2008, now Pat. No. 8,852,193, which is a continuation-in-part of application No. 12/258,961, filed on Oct. 27, 2008, now Pat. No. 8,894,709, which is a continuation-in-part of application No. 12/041,910, filed on Mar. 4, 2008, now Pat. No. 9,237,958, which is a continuation-in-part of application No. 11/559,215, filed on Nov. 13, 2006, now Pat. No. 7,927,374, which is a continuation-in-part of application No. 11/534,014, filed on Sep. 21, 2006, now Pat. No. 8,172,904, which is a continuation-in-part of application No. 10/590,139, filed as application No. PCT/US2005/023134 on Jun. 30, 2005, now Pat. No. 8,100,974, and a continuation-in-part of application No. 12/258,977, filed on Oct. 27, 2008, now Pat. No. 8,454,699.

(60) Provisional application No. 60/658,161, filed on Mar. 4, 2005, provisional application No. 60/584,240, filed on Jun. 30, 2004, provisional application No. 60/982,627, filed on Oct. 25, 2007, provisional application No. 60/983,500, filed on Oct. 29, 2007, provisional application No. 61/023,019, filed on Jan. 23, 2008, provisional application No. 61/041,086, filed on Mar. 31, 2008, provisional application No. 61/050,531, filed on May 5, 2008, provisional application No. 61/074,498, filed on Jun. 20, 2008.

(51) Int. Cl.
*A61B 17/16* (2006.01)
*A61B 17/17* (2006.01)
*A61F 2/32* (2006.01)
*A61B 17/70* (2006.01)
*A61B 17/02* (2006.01)
*A61F 2/30* (2006.01)

(52) U.S. Cl.
CPC ...... *A61B 17/1757* (2013.01); *A61B 17/7079* (2013.01); *A61F 2/32* (2013.01); *A61F 2/4657* (2013.01); *A61F 2/4684* (2013.01); *A61B 2017/0256* (2013.01); *A61F 2/4611* (2013.01); *A61F 2002/302* (2013.01); *A61F 2002/305* (2013.01); *A61F 2002/3039* (2013.01); *A61F 2002/3065* (2013.01); *A61F 2002/3069* (2013.01); *A61F 2002/30232* (2013.01); *A61F 2002/30242* (2013.01); *A61F 2002/30354* (2013.01); *A61F 2002/30364* (2013.01); *A61F 2002/30369* (2013.01); *A61F 2002/30383* (2013.01); *A61F 2002/30397* (2013.01); *A61F 2002/30426* (2013.01); *A61F 2002/30528* (2013.01); *A61F 2002/30538* (2013.01); *A61F 2002/30563* (2013.01); *A61F 2002/30578* (2013.01); *A61F 2002/30604* (2013.01); *A61F 2002/30616* (2013.01); *A61F 2002/30652* (2013.01); *A61F 2002/30654* (2013.01); *A61F 2002/30655* (2013.01); *A61F 2002/30662* (2013.01); *A61F 2002/30663* (2013.01); *A61F 2002/30685* (2013.01); *A61F 2002/30841* (2013.01); *A61F 2002/30843* (2013.01); *A61F 2002/30884* (2013.01); *A61F 2002/30892* (2013.01); *A61F 2002/30904* (2013.01); *A61F 2002/30934* (2013.01); *A61F 2002/30937* (2013.01); *A61F 2002/443* (2013.01); *A61F 2002/4658* (2013.01); *A61F 2002/4687* (2013.01); *A61F 2220/0025* (2013.01); *A61F 2220/0033* (2013.01); *A61F 2230/0065* (2013.01); *A61F 2230/0069* (2013.01); *A61F 2230/0071* (2013.01); *A61F 2250/0006* (2013.01); *A61F 2310/00017* (2013.01); *A61F 2310/00023* (2013.01); *A61F 2310/00029* (2013.01); *A61F 2310/00179* (2013.01); *A61F 2310/00407* (2013.01); *A61F 2310/00796* (2013.01)

(56) References Cited

U.S. PATENT DOCUMENTS

| | | |
|---|---|---|
| 3,875,595 A | 4/1975 | Froning |
| 4,007,495 A | 2/1977 | Frazier |
| 4,021,864 A | 5/1977 | Waugh |
| 4,069,518 A | 1/1978 | Groth, Jr. |
| 4,232,404 A | 11/1980 | Samuelson |
| 4,309,777 A | 1/1982 | Patil |
| 4,714,469 A | 12/1987 | Kenna |
| 4,863,476 A | 9/1989 | Shepperd |
| 4,863,477 A | 9/1989 | Monson |
| 4,874,389 A | 10/1989 | Downey |
| 4,911,718 A | 3/1990 | Lee |
| 4,946,378 A | 8/1990 | Hirayama |
| 4,997,432 A | 3/1991 | Keller |
| 5,002,576 A | 3/1991 | Fuhrmann |
| 5,071,437 A | 12/1991 | Steffee |
| 5,123,926 A | 6/1992 | Pisharodi |
| 5,258,031 A | 11/1993 | Salib |
| 5,306,308 A | 4/1994 | Gross |
| 5,314,477 A | 5/1994 | Marnay |
| 5,326,365 A | 5/1994 | Alvine |
| 5,320,644 A | 6/1994 | Baumgartner |
| 5,350,644 A | 9/1994 | Graetzel |
| 5,370,697 A | 12/1994 | Baumgartner |
| 5,401,269 A | 3/1995 | Buttner-Janz |
| 5,425,773 A | 6/1995 | Boyd |
| 5,458,642 A | 10/1995 | Beer |
| 5,507,816 A | 4/1996 | Bullivant |
| 5,534,029 A | 7/1996 | Shima |
| 5,534,030 A | 7/1996 | Navarro |
| 5,556,431 A | 9/1996 | Buttner-Janz |
| 5,645,596 A | 7/1997 | Kim |
| 5,674,294 A | 10/1997 | Bainville |
| 5,676,701 A | 10/1997 | Yuan |
| 5,676,702 A | 10/1997 | Ratron |
| 5,683,464 A | 11/1997 | Wagner |
| 5,683,465 A | 11/1997 | Shinn |
| 5,702,450 A | 12/1997 | Bisserie |
| 5,755,796 A | 5/1998 | Ibo |
| 5,824,094 A | 10/1998 | Serhan |
| 5,827,328 A | 10/1998 | Buttermann |
| 5,865,846 A | 2/1999 | Bryan |
| 5,888,226 A | 3/1999 | Rogozinski |
| 5,893,889 A | 4/1999 | Harrington |
| 5,895,428 A | 4/1999 | Berry |
| 5,898,428 A | 4/1999 | Zimlich |
| 5,899,941 A | 5/1999 | Nishijima |
| 5,919,235 A | 7/1999 | Husson |
| 5,928,284 A | 7/1999 | Mehdizadeh |
| 5,935,173 A | 8/1999 | Roger |
| 5,989,291 A | 11/1999 | Ralph |
| 6,001,130 A | 12/1999 | Bryan |
| 6,019,792 A | 2/2000 | Cauthen |
| 6,039,763 A | 3/2000 | Shelokov |
| 6,051,751 A | 4/2000 | Sioshansi |
| 6,063,121 A | 5/2000 | Xavier |
| 6,066,174 A | 5/2000 | Farris |
| 6,113,637 A | 9/2000 | Gill |
| 6,136,031 A | 10/2000 | Middleton |
| 6,146,421 A | 11/2000 | Gordon |
| 6,146,422 A | 11/2000 | Lawson |
| 6,179,874 B1 | 1/2001 | Cauthen |
| 6,368,350 B1 | 4/2002 | Erickson |
| 6,375,682 B1 | 4/2002 | Fleischmann |
| 6,375,683 B1 | 4/2002 | Corzet |
| 6,402,785 B1 | 6/2002 | Zdeblick |

(56) References Cited

U.S. PATENT DOCUMENTS

| | | |
|---|---|---|
| 6,416,551 B1 | 7/2002 | Keller |
| 6,468,310 B1 | 10/2002 | Ralph |
| 6,478,800 B1 | 11/2002 | Fraser |
| 6,517,580 B1 | 2/2003 | Ramadan |
| 6,520,996 B1 | 2/2003 | Manasas |
| 6,527,804 B1 | 3/2003 | Gauchet |
| 6,562,045 B2 | 5/2003 | Gil |
| 6,579,320 B1 | 6/2003 | Gauchet |
| 6,579,321 B1 | 6/2003 | Gordon |
| 6,592,624 B1 | 7/2003 | Fraser |
| 6,599,320 B1 | 7/2003 | Kuslich |
| 6,610,093 B1 | 8/2003 | Pisharodi |
| 6,626,943 B2 | 9/2003 | Eberlein |
| 6,652,533 B2 | 11/2003 | O'Neil |
| 6,669,730 B2 | 12/2003 | Ralph |
| 6,682,562 B2 | 1/2004 | Viart |
| 6,706,068 B2 | 3/2004 | Ferree |
| 6,709,439 B2 | 3/2004 | Rogers |
| 6,726,720 B2 | 4/2004 | Ross |
| 6,740,118 B2 | 5/2004 | Eisermann |
| 6,749,635 B1 | 6/2004 | Bryan |
| 6,761,723 B2 | 7/2004 | Buttermann |
| 6,770,094 B2 | 8/2004 | Fehling |
| 6,770,095 B2 | 8/2004 | Grinberg |
| 6,793,678 B2 | 9/2004 | Hawkins |
| 6,881,228 B2 | 4/2005 | Zdeblick |
| 6,899,735 B2 | 5/2005 | Coates |
| 6,908,484 B2 | 6/2005 | Zubok |
| 6,936,071 B1 | 8/2005 | Marnay |
| 6,949,105 B2 | 9/2005 | Bryan |
| 6,960,232 B2 | 11/2005 | Lyons |
| 6,964,686 B2 | 11/2005 | Gordon |
| 6,966,929 B2 | 11/2005 | Mitchell |
| 6,976,988 B2 | 12/2005 | Ralph |
| 6,986,789 B2 | 1/2006 | Schultz |
| 6,989,032 B2 | 1/2006 | Errico |
| 6,994,727 B2 | 2/2006 | Khandkar |
| 7,001,432 B2 | 2/2006 | Keller |
| 7,001,433 B2 | 2/2006 | Songer |
| 7,025,787 B2 | 4/2006 | Bryan |
| 7,048,764 B2 | 5/2006 | Ferree |
| 7,048,766 B2 | 5/2006 | Ferree |
| 7,056,344 B2 | 6/2006 | Huppert |
| 7,060,097 B2 | 6/2006 | Fraser |
| 7,060,099 B2 | 6/2006 | Carli |
| 7,066,961 B2 | 6/2006 | Michelson |
| 7,101,400 B2 | 9/2006 | Thramann |
| 7,105,024 B2 | 9/2006 | Richelsoph |
| 7,118,580 B1 | 10/2006 | Beyersdorff |
| 7,147,665 B1 | 12/2006 | Bryan |
| 7,153,325 B2 | 12/2006 | Kim |
| 7,156,848 B2 | 1/2007 | Ferree |
| 7,156,876 B2 | 1/2007 | Moumene |
| 7,166,131 B2 | 1/2007 | Studer |
| 7,179,294 B2 | 2/2007 | Eisermann |
| 7,201,776 B2 | 4/2007 | Ferree |
| 7,204,852 B2 | 4/2007 | Marnay |
| 7,217,291 B2 | 5/2007 | Zucherman |
| 7,226,452 B2 | 6/2007 | Zubok |
| 7,235,101 B2 | 6/2007 | Berry |
| 7,244,275 B2 | 7/2007 | Michelson |
| 7,250,060 B2 | 7/2007 | Trieu |
| 7,255,714 B2 | 8/2007 | Malek |
| 7,267,691 B2 | 9/2007 | Keller |
| 7,276,082 B2 | 10/2007 | Zdeblick |
| 7,291,171 B2 | 11/2007 | Ferree |
| 7,325,260 B1 | 2/2008 | Hoyt |
| 7,364,589 B2 | 4/2008 | Eisermann |
| 7,727,279 B2 | 6/2010 | Zipnick |
| 7,927,373 B2 | 4/2011 | Parsons |
| 7,927,374 B2 | 4/2011 | Duggal |
| 7,959,678 B2 | 6/2011 | Filippi |
| 8,038,716 B2 | 10/2011 | Duggal |
| 8,100,974 B2 | 1/2012 | Duggal |
| 8,114,092 B2 | 2/2012 | Altarac |
| 8,133,282 B2 | 3/2012 | Hushka |
| 8,172,904 B2 | 5/2012 | Duggal |
| 8,231,677 B2 | 7/2012 | Duggal |
| 8,454,699 B2 | 6/2013 | Duggal |
| 8,852,193 B2 | 10/2014 | Hushka |
| 8,894,709 B2 | 11/2014 | Duggal |
| 9,125,754 B2 | 9/2015 | Duggal |
| 9,237,958 B2 | 1/2016 | Duggal |
| 2002/0035400 A1 | 3/2002 | Bryan |
| 2003/0120347 A1 | 6/2003 | Steinberg |
| 2003/0135277 A1 | 7/2003 | Bryan |
| 2003/0181985 A1 | 9/2003 | Keller |
| 2004/0002761 A1 | 1/2004 | Rogers |
| 2004/0122523 A1 | 6/2004 | Guzman |
| 2004/0133282 A1 | 7/2004 | Deffenbaugh |
| 2004/0153157 A1 | 8/2004 | Keller |
| 2004/0158328 A1 | 8/2004 | Eisermann |
| 2004/0193282 A1 | 9/2004 | Hanes |
| 2004/0243240 A1 | 12/2004 | Beaurain |
| 2005/0015152 A1 | 1/2005 | Sweeney |
| 2005/0033305 A1 | 2/2005 | Schultz |
| 2005/0101991 A1 | 5/2005 | Ahlberg |
| 2005/0113926 A1 | 5/2005 | Zucherman |
| 2005/0125065 A1 | 6/2005 | Zucherman |
| 2005/0149053 A1 | 7/2005 | Varieur |
| 2005/0159818 A1 | 7/2005 | Blain |
| 2005/0216086 A1 | 9/2005 | Marik |
| 2005/0273173 A1 | 12/2005 | Gordon |
| 2005/0283248 A1 | 12/2005 | Gordon |
| 2006/0030862 A1 | 2/2006 | De Villiers |
| 2006/0052872 A1 | 3/2006 | Studer |
| 2006/0116768 A1 | 6/2006 | Krueger |
| 2006/0122703 A1 | 6/2006 | Aebi |
| 2006/0136061 A1 | 6/2006 | Navarro |
| 2006/0155377 A1 | 7/2006 | Beaurain et al. |
| 2007/0073311 A1* | 3/2007 | Williams ............... A61F 2/4455 606/108 |
| 2007/0198093 A1 | 8/2007 | Brodke |
| 2007/0225812 A1 | 9/2007 | Gill |
| 2008/0033563 A1 | 2/2008 | Khandhar et al. |
| 2008/0319548 A1 | 12/2008 | Kuras |
| 2009/0082867 A1 | 3/2009 | Sebastian Bueno |
| 2009/0204219 A1 | 8/2009 | Beaurain et al. |
| 2009/0216330 A1 | 8/2009 | Geisert |
| 2010/0217395 A1 | 8/2010 | Bertagnoli |
| 2011/0320003 A1 | 12/2011 | Duggal |
| 2013/0204369 A1 | 8/2013 | Duggal |

FOREIGN PATENT DOCUMENTS

| | | |
|---|---|---|
| BR | 200512736 | 4/2008 |
| CA | 2570192 | 8/2011 |
| CA | 2730842 | 2/2014 |
| CA | 2712060 | 8/2016 |
| CA | 2703237 | 10/2016 |
| CN | 101980671 | 2/2011 |
| CN | 101022770 | 2/2012 |
| CN | 101909549 | 7/2014 |
| EP | 0042271 A1 | 12/1981 |
| EP | 176728 A1 | 4/1986 |
| EP | 0282161 A1 | 9/1988 |
| EP | 0298233 A1 | 1/1989 |
| EP | 2327376 | 10/2012 |
| EP | 2285310 | 1/2014 |
| EP | 2211785 | 1/2016 |
| EP | 2641571 | 4/2016 |
| FR | 2730159 | 8/1996 |
| FR | 2805985 | 9/2001 |
| FR | 2814059 | 11/2002 |
| FR | 2893838 | 11/2005 |
| IN | 276579 | 10/2016 |
| JP | 2011514193 | 5/2011 |
| JP | 04917027 | 4/2012 |
| KR | 1169110 | 7/2012 |
| RU | 2080841 | 6/1997 |
| RU | 2401086 | 10/2010 |
| WO | WO09526697 | 10/1995 |
| WO | WO2000042944 | 7/2000 |
| WO | WO2004041131 | 5/2004 |

(56) References Cited

FOREIGN PATENT DOCUMENTS

| WO | WO2004064692 | 8/2004 |
| WO | WO2004089259 | 10/2004 |
| WO | WO2005039455 | 5/2005 |
| WO | WO2005046534 | 5/2005 |
| WO | WO2005053580 | 6/2005 |
| WO | WO2005094737 | 10/2005 |
| WO | WO2006004848 | 1/2006 |
| WO | WO2006042870 | 4/2006 |
| WO | WO2006116852 | 11/2006 |
| WO | WO2007041375 | 4/2007 |
| WO | WO2007063398 | 6/2007 |
| WO | WO2008036502 | 3/2008 |
| WO | WO2009055796 | 4/2009 |
| WO | WO2009109045 | 9/2009 |

* cited by examiner

SYSTEMS AND METHODS FOR VERTEBRAL DISC REPLACEMENT

CROSS-REFERENCE TO RELATED APPLICATIONS

This application is a continuation of:

U.S. patent application Ser. No. 14/505,972 filed Oct. 3, 2014, entitled SYSTEMS AND METHODS FOR VERTEBRAL DISC REPLACEMENT, which is a continuation of:

U.S. patent application Ser. No. 12/323,068 filed Nov. 25, 2008, entitled SYSTEMS AND METHODS FOR VERTEBRAL DISC REPLACEMENT, now patented as U.S. Pat. No. 8,852,193, which is a continuation-in-part of:

U.S. patent application Ser. No. 12/258,961 filed Oct. 27, 2008, entitled SYSTEMS AND METHODS FOR VERTEBRAL DISC REPLACEMENT, now patented as U.S. Pat. No. 8,894,709, which is a continuation-in-part-of:

U.S. patent application Ser. No. 12/041,910 filed Mar. 4, 2008, entitled JOINT PROSTHESES, now patented as U.S. Pat. No. 9,237,958, which is a continuation-in-part-of:

U.S. patent application Ser. No. 11/559,215 filed Nov. 13, 2006, entitled ARTIFICIAL SPINAL DISC, now patented as U.S. Pat. No. 7,927,374, which is a continuation-in-part of:

U.S. patent application Ser. No. 11/534,014 filed Sep. 21, 2006, entitled ARTIFICIAL SPINAL DISC, now patented as U.S. Pat. No. 8,172,904, which is a continuation-in-part of:

U.S. patent application Ser. No. 10/590,139 filed Feb. 11, 2008, entitled ARTIFICIAL SPINAL DISC, now patented as U.S. Pat. No. 8,100,974, filed as a U.S. national stage filing of:

International Application No. PCT/US2005/023134 filed Jun. 30, 2005, entitled ARTIFICIAL SPINAL DISC, which claims the benefit of:

U.S. Provisional Application Ser. No. 60/658,161 filed Mar. 4, 2005, entitled ARTIFICIAL SPINAL DISC, and U.S. Provisional Application Ser. No. 60/584,240 filed Jun. 30, 2004, entitled ARTIFICIAL DISK FOR DEFORMITY CORRECTION.

U.S. patent application Ser. No. 12/258,961 filed Oct. 27, 2008, entitled SYSTEMS AND METHODS FOR VERTEBRAL DISC REPLACEMENT claims the benefit of:

U.S. Provisional Application Ser. No. 60/982,627 filed Oct. 25, 2007, entitled ALTERNATE ARTICULATION SURFACE ARTIFICIAL CERVICAL DISC, U.S. Provisional Application Ser. No. 60/983,500 filed Oct. 29, 2007, entitled ALTERNATE ARTICULATION SURFACE ARTIFICIAL CERVICAL DISC, U.S. Provisional Application Ser. No. 61/023,019 filed Jan. 23, 2008, entitled VERTEBRAL DISC REPLACEMENT INSTRUMENTS AND PROCEDURE, U.S. Provisional Application Ser. No. 61/041,086 filed Mar. 31, 2008, entitled VERTEBRAL DISC REPLACEMENT INSTRUMENTS AND PROCEDURE, U.S. Provisional Application Ser. No. 61/050,531 filed May 5, 2008, entitled ARTIFICIAL DISC INSTRUMENTS AND METHODS, and U.S. Provisional Application Ser. No. 61/074,498, filed Jun. 20, 2008 and entitled COMPLIANT PROSTHESIS FOR BALANCE CONTROL ARTHROPLASTY.

Prior application U.S. patent application Ser. No. 12/323,068 filed Nov. 25, 2008, entitled SYSTEMS AND METHODS FOR VERTEBRAL DISC REPLACEMENT is also a continuation-in-part of:

prior U.S. patent application Ser. No. 12/258,977 filed Oct. 27, 2008, entitled SYSTEMS AND METHODS FOR VERTEBRAL DISC REPLACEMENT, now patented as U.S. Pat. No. 8,454,699.

The above-identified documents are hereby incorporated herein by reference.

TECHNICAL FIELD

The present invention relates to orthopedic medicine, and more specifically to methods and devices for the treatment of disc disease and spinal deformities with artificial disc replacement.

BACKGROUND OF THE INVENTION

Spinal arthroplasty is an emerging field that offers the promise of restoring and/or maintaining normal spinal motion. The goal of spinal arthroplasty is to reduce or eliminate adjacent segment disease (ASD) by maintaining the normal spinal biomechanics at the operative level. To accomplish this, an artificial cervical prosthesis must duplicate as closely as possible the natural spinal biomechanics, including maintaining the axial height of the disc as well as applying angular adjustment throughout the full range of motion of the natural spine.

The spine plays an integral role in neural protection, load bearing and motion. The vertebral column provides a strong, yet mobile central axis for the skeleton and is composed of twenty-four vertebral bodies with seventy-five stable articulations. The intervertebral disc is a fundamental component of the spinal motion segment, providing cushioning and flexibility. Adjacent vertebrae are linked together by three articulations: a) the vertebral bodies and disc, which transmit compressive and shear loads and provide flexibility, and b) by two facet joints, which protect the disc from translational shear stress and limit rotation. This "triple joint complex" allows for flexion, extension, lateral bending and rotation of the spine.

The intervertebral disc is composed of an inner gel-like matrix called the nucleus pulposus and an outer surrounding fibrous band called the annulus fibrosus. When compressive loads are placed on the spine, increased pressure in the nucleus pulposus is transmitted to the annulus, which bulges outwards. The degenerative cascade of the intervertebral disc initially involves desiccation of the nucleus pulposus. With decreased elasticity and dampening from the nucleus, increased loads are transmitted to the annulus and facets. The increased stress on the annulus can lead to fissures and radial tears in its collagen fibers. With further degeneration, this can lead to circumferential bulging of the disc, contained and uncontained disc herniations, and complete desiccation of the disc. This degenerative cascade can result in axial pain, by stimulating pain fibers in the annulus, or compression of spinal nerve roots and/or the spinal cord. This can manifest itself in motor weakness, pain and/or numbness in the arms or legs or both.

The structure and function of the discs may be altered by a variety of factors including repeated stress, trauma, infection, neoplasm, deformity, segmental instability and inflammatory conditions. Degeneration of the intervertebral disc is the most common etiology of clinical symptoms referable to the spine. Degeneration of the spine is a universal concomitant of human aging. In the cervical spine, neck and arm pain caused by nerve root compression has been estimated to affect 51% of the adult population. Spondylosis of the spine and aging are intimately related, with spondylosis increasing in both prevalence and severity with age. Fortunately, the majority of patients will improve without surgery. In approximately 10-15% of cases, spondylosis is associated with persistent nerve root and spinal cord compression and/or spinal pain, with a small percentage ultimately requiring surgery.

The most common type of surgery used in the United States for the treatment of degenerative disorders of the spine (spondylosis) is spinal fusion. In an interbody fusion, the diseased disc is removed and either a wedge of bone from the patient's hip, allograft or a metallic spacer is placed between the vertebrae where the disc was removed. This immobilizes the functional spinal unit. While this surgery has been successful in eliminating motion, there are disadvantages associated with it. By converting a mobile, functional spinal unit into a fixed, nonfunctional one, fusion results in increased strain patterns at levels adjacent to the fused segment. When a segment of the spine is fused, there is elimination of motion at the level of surgery. Therefore, the stresses that would normally be absorbed by the disc at the site of surgery are now transferred to adjacent segments. This can cause adjacent segment disease (ASD) to one or several spinal units adjacent to the affected level. ASD can be defined as a clinical syndrome of symptomatic degenerative changes occurring adjacent to a previously fused motion segment. Retrospective studies have estimated that ASD can occur in the cervical spine at a rate as high as 2.9% per year with a projected survivorship rate of 26% at 10 years (Hilibrand A S, Carlson G D, Palumbo M, Jones P K, Bohlman H H: Radiculopathy and myelopathy at segments adjacent to the site of a previous anterior cervical arthrodesis. J Bone Joint Surg (Am) 81:519-528, 1999).

In the cervical spine, thousands of North Americans undergo surgery for cervical spondylosis each year. The majority of these procedures involve an anterior discectomy with decompression of the spinal cord and/or nerve root. The primary indication for surgery in the management of cervical spondylosis is radiculopathy, myelopathy and/or neck pain. Following the discectomy, an anterior interbody fusion is commonly performed. Autologous bone harvested from the iliac crest or cadaveric bone is most commonly used to fill the space created by the removal of the disc. A number of other solutions have been suggested, including metallic devices such as fusion cages or other types of spacers, xenografts such as bovine bone, and biological strategies such as the use of growth factors. The graft for the interbody fusion can be shaped to correct underlying deformity of the cervical spine. By contouring the graft one can restore lordosis to a straight or kyphotic spine.

A more recent alternative to spinal fusion is replacement of the damaged disc with a motion preservation device, which includes either a nucleus or total disc replacement (TDR). The rationale for the development of the artificial disc is to prevent adjacent segment disease. Artificial disc devices can be broadly divided into two categories, those that replace the nucleus only, leaving the annulus and vertebral body end plates intact and those that involve replacement of the disc and addition of prosthetic end plates. Both strategies are directed at restoration of intervertebral disc function. Prosthetic nuclei are described, for example, in U.S. Pat. Nos. 5,047,055 and 5,192,326. United States Patent application US2002/0183848 also discloses a prosthetic spinal disc nucleus that has a hydrogel core surrounded by a constraining jacket.

There are several different types of prosthetic devices for use in the cervical or lumbar segments of the spine designed for TDR. For example, the Prodisc™ and the Charite™ disc are composites of cobalt chromium end plates with a polyethylene core. The Prodisc™ is described in U.S. Pat. No. 5,314,477 and the Charite™ disc is described in U.S. Pat. Nos. 5,401,269 and 5,556,431. The Prestige™ disc is another type of artificial disc that comprises a metal on metal design with a ball and trough articulation. Another type of artificial disc that is gaining popularity in the cervical spine is the Bryan® disc, described in several United States Patent applications including 2004/0098131; 2004/00544411; and 2002/0 128715. The Bryan® disc is a composite artificial disc with a low friction, wear resistant, elastic nucleus that articulates with two circular metal plates.

Presently, there are at least four artificial cervical disc replacement systems undergoing clinical trials worldwide. These include unconstrained devices, such as the PCM cervical disc. These unconstrained devices do not have mechanical stops to limit their range of motion. The Bryan® Cervical disc, the Prodisc™ C and the Prestige™ LP cervical disc systems limit range of motion to varying degrees. These systems can be considered semi-constrained, in that there are mechanical stops outside the normal range of motion.

Artificial spinal discs have been implanted for the management of degenerative disc disease producing radiculopathy, myelopathy and/or axial spinal pain. More recently, artificial discs have been adopted for the treatment of trauma. The aim of TDR is to reproduce the biomechanics of the natural disc. Early clinical and biomechanical studies with single and multi-level disc replacement have reported favorable clinical outcomes and preserved range of motion at the level of surgery. Preservation of range of motion, however, while an important feature of an artificial disc, is only a single measure of spinal biomechanics. The effect of the disc on angulation at the operative level, the average disc space height, and overall spinal alignment (sagittal and coronal balance) also needs to be considered.

While the introduction of artificial discs has led to many successful surgeries, there are still problems associated with the current discs. For example, all of the current artificial cervical discs have a fixed height across the entire disc. The artificial discs presently available can have issues with focal kyphosis or kyphosis at adjacent segments of the spine after the patient post-operatively reassumes an upright position, supporting the weight of the head and body. For instance, with the Bryan® disc, the end plates are allowed to move freely about all axes of rotation, allowing the end plate to assume a position resulting from the forces exerted on the implant by the head and neck. At times, this position may be significantly different from the positioning of the disc intra-operatively. Several published studies with the Bryan® cervical disc replacement system have reported a tendency for the end plates of the prosthesis and the alignment of the cervical spine to develop kyphosis following surgery. [Pickett G E, Mitsis D K, Sekhon L H et al. Effects of a cervical disc prosthesis on segmental and cervical spine alignment. *Neurosurg Focus* 2004;17(E5):30-35; Johnson J P, Lauryssen C, Cambron H O, et al. Sagittal alignment and the Bryan® cervical disc. *Neurosurg Focus* 2004;17(E14):1-4; Sekhon L H S. Cervical arthroplasty in the management of spondylotic myelopathy: 18 month results. *Neurosurg Focus* 2004; 17(E8):55-61.] This kyphotic angulation of the prosthesis has been attributed to the passive (unconstrained motion with a mobile nucleus and variable instantaneous axis of rotation) design of the implant. None of the current TDR systems addresses this major complication.

A significant number of patients with spinal disc disease have a loss of sagittal alignment of the spine as a result of the degenerative process. In addition, varying degrees of coronal imbalance can also occur. None of the available artificial disc replacement systems are designed to restore normal alignment to a spine that is straight, which have focal/global kyphosis or coronal deformity. Existing artificial disc replacement systems that are inserted into either a straight, kyphotic or angulated segment are likely to take on the angle and local biomechanics determined by the facets, ligaments and muscle forces. As such, patients with a pre-operative straight spine may develop post-operative kyphosis, and patients with a pre-operative kyphosis may have a worsening of the deformity post-operatively. Kyphosis of the spine has been implicated in segmental instability and the development of clinically significant degenerative disease. Several clinical studies have described that a change in the sagittal or coronal balance of the spine can result in clinically significant axial spinal pain as well the initiation and/or the acceleration of ASD. [Kawakami M, Tamaki T, Yoshida M, et al. Axial symptoms and cervical alignment after anterior spinal fusion for patients with cervical myelopathy. *J Spinal Disord* 1999; 12:50-60; Harrison D D, Harrison D E, Janik T J, et al. Modeling of the sagittal cervical spine as a method to discriminate hypolordosis: results of elliptical and circular modeling in 72 asymptomatic subjects, 52 acute neck pain subjects, and 70 chronic neck pain subjects. *Spine* 2004; 29:2485-2492; Katsuura A, Hukuda S, Saruhashi Y, et al. Kyphotic malalignment after anterior cervical fusion is one of the factors promoting the degenerative process in adjacent intervertebral levels. Eur Spine J 2001; 10:320-324; Ferch R D, Shad A, Cadoux-Hudson T A, Teddy P J. Anterior correction of cervical kyphotic deformity: effects on myelopathy, neck pain, and sagittal alignment. J Neurosurg 2004; 100:S13-S19; Katsuura A, Hukuda S, Imanaka T, Miyamoto K, Kanemoto M. Anterior cervical plate used in degenerative disease can maintain cervical lordosis. J Spinal Disord 1996; 9:470-476.]

Attempting to provide a deformity correction by simply altering the end plate or the nucleus of an artificial disc, while still maintaining free movement about all axes of rotation, may not be sustainable as the forces exerted by the head and body on the artificial disc could counteract the desired correction. To provide a sustainable correction, some limitation on the axes of rotation is required. From a design perspective, the goal is to design an artificial disc that is able to correct deformity (coronal and sagittal), has mechanical stops outside the normal range of motion (semi-constrained), and preferably has variable instantaneous axis of rotation (IAR).

The limits on the axes of rotation can fall into two categories. One is to provide correction using a permanent rotation or translation of an axis to support the correction. This is accomplished using the geometries of the core and end plates themselves and is referred to the Geometric Constraint category. The second is to keep free range of motion about all axes but provide the correction using a material support. This type of design provides the correction by the imposition of a deformable material in the plane of correction for normal rotation in that plane. This is the Material Constraint category of designs.

Degenerative disc disease is a major source of morbidity in our society. It can lead to serious economic and emotional problems for those afflicted. Thus, there is a need for an artificial disc that can alleviate both symptoms and correct deformity (sagittal or coronal or both) of the spine.

BRIEF DESCRIPTION OF THE DRAWINGS

The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention. These and other features of the invention will become more apparent from the following description in which reference is made to the appended drawings wherein.

DETAILED DESCRIPTION OF THE PREFERRED EMBODIMENTS

Figure 1:
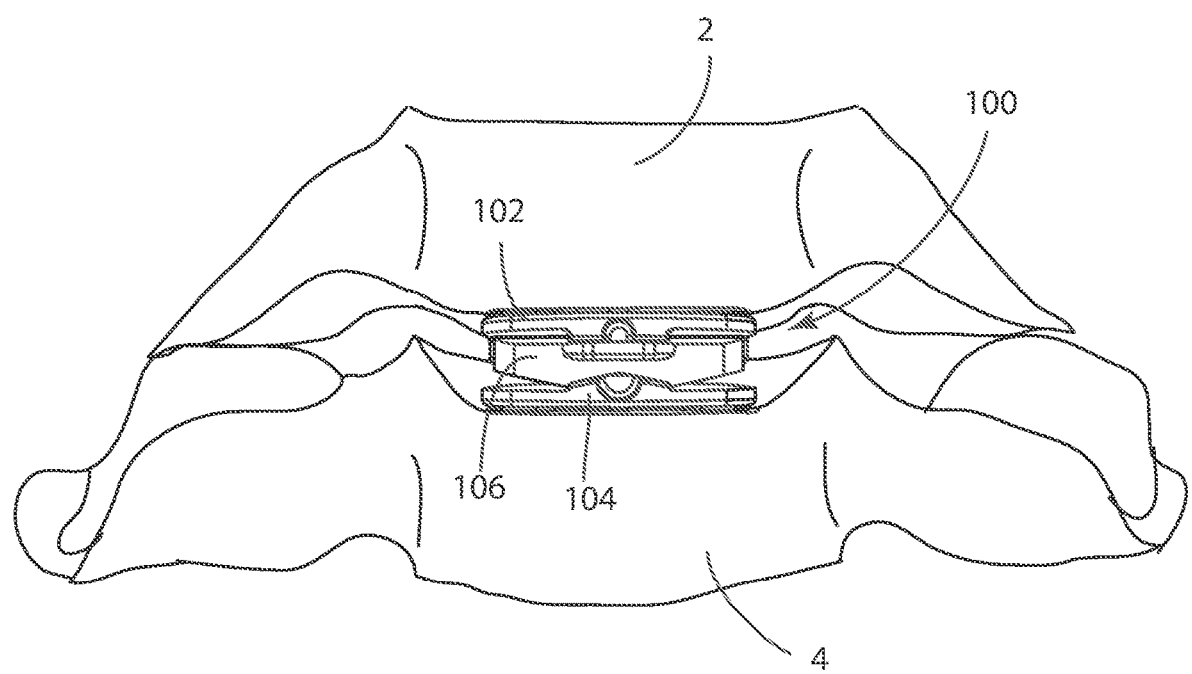
FIG. 1 illustrates an anterior view of two cervical vertebrae with an artificial disc prosthesis implanted between the vertebrae, the artificial disc prosthesis comprising a superior end plate, a nucleus which provides 6° of lordotic correction, and an inferior end plate.

The present invention relates to systems and methods for the treatment of disc disease and spinal deformities with an artificial disc replacement. Those of skill in the art will recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

In its proper, healthy alignment, the spine follows natural curves, which promote proper sagittal and coronal balance (flexibility) and allow for balanced load sharing between the vertebrae. These curves include the cervical, thoracic, lumbar and sacral regions of the spine. Naturally, in order to accommodate a curve, there must be some variation in the angle of articulation between the functional spinal units and the height of an intradiscal space. The cervical and lumbar regions are naturally lordotic or curved convexly in the anterior direction. At different segments along the spine, there are typically different heights for the vertebral bodies and the intradiscal space. In addition, the intradiscal space and vertebral body height may be different for different people.

Each intradiscal space has anterior and posterior regions. An artificial disc in the cervical, thoracic and lumbar regions that maintains the same height from the anterior to the posterior may promote an abnormal alignment, resulting in additional stress at the anterior or posterior portions of an adjacent disc. It may also result in an uneven load distribution across the device and cause an excessive amount of relative motion, wear debris and early failure.

As used herein, the terms, nucleus and core are used interchangeably to refer to an artificial intervertebral device that replaces a damaged natural spinal disc. The artificial core may be provided alone or in combination with a superior end plate for attachment to an upper vertebra or an inferior end plate for attachment to a lower vertebra or both.

The terms "upper" and "lower" are used herein to refer to the vertebrae on either side of the disc to be replaced, or a surface on a part in the position shown in the referenced drawing. A "superior" plate is affixed to an upper vertebra and an "inferior" plate is affixed to a lower vertebra of a functional spinal unit.

The terms vertical and horizontal are used herein relative to a standing human being in the anatomical position. The term "anterior" refers to the region towards the front and the term "posterior" refers to the region towards the back. The term "sagittal" refers to regions on either side of the central midline axis of a standing human being. The term "sagittal plane" used herein refers to a vertical plane extending along the central midline axis of the vertebral bodies of the spine, dividing the body into left and right lateral regions. The term "coronal plane" refers to a vertical plane extending along the central midline axis of the vertebral bodies of the spine, dividing the body into anterior and posterior regions through the center of the vertebral bodies. The term "cephalad-caudal axis" refers to a vertical axis which extends along the central midline axis of the vertebral bodies of the spine.

The term "asymmetrical" is used herein to refer to an axis of maximum height that is not placed centrally or to a nucleus or total disc replacement (TDR) not having its maximum vertical axis placed centrally. In other words, the maximum height is not situated or pivoted at a center line of symmetry so that the TDR comprises regions that are not exactly the same in shape or size as other regions on the other side of a line of symmetry. The location of maximal load bearing is located in a non-central location. The term may analogously apply to joint prostheses in which an axis of maximum height is not located centrally on a substantially convex bearing surface, or the axis of maximum depth of a depression is not placed centrally on a substantially concave bearing surface.

The term "normal alignment" is used herein to refer to the natural positioning of functional components of a healthy joint, relative to one another and/or the surrounding tissues. Normal alignment may refer to the static position of a joint at rest, wherein no stress or pressure is placed on the joint, and it may also refer to the dynamic position of a joint under natural mechanical stress such as during flexion or extension. Normal alignment may also be referred to as natural, healthy, or proper alignment. "Preferred" or "desired" alignment are used herein to refer to joint alignment that may be natural, or corrected, but places the joint components in a functional or desired position. The terms "preferred orientation" or "preferred relative orientation" used herein also refer to component alignment that may be natural, or corrected, in which the joint components are in a functional or desired position.

The phrase "preferred relative orientation" may refer to an orientation about a single axis, or about multiple axes. For example, an artificial disc implant may be designed to establish a preferred relative orientation about an axis extending medial-laterally to provide a preferred anterior-posterior angulation that mimics the appropriate lordosis or kyphosis of the joint motion segment. Alternatively, an artificial disc implant may be designed to establish a preferred relative orientation about an axis extending generally anterior-posteriorly to provide a preferred medial-lateral angulation that provides the desired degree of lateral bending. Such lateral bending may be zero degrees, reflecting the straightness of a healthy spine, or may be nonzero to the left or right to provide correction for various pathologies including scoliosis. As another alternative, an artificial disc implant may be designed to provide a preferred relative orientation about both of the medial-lateral and anterior-posterior axes to encourage proper lordosis or kyphosis while also encouraging the desired lateral bending. A preferred relative orientation may also be a low energy position in which the joint is naturally encouraged to remain, in contrast to a point of resistance such as a motion stop.

An "orientation feature" is a feature present on one or more joint components that help the components establish a preferred relative orientation. For example, opposing bearing surfaces on joint components may include flattened sections, which cooperate to urge the components toward attaining a preferred relative orientation. Matching curved surfaces which align better in a preferred relative orientation may also be orientation features. Other configurations of orientation features may be possible in addition to flat and curved surfaces.

It has been found that nucleus body designs with a completely rounded surface (not necessarily spherical) have issues with reliably maintaining correction when exposed to the variable forces of the head and neck. To address this issue, one or more segments or sections that is flat or which has a contour different from the adjacent surface, can be formed in the nucleus body. This section will be referred to as a flattened section, which is meant to refer to any contour that is not the same as the adjacent surface(s) of the nucleus. Such a flattened surface can be planar or it can have other shapes such as a slight convex or concave shape with a radius of curvature different from the adjacent surface. Such a flattened surface could also be in the shape of a compound curve or other complex shape. A flattened section may also refer to a rectilinear portion of a two-dimensional shape. In the example of providing a lordotic correction, the flattened segment can be angled relative to the superior end plate of the inferior vertebral body with the height of the anterior part being greater than the height of the posterior part. The overall shape of the nucleus body is still asymmetric, but the flattened segment is incorporated to provide a reliable correction of the deformity. This flattened segment provides stabilization to resist the moments acting through the nucleus, i.e., if the flat is not of adequate size, there may be a tendency for the correction to disappear in the presence of an anterior load or for a hyper-lordotic over correction in the presence of a posterior load (during lordotic correction). An additional advantage of incorporating a flattened segment in the nucleus is to provide surface contact over that area during small motions about the resting, neutral position of the device, which may help reduce the stresses and potentially wear of the device.

This flattened surface can be angled relative to the superior end plate of the inferior vertebral body (or vice versa, or both), with the height of the anterior end being greater than the height of the posterior end when lordotic correction is sought. The overall shape of the core can still be asymmetric, but the flattened surface can be incorporated to provide a reliable correction of the deformity. Alternatively, the core may have flattened sections but be symmetric and the endplates may be asymmetric or angled to provide the lordotic correction.

The invention includes a novel artificial disc that provides the normal range of motion of the natural intervertebral disc, along with the ability to correct deformity of the spine. The proposed disc allows for semi-constrained range of motion of the functional spinal unit. It reproduces the kinematics of the pre-operative normal spine in all motions. Of particular, the proposed disc allows for independent & mobile centers of rotation in the flexion-extension and lateral-bending motions, which is unique to this device but an inherent characteristic of the natural spine. It possesses maximum durability and biocompatibility, and a means for integrating itself into the spine bony structure for long-term stability. Its insertion is safe, simple, and surgical time is not compromised compared with the current procedures. In contrast to the existing disc replacement systems, it will allow the surgeon to correct deformity while maintaining natural kinematics of the spine.

In at least one embodiment of the present invention, an artificial disc comprises a nucleus that is not geometrically symmetrical. The disc may have a maximum vertical axis that is not located at the geometric center of the disc. The maximum vertical axis may be located toward the front of the disc, the rear of the disc and/or on one side of the disc. The positioning of the maximum vertical height and load bearing capability is chosen depending on the type of deformity that needs to be corrected. The present invention also provides methods for the treatment of disc/vertebral body disease, lordosis, kyphosis and scoliosis using an asymmetric artificial disc.

One advantage of the present invention is that the "nucleus" or core may be interchanged and revised intra-operatively and post-operatively. Instruments can be used to gauge the need for and amount of correction and the appropriate implant can then be inserted. By introducing correction into the nucleus, the surgeon benefits from flexibility, ease of insertion and revisability that present systems do not provide.

Artificial discs of the present invention can be provided with various degrees of deformity correction. For this aspect of the invention, the surgeon can choose a disc having the appropriate correction for the patient. Thus, a method of treating a spinal deformity is provided. This method comprises preparing a spinal segment for implantation of an artificial disc, determining the desired angle of the intervertebral space, selecting an artificial nucleus having the desired dimensions, affixing a superior end plate to the upper vertebra, affixing an inferior end plate to the lower vertebra and inserting the selected nucleus between the superior and inferior end plates. Alternatively, and the assembled unit of end plate-nucleus-end plate may be inserted in unison. The configuration of the nucleus in this pre-assembled construct can be determined by the intra-operative measurement tools, or with pre-operative calculations. Pre-operative planning techniques and instruments may also be able to determine the size and orientation of this device for insertion.

A major advantage of the present system is that the artificial disc can be more easily and rapidly inserted and the nucleus can be changed or revised in accordance with the magnitude of the deformity being corrected. This is especially useful in children and young adults where the alignment of the spine changes over time.

In at least one embodiment, an asymmetric nucleus adapted for lordotic correction of the cervical spine is provided. The surgeon can restore lordosis to the cervical spine while maintaining motion. The nucleus may be composed of a low friction elastomer such as polyurethane, polycarbonate-polyurethane, a polymer such as polyethylene (particularly ultra-high molecular weight polyethylene or UHMWPE), a suitable ceramic, metals, metal matrix composites such as titanium carbide, or metal alloys such as titanium or a titanium alloy, chrome-cobalt-molybdenum (CoCrMo), cobalt chrome, stainless steel, or other suitable materials. It has a generally trapezoidal geometric design, with varying degrees of lordosis incorporated into it by utilizing an axis of maximum height anterior to the geometric center of the nucleus. The anterior height of the nucleus varies, depending on the extent of lordotic correction needed. The nucleus may be available in various lordotic angles, e.g. 0, 3° and 6°, as well as differing heights (e.g., 4, 6 and 8 mm).

Before deciding on the final nucleus size, a set of instruments could be inserted to confirm the lordotic correction, but these may also be used as confirmation for other types of pre-surgical planning techniques and instrumentation. Alternatively, intra-operative instruments may be used as confirmation for other types of pre-surgical planning techniques and instrumentation.

In one embodiment, the implant consists of three pieces; a superior end plate, an inferior end plate, and the nucleus. The end plates will be made in differing sizes to accommodate differences in anatomy. These may be fabricated of titanium, titanium carbide, or a titanium alloy, cobalt-chrome-molybdenum (CoCrMo), cobalt chrome, stainless steel, metal matrix composites, or other materials suitable for spinal prosthetic inserts. They may also be mainly fabricated from one or more materials and utilize a separate coating surface or material layer for optimizing mechanical and wear performance. Coatings could be used for lubricity, low-friction, enhanced hardness, low surface energy, roughness, or other desirable characteristics for an articulating joint.

The end plates can have two distinct surfaces. The flat surface of each end plate, which contacts the vertebral body end plate, is capable of accommodating bony ingrowth and incorporates a suitable coating, such as porous titanium, a calcium phosphate, or includes other types of known surfaces that promote bony ingrowth for long-term stability. The end plates can also have one or more parasagittal keels or teeth that provide immediate fixation.

While the embodiments illustrated below include three-piece protheses with two end plates and a nucleus, it is appreciated that any nucleus disclosed herein could be integrated with one of the adjoining end plates to provide a two piece embodiment. At least one of the remaining articular surfaces may be augmented by re-shaping of the surface to compensate for the motion lost due to integration.

FIG. 1 illustrates an embodiment of an artificial disc replacement implanted in an intervertebral space between two adjacent vertebrae in a portion of a spine. Artificial disc prosthesis 100 comprises a superior end plate secured to a superior vertebral body 2, an inferior end plate 104 secured to an inferior vertebral body 4, and a nucleus 106 positioned between the superior and inferior endplates. Securing an end plate to a vertebral body comprises coupling the end plate to the vertebral body so that it remains in place at least long enough for bony ingrowth to occur. The disc prosthesis 100 comprises a plurality of articulating surfaces which form articulating joints, permitting restoration of intervertebral motion including flexion/extension, anterior/posterior translation, lateral bending and axial rotation, between the end plates. The disc prosthesis 100 further comprises orientation features which may allow the joints to remain in a preferred orientation relative to one or more axes, which may be a neutral low energy position which the joint is naturally encouraged to maintain.

Figure 2:
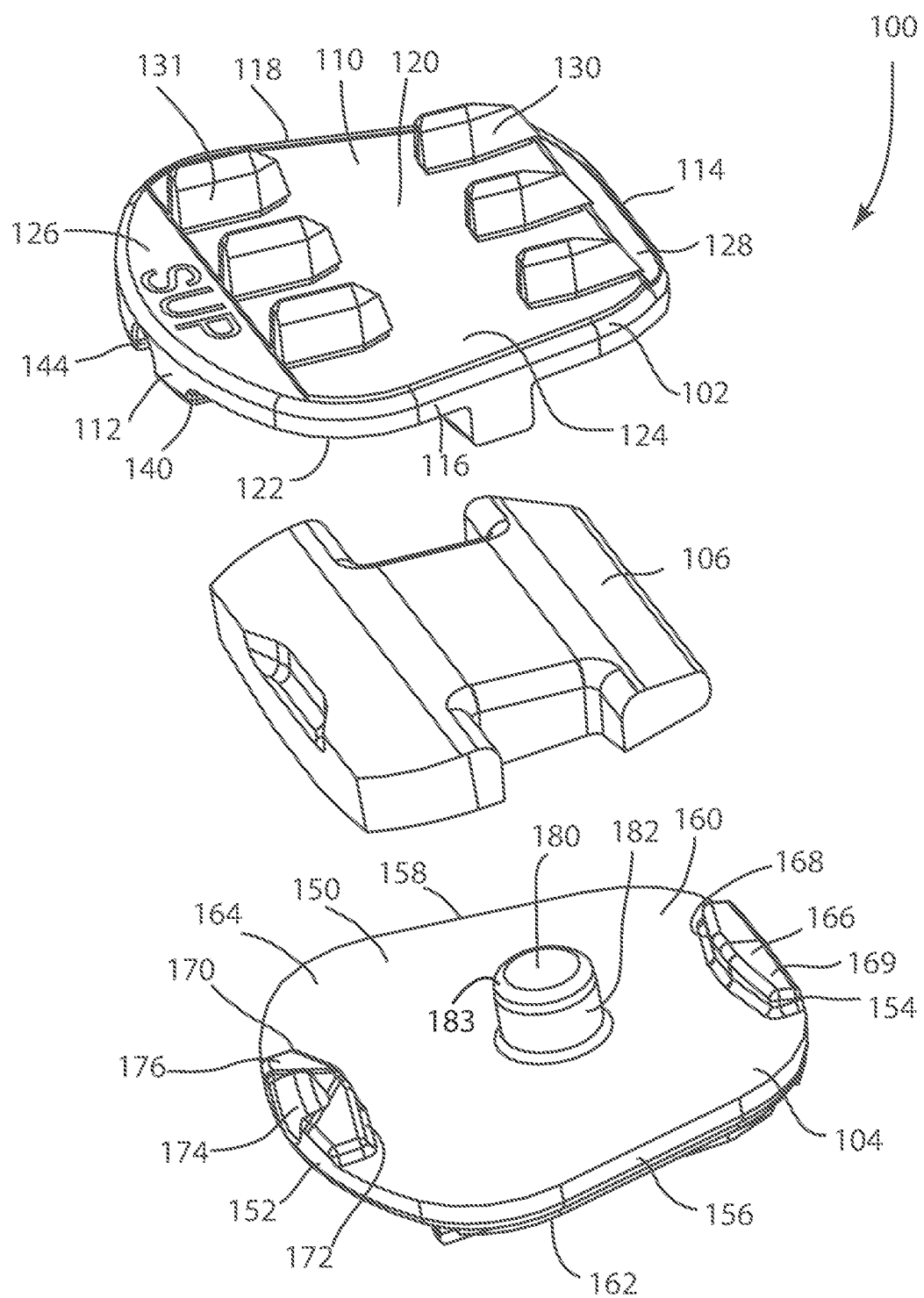
FIG. 2 illustrates an exploded top perspective view of the superior end plate, nucleus, and inferior end plate of FIG. 1.
Figure 3:
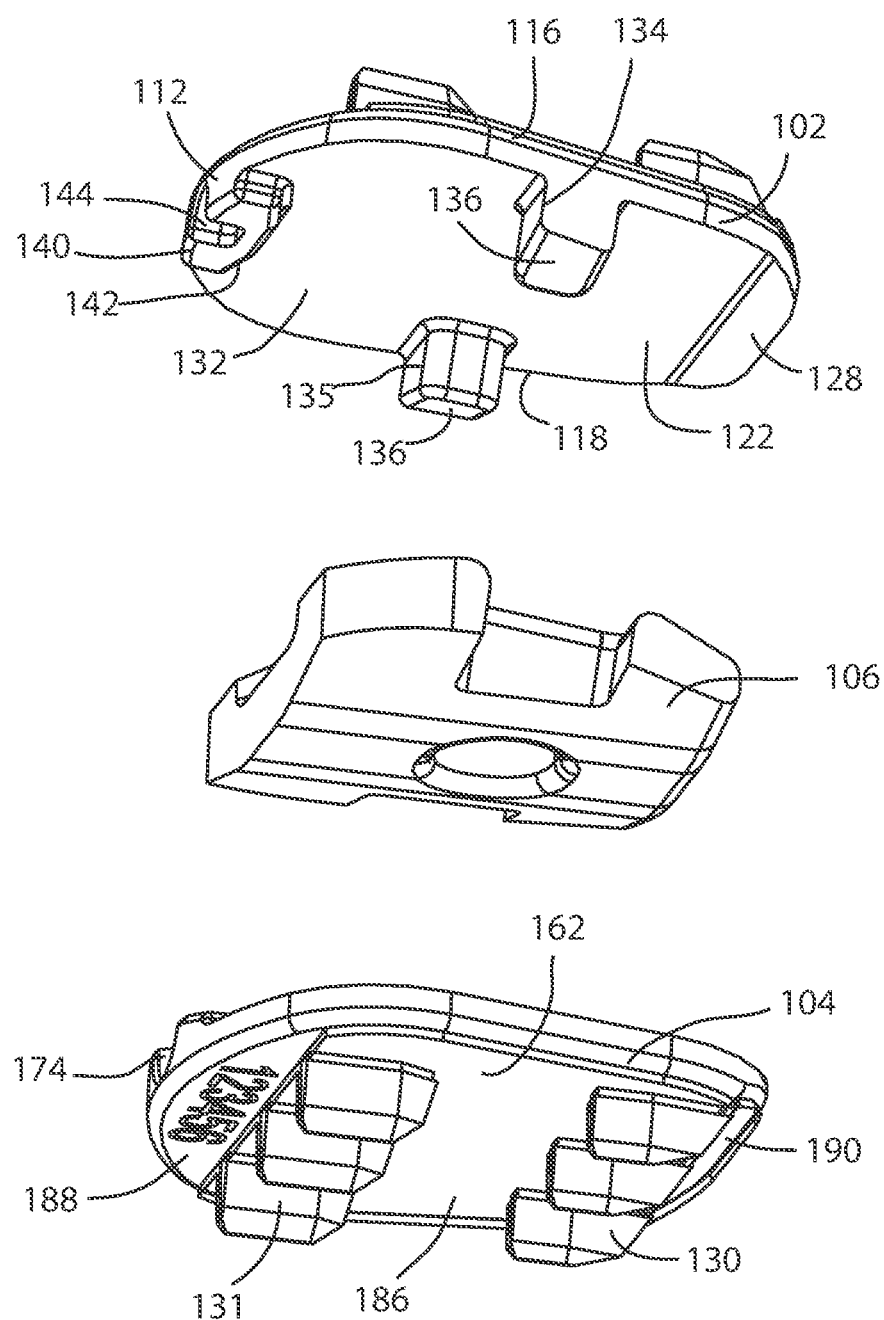
FIG. 3 illustrates an exploded bottom perspective view of the superior end plate, nucleus, and inferior end plate of FIG. 1.

FIGS. 2 and 3 illustrate exploded perspective views of the disc replacement 100; FIG. 2 from a cephalad-lateral perspective and FIG. 3 from a caudal-lateral perspective. Various features of the end plates 102, 104 are visible in these views. Each end plate 102, 104, is generally trapezoidal in shape, although alternative shapes such as rectangular, circular, oval or kidney, among other, are contemplated for other embodiments of the invention. Superior end plate 102 comprises an end plate body 110 with an anterior end 112, posterior end 114, left lateral side 116, right lateral side 118, superior side 120 and inferior side 122. The superior side 120 has a bone engagement surface 124 which is essentially flat, enabling it to easily contact the surface of the natural vertebral end plate. Use of a flat bone engagement surface may eliminate extra surgical time needed to prepare the vertebrae to the appropriate shape to accommodate the end plate. However, it is appreciated that other embodiments of the invention may include end plates which are do not have flat bone engagement surfaces, but shaped surface which may be generally concave or convex. The bone engagement surface can be porous and incorporate a suitable treatment, such as porous titanium, a calcium phosphate or other types of known treatments such as coatings, plasma sprays, and structural changes to the surface, that promote bony ingrowth or ongrowth for long-term stability. An anterior portion 126 of the end plate 102 may not incorporate the ingrowth treatment, to allow for easier instrument insertion and gripping. A posterior angled portion 128 of the body slopes caudally at an acute angle from the remainder of the body 120, allowing for ease of insertion of the prosthesis into the intervertebral space during implantation. A plurality of first teeth 130 and second teeth 131 may project outwardly from the bone engagement surface 124.

The inferior side 122 of the superior end plate 102 comprises an essentially planar articular surface 132. Two flanges, a left flange 134 and a right flange 135 protrude caudally from the articular surface, positioned centrally along the lateral sides 116, 118 of the end plate. The flanges 134, 135 are positioned to fit into gaps formed by notches formed in the nucleus 106. Other embodiments may include flanges positioned at the corners of the end plates, or at other locations along the lateral sides. A sloped surface 136 is formed on the inferior side of left flange 134, and a sloped surface 137 is formed on the inferior side of right flange 135. After implantation of the prosthesis and during lateral bending, the sloped surfaces 136 or 137 do not contact a superior surface of the inferior end plate, as an inferior surface of the nucleus instead contacts the superior surface of the inferior end plate to provide a soft stop to the lateral bending motion. The heights of the flanges 134, 135 may vary, and the slope of the sloped surfaces 136, 137 may vary. An anterior-posterior dimension of the flanges 134, 135 may be less than an anterior-posterior dimension of the gaps in the nucleus 106, allowing constrained anterior-posterior translation of the end plate 102 relative to the nucleus. A soft stop may occur when a first component, such as a nucleus, comprising material such as UHMWPE contacts a second component, such as an end plate, comprising a harder material such as titanium or other metals, in a way as to prevent further motion of the first component along the same direction. Conversely, the moving first component may comprise the harder material, and the second component may comprise the relatively softer material.

An anterior retention member 140 is formed along the anterior side of the end plate 102, protruding caudally toward the inferior end plate 104. The anterior retention member 140 may assist in preventing displacement of the nucleus from between the end plates, as the member 140 is positioned anterior to the anterior edge of the nucleus 106. An inner edge 142 of the member 140 is angled to permit limited rotation of the nucleus relative to the end plate 102 to accommodate device axial rotation. This inner edge 142 also serves as an axial rotation stop to limit the amount of axial rotation. The inner edge 142 is also dovetailed to engage gripping arms of a prosthesis insertion tool. A pocket 144 is formed into the anterior portion of the member 140 and serves as a receptacle for instrumentation during implantation, revision or removal of the prosthesis. After implantation of the prosthesis and during flexion of the spine, the anterior member 140 does not contact the inferior end plate 102, as the nucleus contacts the inferior end plate, to provide a motion stop before the member 140 could contact the inferior end plate. Other embodiments of the invention may include multiple anterior members formed on the superior end plate, or no anterior members formed on the superior endplate.

Inferior end plate 104 comprises an end plate body 150 with an anterior end 152, posterior end 154, left lateral side 156, right lateral side 158, superior side 160 and inferior side 162. An essentially planar superior articular surface 164 extends across the end plate body 150. A posterior retention member 166 is formed at the posterior end 154, protruding from the superior side 160. The posterior retention member is bounded by an inner edge 168 which is angled to permit limited axial rotation of the nucleus 106 relative to the end plate 104, and by a superior surface 169 which may be angled laterally and posteriorly to allow lateral bending during extension. An anterior retention member 170 with an angled inner edge 172 is located along the anterior end 152, protruding from the superior side 160 toward the superior end plate 102. A pocket 174 is formed in the retention member 170, which may receive instrumentation during implantation, revision or removal of the prosthesis. A superior surface 176 of the retention member 170 may be angled laterally and anteriorly to permit lateral bending during flexion.

A pin, or post 180 protrudes from the superior side 160 in a cephalad direction toward the superior end plate 102. The post 180 may be located in a geometric center of the inferior end plate 104, or it may be displaced from the geometric center. The location of the post 180, and a corresponding pocket in the nucleus, determines the cephalad-caudal axis about which the nucleus and the opposing end plate may rotate relative to the inferior end plate 102. Generally cylindrical in shape to permit rotation about the cephalad-caudal axis, the post 180 comprises a circumferential wall 182 with a spherical shoulder 183, which may articulate with a wall of the nucleus pocket. To prevent or limit rotation about a cephalad-caudal axis, the post could have a non-cylindrical shape such as a square or triangle, among others. The post 180 also cooperates with the nucleus pocket to permit lateral bending simultaneously with axial rotation.

The inferior side 162 of the inferior end plate 104 comprises a planar bone engagement surface 186, on which one or a plurality of teeth 130, 131 may be formed. An anterior portion 188 may be free of bone ingrowth or ongrowth treatments to allow for engagement with instrumentation. A posterior angled portion 190 of the body slopes cephaladly at an acute angle from the remainder of the bone engagement surface 186, again allowing for ease of insertion of the prosthesis into the intervertebral space during implantation.

Figure 4A:
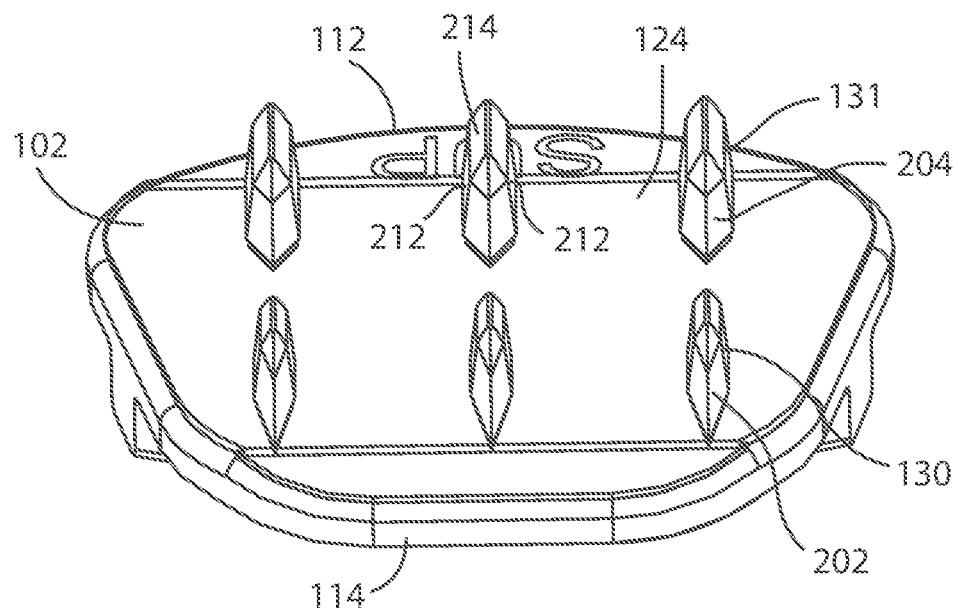
FIG. 4A illustrates a top perspective view of the superior end plate of FIG. 1.
Figure 4B:
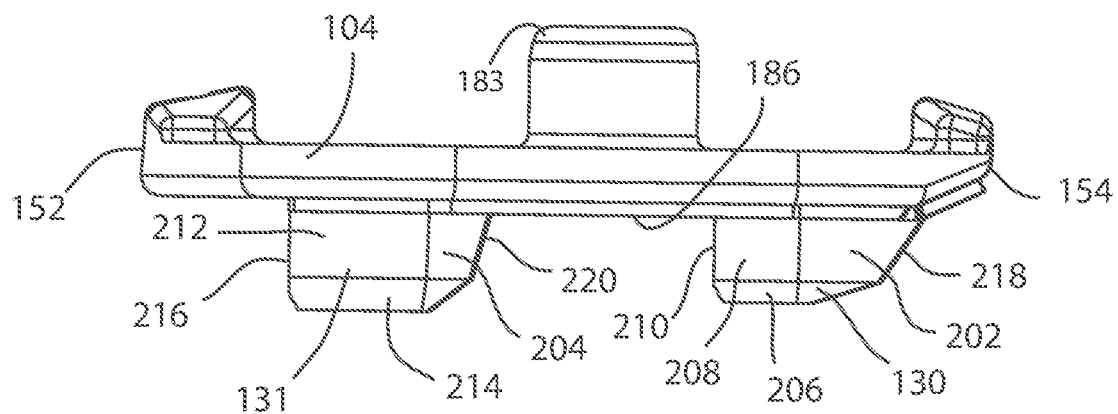
FIG. 4B illustrates a lateral view of the superior end plate of FIG. 1.

Referring to FIGS. 4A and 4B, a plurality of bone engagement features, comprising self-cutting first teeth 130 and second teeth 131, may be formed on the bone engagement surfaces 124, 186 of the superior and inferior end plates. Teeth 130, 131 have sharply pointed leading edges, which cut into the vertebral bodies during insertion and may eliminate extra preparation steps such as pre-cutting or reaming grooves into the surfaces of the vertebral bodies. Each second tooth 131 may be positioned directly behind, or anterior to, a first tooth 130. Each first tooth 130 has a narrowly angled cutting point 202 and is positioned with the point oriented toward the posterior end 114 of the endplate 102. As the end plate is inserted between the vertebral bodies, the sharp cutting point 202 on each first tooth 130 cuts a track into the surface of the vertebral body. As the end plate is slid further in, the second tooth 131 follows in the track the first tooth 130, and a wider cutting point 204 on the second tooth widens the track.

Each first tooth 130 has a pointed apex 206 positioned atop the tooth, supported by a pair of support walls 208 and an end wall 210. The support walls 208 are angled toward one another from the bone engagement surface 124 or 186 to the apex 206. This angulation advantageously permits a solid press-fit as the tooth penetrates the vertebral body, providing immediate anchorage. The angled walls 208 also allow some subsidence of the end plate 102 into the vertebral body after implantation, without the risk of loosening from the vertebral body. The end wall 210 may be vertical or near vertical, promoting retention in the vertebral body and prevention of unintended withdrawal from the vertebral body. In other embodiments of the invention, the walls 208 may not be angled but instead parallel to one another.

Each second tooth 131 comprises the wide cutting point 204, two angled support walls 212 and an end wall 216 which support a pointed apex 214. The second teeth 131 are similar in configuration to the first teeth 130; however particular dimensions such as wall height and the angle and width of the cutting point may vary. For example, as shown in FIG. 4A, second tooth 131 is laterally wider than first tooth 130, while the cutting point 202 of first tooth 130 is narrower than the cutting point 204 of second tooth 131. Looking at FIG. 4B, the support walls 212 and apex 214 of the second tooth 131 are taller, providing a larger vertical dimension than the support walls 208 and apex 206 of the first tooth 130. A posterior leading edge 218 of first tooth 130 is more gently sloped than a posterior leading edge 220 of second tooth 131, which may aid in insertion. All first and second teeth 130, 131 may incorporate the same bone ingrowth or ongrowth treatments as the bone engagement surfaces 124, 186.

Both end plates 102, 104 are general laterally symmetrical; however, in alternative embodiments one or both of the endplates could have a maximum vertical dimension located on one lateral side to provide a scoliotic correction. Similarly, one or both of the endplates could have an anteriorly located maximum vertical dimension to provide a lordotic correction, or a posteriorly located maximum vertical dimension to provide a kyphotic correction. It is appreciated that specific features of the end plates, including but not limited to bone engagement features, motion stops, instrument recesses, and posts, may be swapped, inverted or reversed such that features found on the superior end plate may be instead located on the inferior end plate, and vice versa. Additionally, in alternative embodiments features found on end plates may instead be located on the nucleus, and vice versa.

FIGS. 5A, 5B, 6, 7A, and 7B illustrate various views of the disc nucleus 106. Like the end plates 102, 104, the nucleus has a generally rounded trapezoidal shape, although alternate embodiments may have other shapes. The nucleus 106 comprises a superior side 250, an inferior side 252, an anterior end 254, a posterior end 256, a left lateral side 258 and a right lateral side 260. The superior side 250 comprises a nuclear superior articular surface 262, which further comprises three planar portions: an anterior planar portion 264, a middle planar portion 266, and a posterior planar portion 268. A first curvate transition portion 270 lies between the anterior planar portion 264 and the middle planar portion 266, while a second curvate transition portion 272 lies between the middle planar portion 266 and posterior planar portion 268. The three planar portions are perpendicular to a sagittal plane of the vertebral bodies when the implant is properly implanted in an intervertebral space. The planar portions are not co-planar with respect to one another, although an alternative embodiment of the invention could include one or more co-planar planar portions. An angle a1, the angle between the anterior 264 and middle 266 planar portions, is acute and may be unequal to an angle a2, the angle between the middle 266 and posterior 268 planar portions. In other embodiments, angles a1 and a2 may be equal. The nucleus inferior side 252 comprises an inferior articular surface 280, which, like the superior articular surface, also comprises three planar surfaces separated by two curvate transition portions. A right planar portion 284 is separated from a central planar portion 286 by a first curvate transition portion 290, and the central planar portion 286 is separated from a left planar portion 288 by a second curvate transition portion 292. The three planar portions are not co-planar. When the prosthesis is properly implanted in an intervertebral space, the planar portions are perpendicular to a coronal plane of the vertebral bodies when the implant is properly implanted in an intervertebral space. An angle b1, the angle between the right 264 and central 286 planar portions, is acute and is equal to an angle b2, the acute angle between the central 286 and left 288 planar portions. In alternate embodiments, angles b1 and b2 may be unequal to provide a scoliotic correction.

Figure 8:
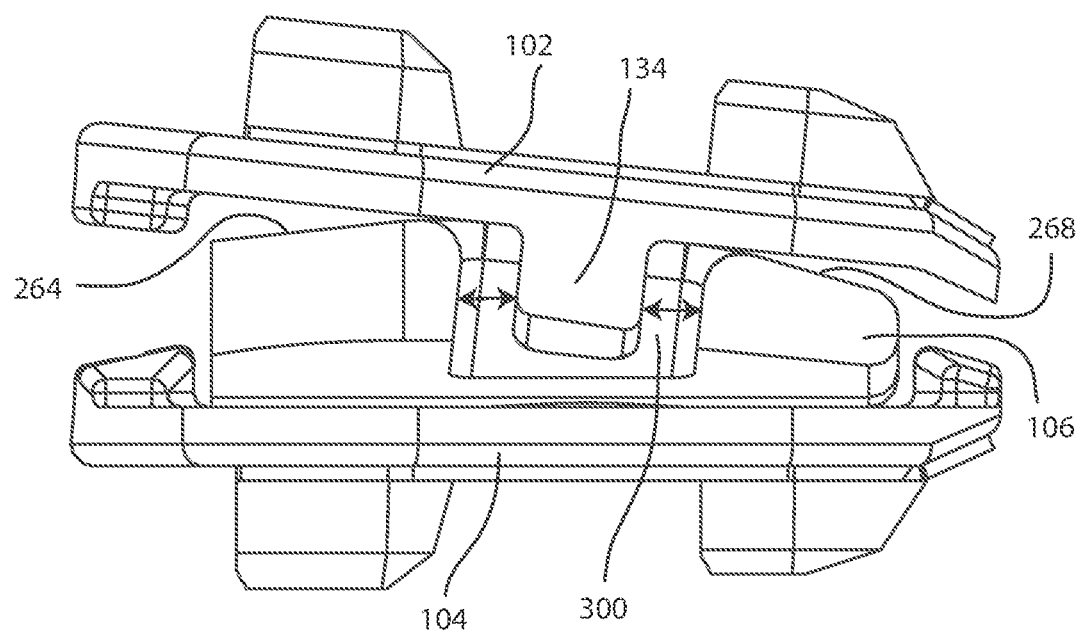
FIG. 8 illustrates a lateral view of the artificial disc prosthesis of FIG. 1 in a preferred orientation.

Two notches are formed in the lateral sides of the nucleus, a left notch 300 and a right notch 302. The left notch 300 defines a left gap 304, through which left flange 134 extends when the nucleus is positioned between the end plates 102, 104. The right notch 302 defines a right gap 306, through which the right flange 135 may extend. Each gap 304, 306 is wider in an anterior-posterior dimension than its respective motion stop, to allow translation of the superior end plate 102 relative to the nucleus 106 and the inferior end plate. FIG. 8 is a lateral view of the left side of the prosthesis, illustrating the relationship of the left flange 134 to the left notch 300 as the prosthesis is in a low-energy neutral position with respect to rotation about both an anterior-posterior axis and a medial-lateral axis. Arrows indicate anterior-posterior translation of the superior end plate 102. A recess 296, visible in FIG. 5A, may be formed in the anterior end 254 toward the superior side 250 of the nucleus. The recess is shaped to receive the anterior retention member 140 of the superior end plate 102 during translation of the superior end plate.

Figure 5A:
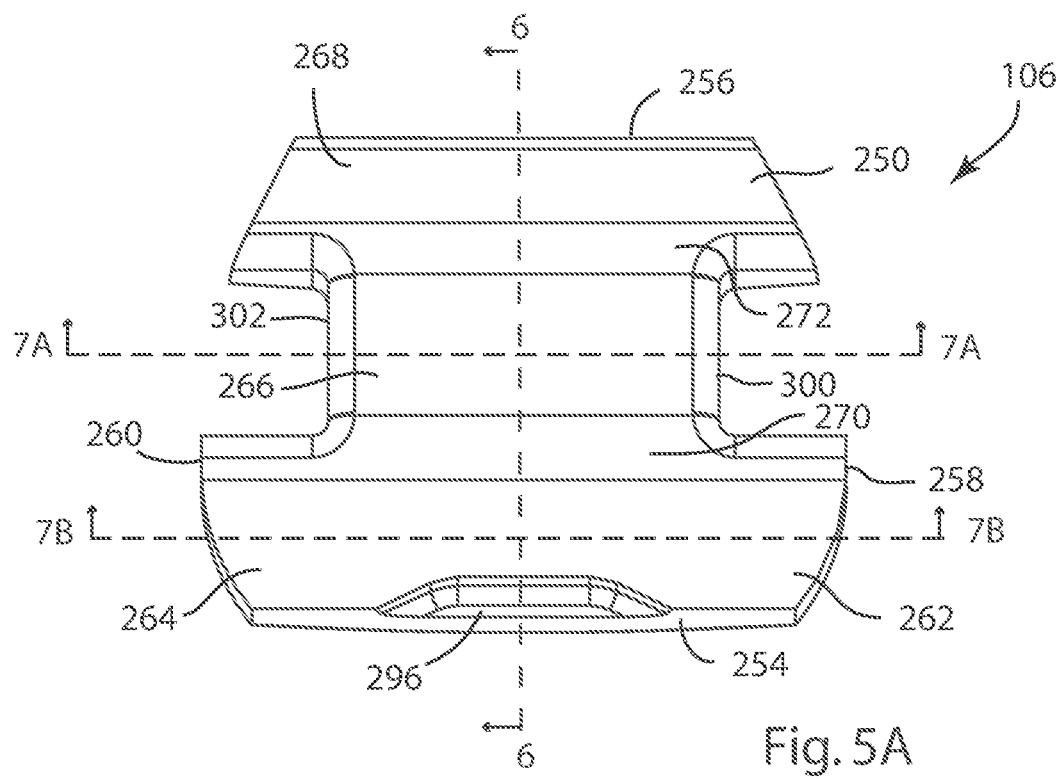
FIG. 5A illustrates a top view of the nucleus of FIG. 1.
Figure 5B:
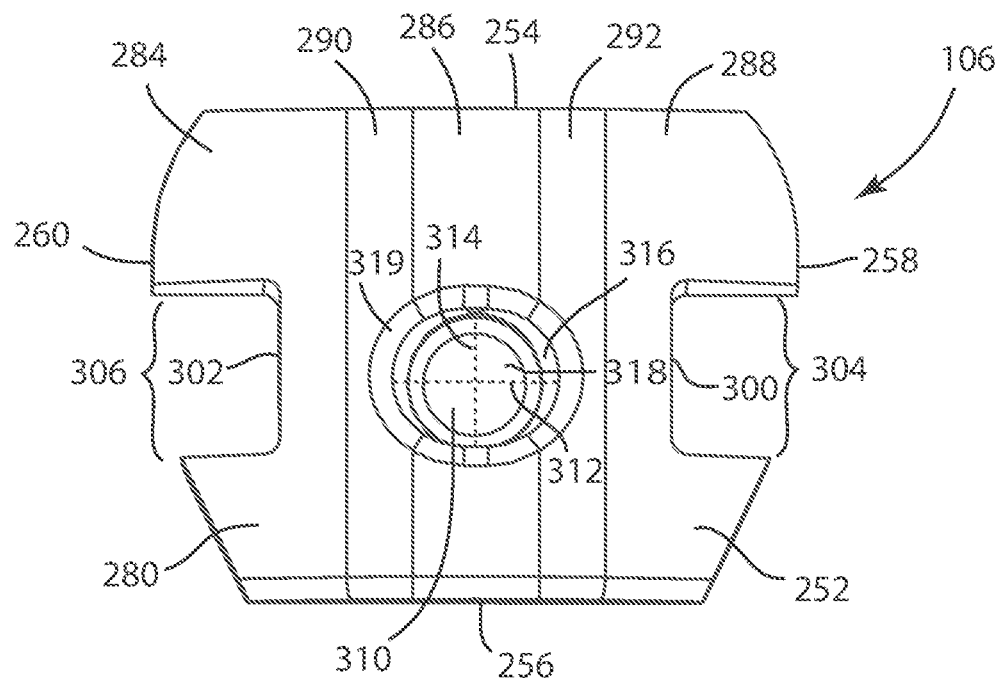
FIG. 5B illustrates a bottom view of the nucleus of FIG. 1.
Figure 6:
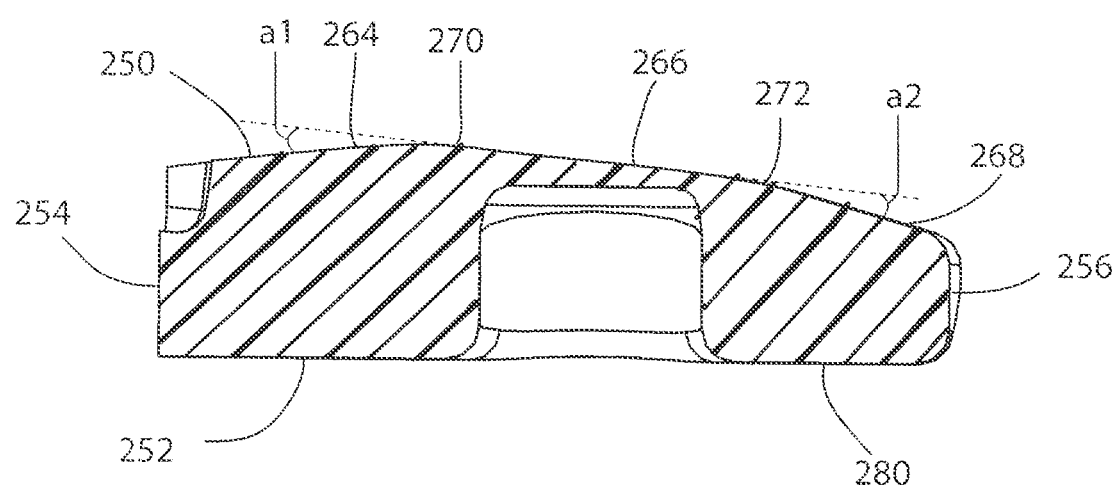
FIG. 6 illustrates a lateral cross-sectional view of the nucleus of FIG. 1.
Figure 7A:
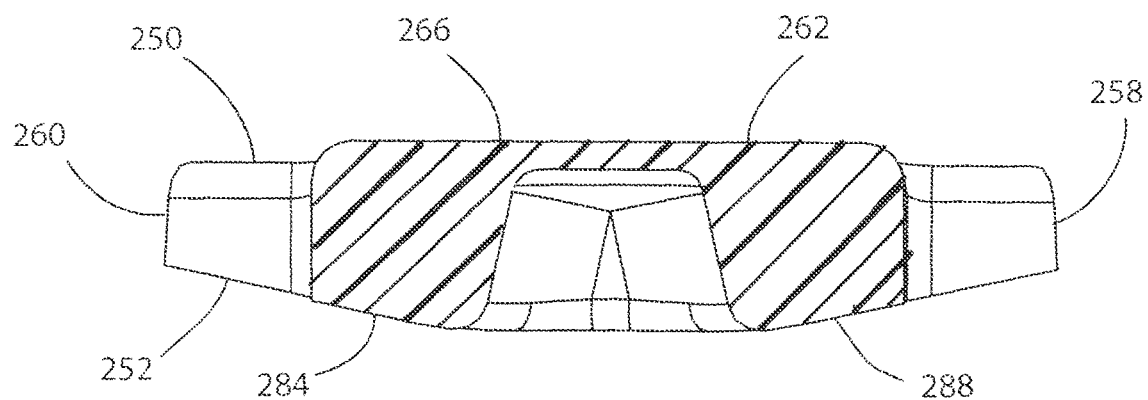
FIG. 7A illustrates a posterior cross-sectional view of the nucleus of FIG. 1.
Figure 7B:
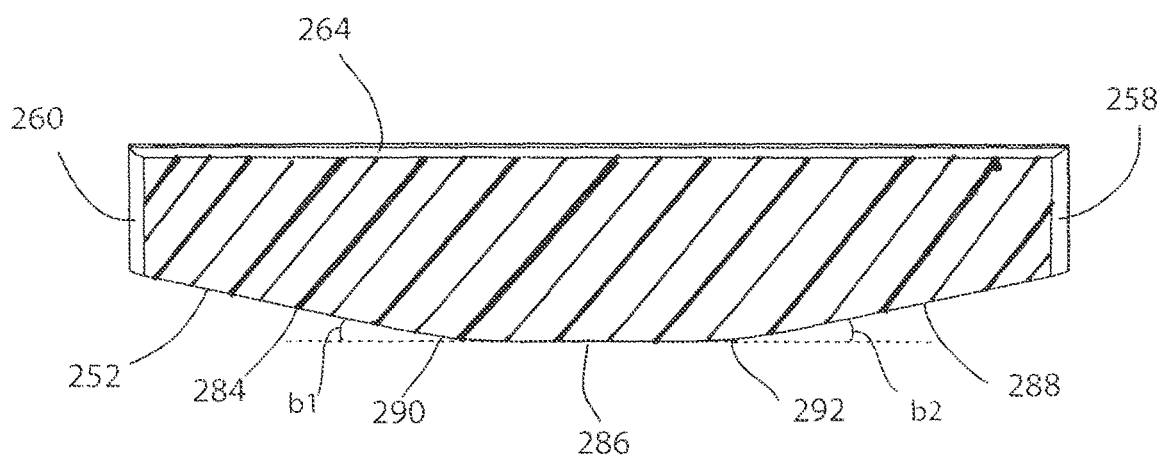
FIG. 7B illustrates a posterior cross-sectional view of the nucleus of FIG. 1.

Referring to FIG. 5B, a pocket 310 is formed as a recess into the inferior side 252 of the nucleus 106 and is shaped to receive the post 180. Pocket 310 is shaped as a tapered slot, with a medial-lateral maximum opening dimension 312 which is greater than an anterior-posterior maximum opening dimension 314. A support wall 316 which circumscribes the pocket 314 tapers outward from an end wall 318 of the pocket to its opening 319. The support wall 316 may articulate with the circumferential wall 182 of the post 180. The ovoid shape and sloping support wall permit the nucleus 106 and the superior end plate 102 freedom to move relative to the post 180 during lateral bending.

Prosthesis 100 comprises a combination of articular surfaces and motion stops which allow the flexion-extension rotational degree of freedom and anterior-posterior translation on a first joint and the lateral bending and axial rotation degrees of freedom on a second joint. The centers of rotation for each individual rotational degree of freedom may be shared, or each rotational degree of freedom may have a different center of rotation. The first joint comprises the interface 263 between the nuclear superior articulation surface 262 and the inferior articular surface 132 of the superior end plate 102. During flexion-extension, the nuclear superior articulation surface 262 articulates with the inferior articular surface 132. Flexion is limited when the anterior planar portion 264 contacts the inferior articular surface 132, and, conversely, extension is limited when the posterior planar portion 268 contacts the inferior articular surface 132. The first joint also permits anterior-posterior translation of the superior end plate 102 relative to the nucleus 106 and the inferior end plate 104.

The second joint comprises the interface 281 between the nuclear inferior articulation surface 280 and the superior articular surface 164 of the inferior end plate 104. During lateral bending, the nuclear inferior articulation surface 280 articulates with the superior articular surface 164. Left lateral bending motion is limited when the left planar portion 288 contacts the superior articular surface 164, and right lateral bending motion is limited when the right planar portion 284 contacts the superior articular surface 164. Axial rotation also occurs on the second joint, as the nuclear inferior articulation surface 280 rotates relative to the superior articular surface 164 around the axis of the post 180. This axial rotation motion may be limited by the angled inner edges of the anterior 170 and posterior 166 retention members on the inferior end plate 104.

Figure 9A:
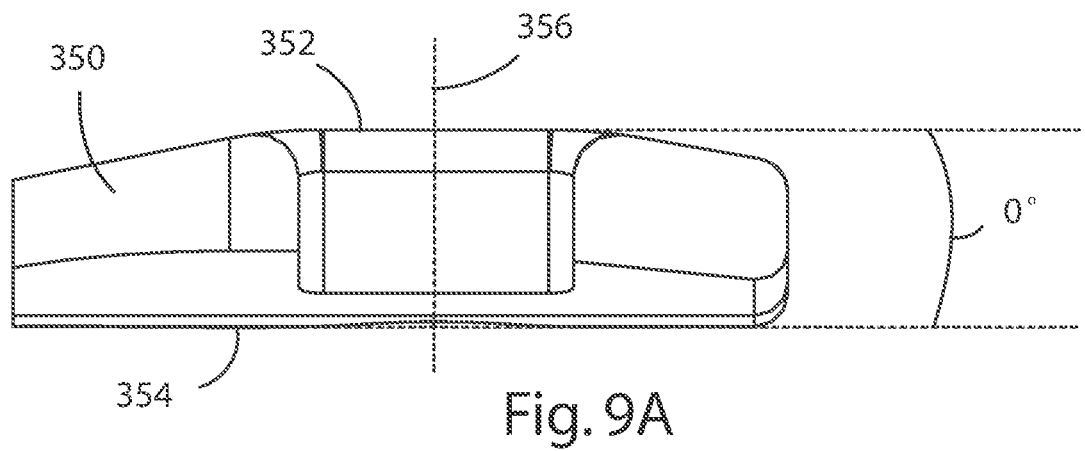
FIG. 9A illustrates a lateral view of an artificial disc nucleus that provides 0° of lordotic correction.
Figure 9B:
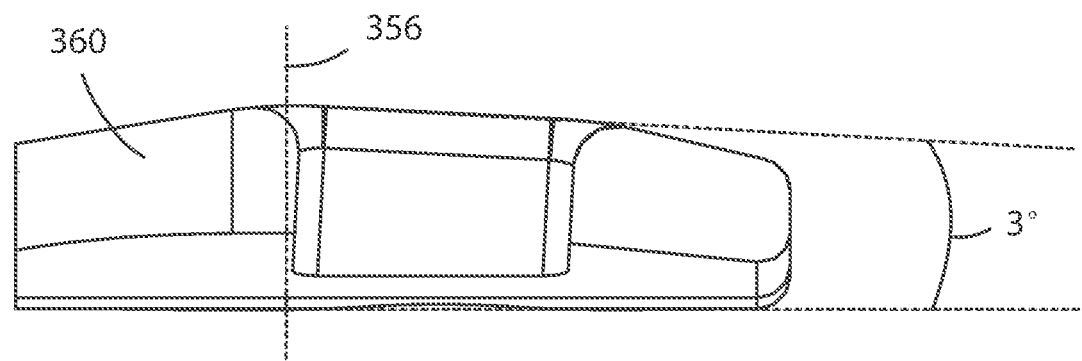
FIG. 9B illustrates a lateral view of an artificial disc nucleus that provides 3° of lordotic correction.
Figure 9C:
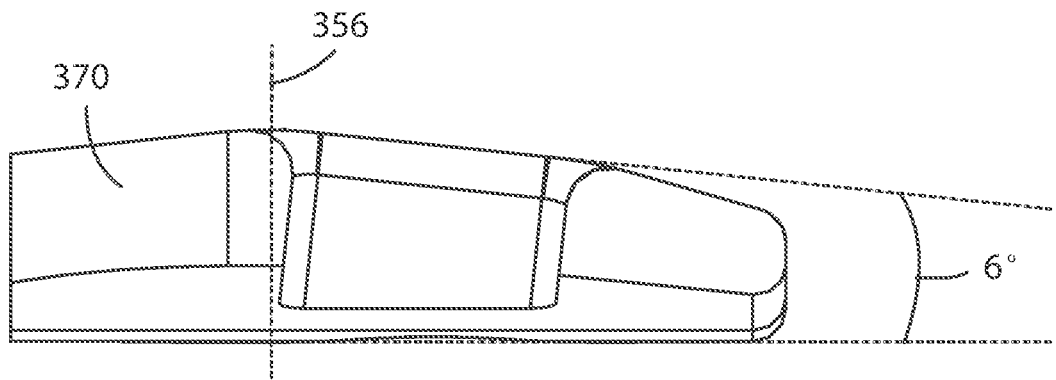
FIG. 9C illustrates a lateral view of an artificial disc nucleus that provides 6° of lordotic correction.

Referring to FIGS. 9A, 9B, and 9C, alternate embodiments of artificial disc nuclei are illustrated in lateral cross-sectional views. FIG. 9A illustrates a nucleus 350 in which the upper and lower surfaces 352 and 354 are parallel to each other and an angle between them is 0 degrees. In this nucleus, an axis of greatest height 356 falls in the center of the disc. In FIG. 9B, a nucleus 360 that provides 3° of lordotic correction is illustrated. FIG. 9C illustrates another artificial disc nucleus 370 having 6° of lordotic correction. When deformity correction is provided as shown in FIGS. 9B and 9C, the axis of greatest height 356 may shift to a location that is offset from the geometric center of the nucleus. If the anterior/posterior directions are reversed, a kyphotic correction is provided. It is apparent that the nucleus can be adjusted to provide various degrees of correction and, in certain cases, if no degree of correction is needed. Nuclei 350, 360, 370 may be combined with end plates 102, 104 or other end plates to form artificial disc prostheses. Nucleus 106 comprises 6° of lordotic correction.

Figure 10A:
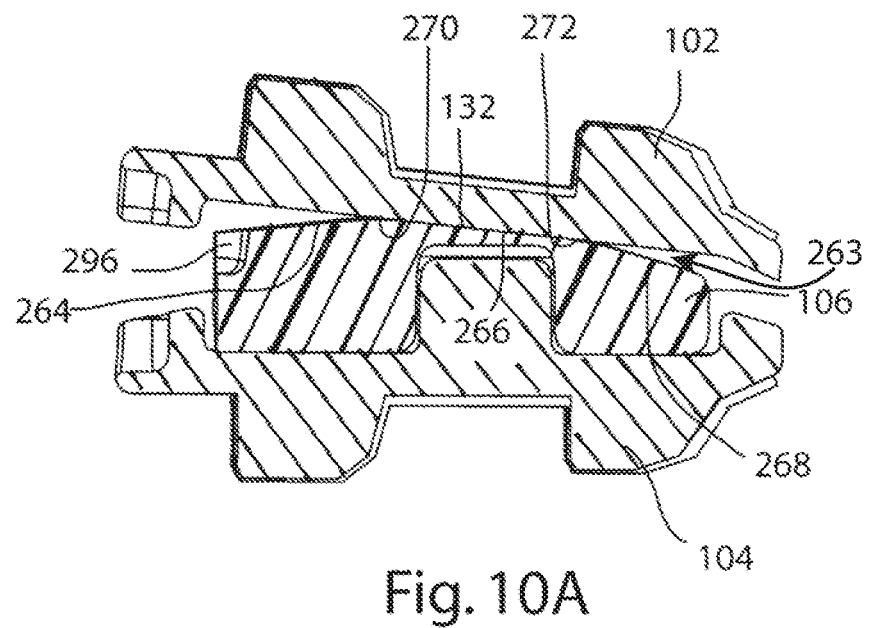
FIG. 10A illustrates a sagittal cross-sectional view of the artificial disc prosthesis of FIG. 1 in a preferred orientation in the flexion-extension degree of freedom.
Figure 10B:
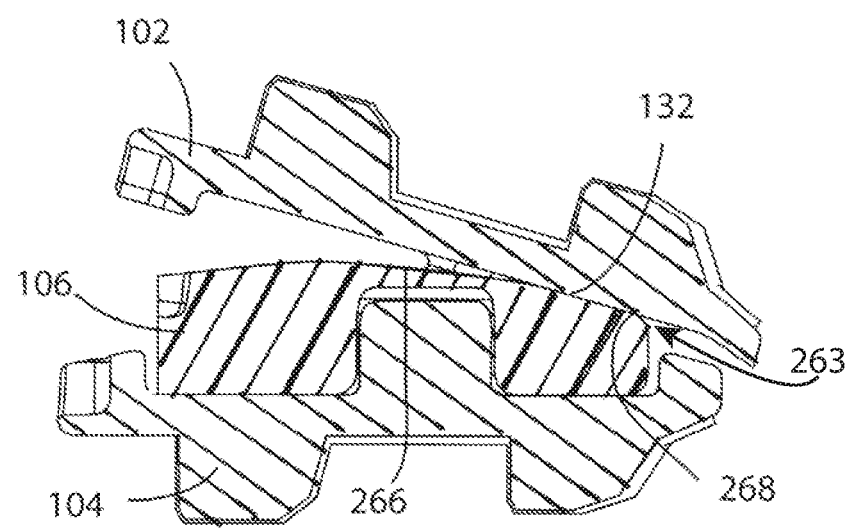
FIG. 10B illustrates a sagittal cross-sectional view of the artificial disc prosthesis of FIG. 1 in extension.

The middle planar portions on each nuclear articulation surface may provide each joint with a preferred orientation or stable low energy position. A low energy position is not the same as a motion limited position, from which motion of the joint in a particular direction is prohibited after a certain point, i.e. past a motion stop. Instead a low energy position is an orientation of a joint into which the joint tends to settle, and energy must be expended to move the joint out of to the low energy position. FIG. 10A is a sagittal cross-sectional view of prosthesis 100 with a joint between the superior end plate 102 and the nucleus 106 in a low energy position in the flexion-extension degree of freedom. Inferior articular surface 132 is in surface contact with middle planar portion 266, providing a preferred orientation and low energy position of the prosthesis across a coronal plane of the superior and inferior end plates 102, 104. In order for the joint to move out of the low energy position, sufficient energy will have to be applied to the superior end plate 102 to overcome resistance and rotate anteriorly across the coronal plane over the first curvate transition portion 270 in flexion or rotate posteriorly over the second curvate transition portion 272 in extension. FIG. 10B illustrates the prosthesis of 10A with the joint in extension. The superior end plate 102 is tilted back such that inferior articular surface 132 is in contact with posterior planar portion 268, the extension motion stop.

Figure 11A:
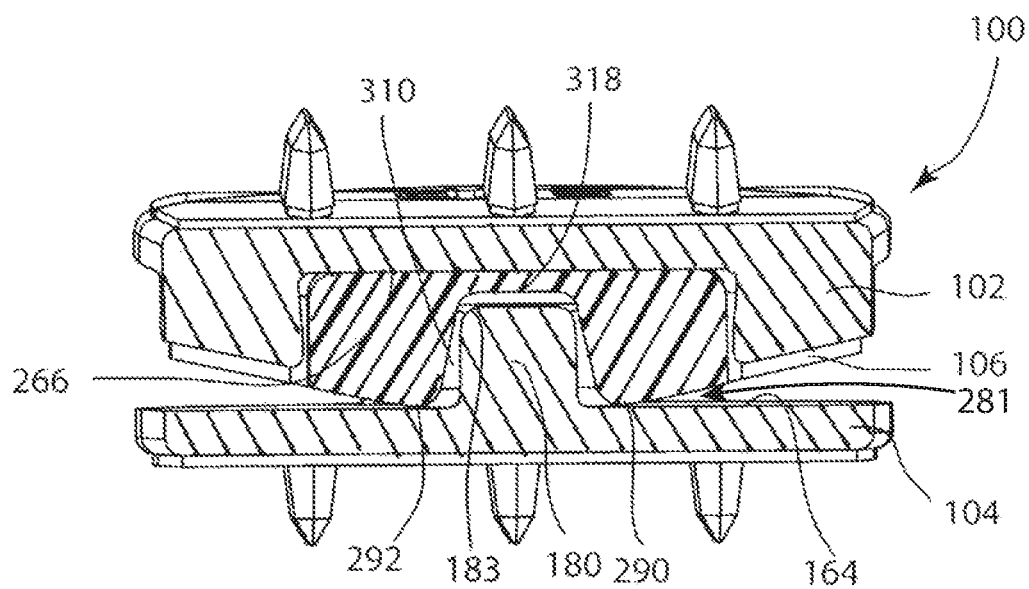
FIG. 11A illustrates a posterior cross-sectional view of the artificial disc prosthesis of FIG. 1 in a preferred orientation in the lateral bending degree of freedom.
Figure 11B:
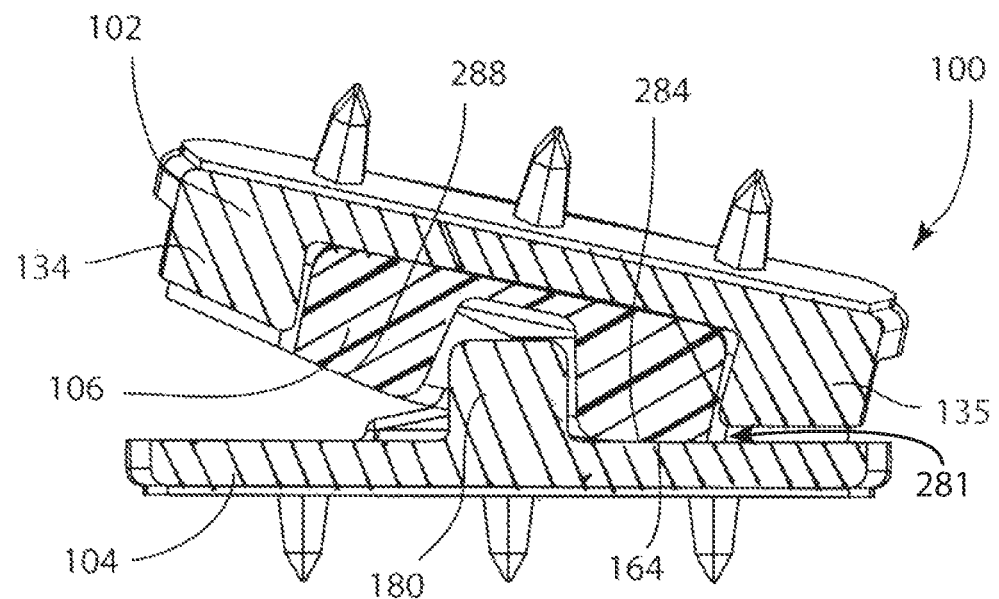
FIG. 11B illustrates a posterior cross-sectional view of the artificial disc prosthesis of FIG. 1 in lateral bending.
Figure 12A:
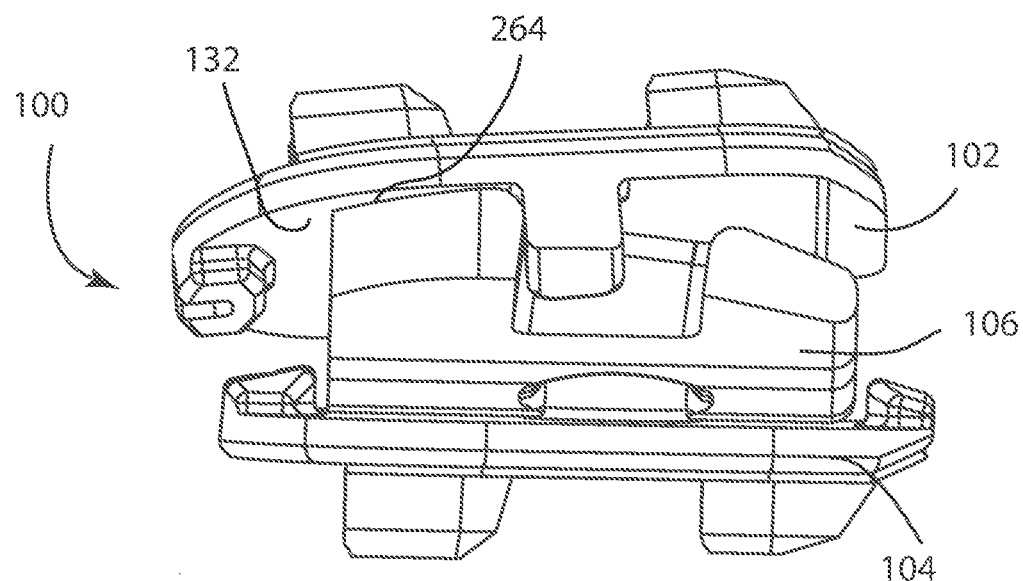
FIG. 12A illustrates a lateral view of the artificial disc prosthesis of FIG. 1 in flexion and lateral bending.
Figure 12B:
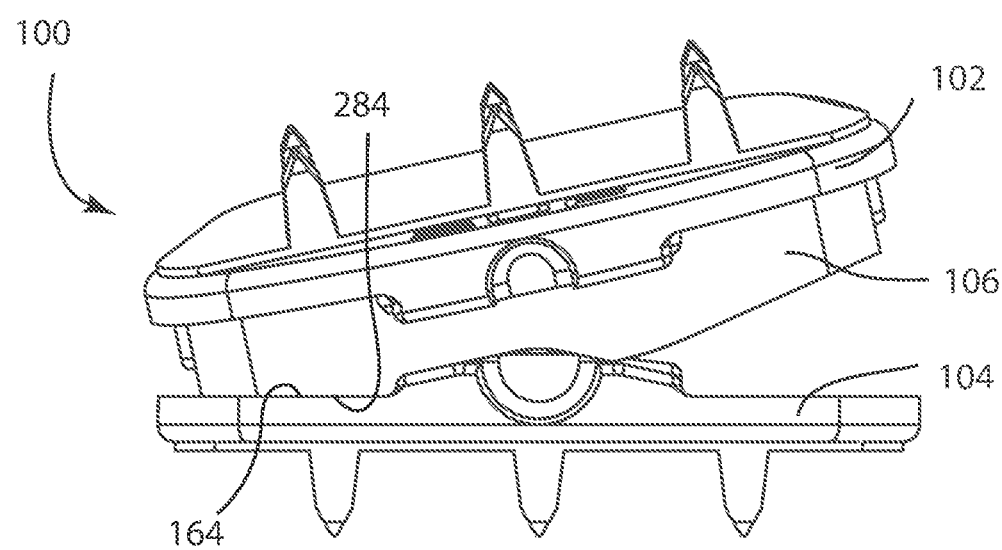
FIG. 12B illustrates an anterior view of the artificial disc prosthesis of FIG. 1 in flexion and lateral bending.

FIGS. 11A and 11B illustrate coronal cross-sectional views of prosthesis 100 from a posterior perspective, showing the prosthesis in a low energy position in the lateral bending degree of freedom, and in a laterally bent position, correspondingly. In FIG. 11A, the inferior articular surface of the nucleus is in a preferred orientation, in unbroken contact with the superior articular surface 164 of the inferior end plate 104 surrounding the post 180. In order for the prosthesis to move out of this preferred orientation, sufficient energy will have to be applied to laterally rotate the nucleus across the sagittal plane enough to lift one side out of contact with the superior articular surface 164. This position can be seen in FIG. 11B, at the lateral bending stop. FIGS. 12A and 12B illustrates the prosthesis 100 during flexion combined with lateral bending. FIG. 12A is a left lateral view, showing superior end plate 102 tilted forward in flexion, and also shifted forward in translation, and nucleus 106 is in right lateral bending. FIG. 12B is an anterior view, showing superior end plate 102 in flexion and anterior translation and nucleus 106 tilted right in lateral bending. In this position, anterior planar portion 264 of the nucleus is in contact with the inferior articular surface 132 of the superior end plate 102, providing a soft stop to flexion. Right planar portion 284 of the nucleus is in contact with the superior articular surface 164 of the inferior end plate 104, providing a soft stop to lateral bending.

Figure 13A:
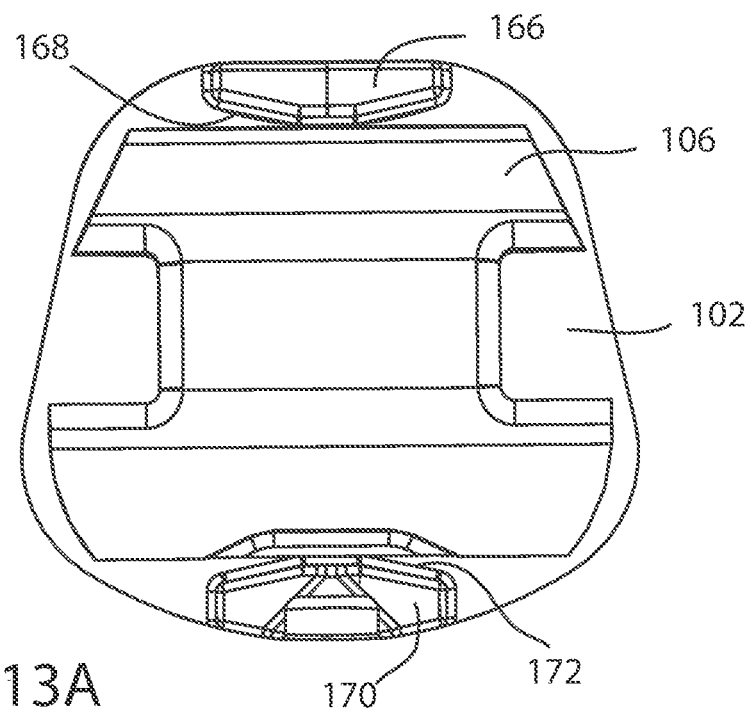
FIG. 13A illustrates a top view of the nucleus and inferior end plate of FIG. 1 in a neutral orientation with respect to rotation about a cephalad-caudal axis.
Figure 13B:
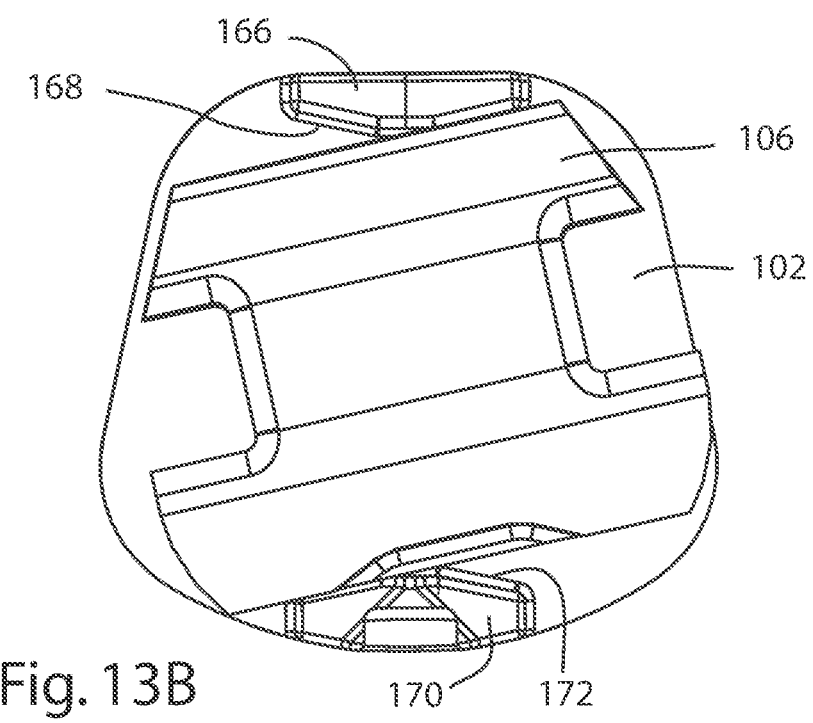
FIG. 13B illustrates the top view of the nucleus and inferior end plate of FIG. 1 in an axially rotated orientation.

FIGS. 13A and 13B illustrate axial rotation of the nucleus 106 relative to the inferior end plate 104. For clarity of illustration, superior end plate 102 is not shown. FIG. 13A illustrates nucleus 106 in a central, non-rotated position, and FIG. 13B shows the nucleus 106 rotated to the left. The angled inner edges 172, 168 of motion stops 170, 166 limit the rotational motion. Although not illustrated in these figures, it is appreciated that the present invention allows axial rotation to occur in combination with flexion-extension and/or lateral bending and/or anterior-posterior translation.

It is appreciated that other embodiments of the invention may swap or redistribute the combinations and/or locations of the rotational degrees of freedom. For example, one alternate embodiment may include flexion-extension and lateral bending in one joint and axial rotation in the other joint. Another embodiment may include flexion-extension and axial rotation in one joint, and lateral bending in the other joint.

Figure 14:
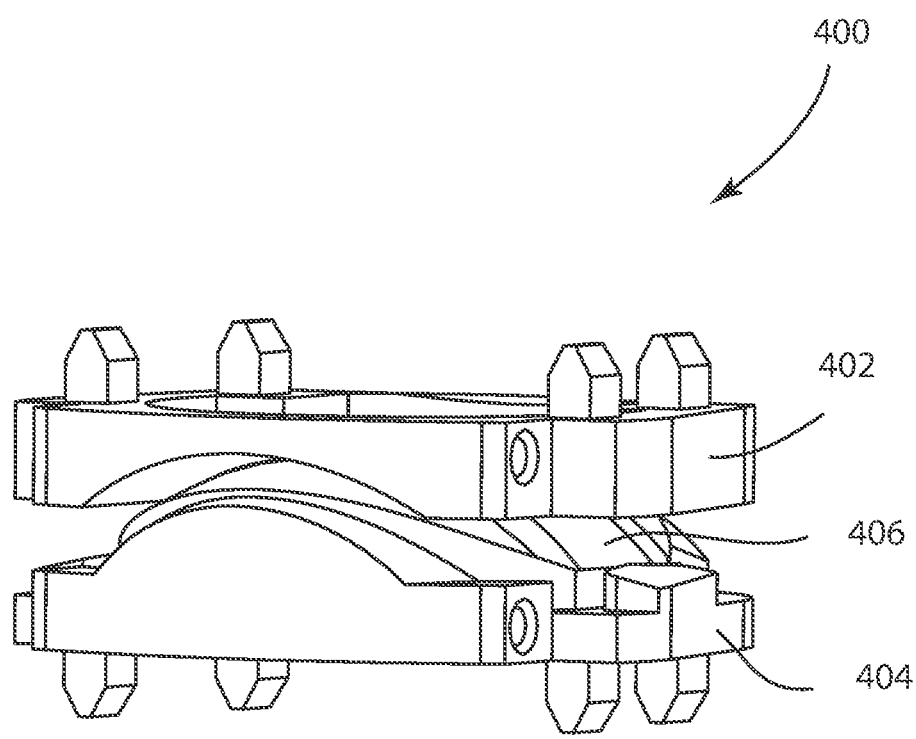
FIG. 14 illustrates an anterior perspective view of an alternative embodiment of an artificial disc prosthesis comprising a superior end plate, a nucleus, and an inferior end plate.

FIG. 14 illustrates an alternative embodiment of the invention, an artificial disc prosthesis 400 comprising a superior end plate 402, an inferior end plate 404, and a core, or nucleus 406. The superior end plate comprises a superior surface adapted for bony contact and an at least partially cylindrical surface on an inferior surface to articulate a superior surface of the nucleus. The nucleus includes an at least partially cylindrical superior surface and a planar inferior surface and a cylindrical outer surface. The inferior end plate comprises a planar superior surface which articulates with the inferior surface of the nucleus, and an inferior surface that is adapted for bony contact and a cylindrical inner surface. A first joint of the prosthesis allows flexion-extension and lateral bending degrees of freedom, and a second joint allows the axial rotation degree of freedom.

Figure 15:
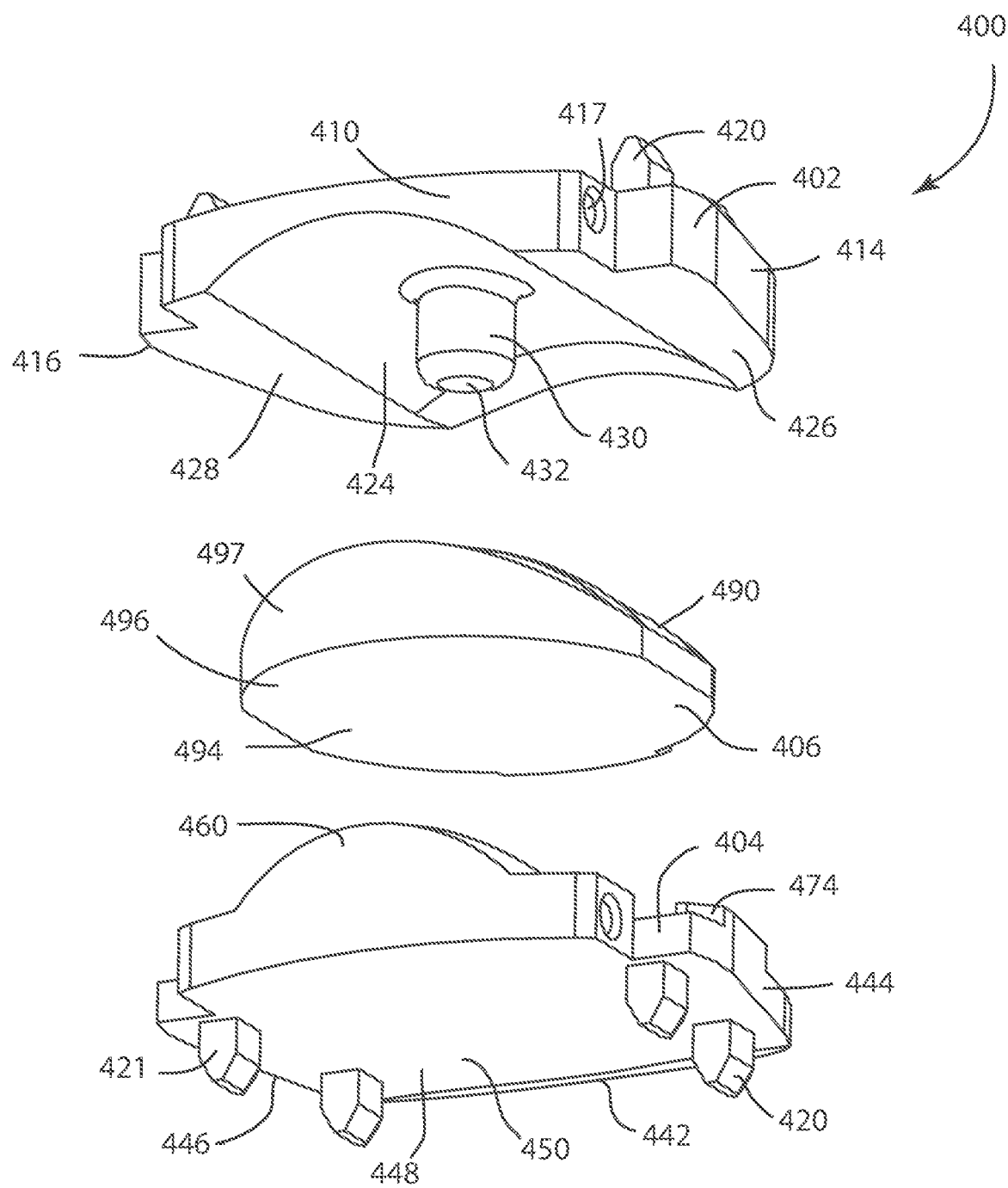
FIG. 15 illustrates an exploded bottom perspective view of the superior end plate, nucleus, and inferior end plate of FIG. 14.
Figure 16:
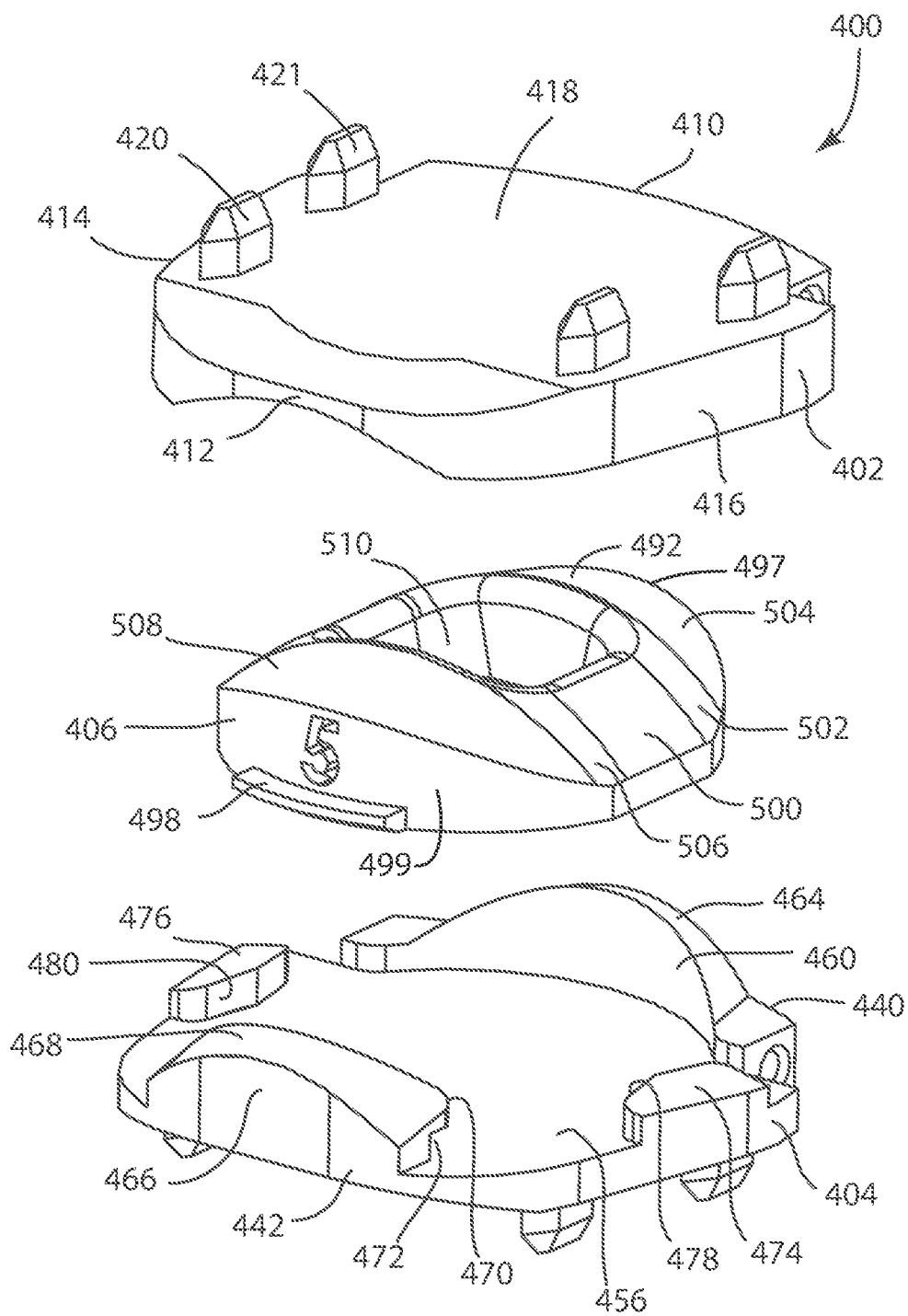
FIG. 16 illustrates an exploded top perspective view of the superior end plate, nucleus, and inferior end plate of FIG. 14.

FIG. 15 illustrates an exploded view of prosthesis 400 from an anterior-inferior perspective, and FIG. 16 illustrates an exploded view of the prosthesis from a posterior-superior perspective. Superior end plate 402 comprises an anterior end 410, a posterior end 412, a left lateral side 414 and a right lateral side 416. A gripping recess 417 may be located on either or both lateral sides. A superior bone engagement surface 418 is adapted for bony contact, and a plurality of self-cutting teeth 420 and/or 421 may be distributed on the bone engagement surface 418. Both the bone engagement surface and the teeth may incorporate bone ingrowth or ongrowth treatments as previously set forth. An inferior articular surface 424 comprises a flattened portion shaped as a partial cylinder. A post 430 extends caudally from the inferior articular surface, comprising post articular surface 432 which may incorporate a flattened section portion. Flattened lateral portions 426, 428, which may be planar, flank the inferior articular surface 424.

Inferior end plate 404 comprises an anterior end 440, a posterior end 442, a left lateral side 444 and a right lateral side 446. Gripping recesses 417 may be located on the lateral sides. An inferior bone engagement surface 450, which may be planar, is on an inferior side 448, and may comprise a plurality of self-cutting teeth 420, 421. The teeth and bone engagement surface may comprise areas incorporating bone ingrowth or bone ongrowth treatments. Referring to FIG. 16, a planar superior articular surface 456 is on a superior side 452 of the end plate. An anterior motion stop 460 extends along the anterior end 440 and cephalad toward the superior end plate 402. An inner surface 462 is cylindrical to correspond with a cylindrical outer edge of the nucleus 406, and an upper surface 464 is shaped as a portion of a cylinder to mate with the inferior articular surface 424 of the superior end plate 402 during flexion. A posterior motion stop 466 similarly comprises a cylindrical upper surface 468 to mate with the inferior articular surface 424 during extension. The posterior motion stop 466 further comprises a cylindrical inner surface 470, and an undercut 472 which is shaped to receive a tab on the nucleus 406. Right and left lateral motion stops 474, 476, comprising angled upper surfaces extend toward the superior end plate 402. Dovetailed inner surface 478, 480 on the right 474 and left 476 stops allow limited axial rotation of the nucleus relative to the inferior end plate 404.

The nucleus 406 comprises a superior side 490 with a partially cylindrical superior articular surface 492, and an inferior side 494 with a planar inferior articular surface 496. An anterior end 497 is cylindrical to correspond with the anterior motion stop 460 of the inferior end plate 404. A cylindrical posterior end 499 comprises a tab 498 shaped to fit in the undercut 472 on the inferior end plate 404. The tab 498 operates to resist posterior migration (i.e., expulsion) of the nucleus toward the spinal canal by preventing "lift off" of the nucleus from the inferior end plate and possible dislocation of the nucleus. As shown, the tab 498 can be rounded, chamfered or beveled in order to facilitate initial insertion and intra-operative or post-operative replacement of the nucleus.

The superior articular surface 492 comprises three flattened sections, each of which is shaped as a portion of a cylinder. Central flattened section 500 extends medial-laterally across the nucleus, crossing a sagittal plane of the prosthesis. A first curvate transition portion 502 lies between the central section 500 and an anterior flattened portion 504, while a second curvate transition portion 506 lies between the central section 500 and a posterior flattened portion 508. A generally centrally located pocket 510 extends caudally into the nucleus and may be configured to be larger than the post both medial-laterally and antero-posteriorly, to allow limited translation of the superior end plate 402 during flexion-extension and lateral bending. In an alternative embodiment of the invention, the pocket 510 may be smaller so that it contacts the post 430 to form motions stops for flexion/extension and/or lateral bending. Another alternative embodiment may comprise a two-piece prosthesis wherein the nucleus 406 is joined with the inferior end plate 404, and superior articular surface 492 articulates with inferior articular surface 424 of superior end plate 402.

Figure 17A:
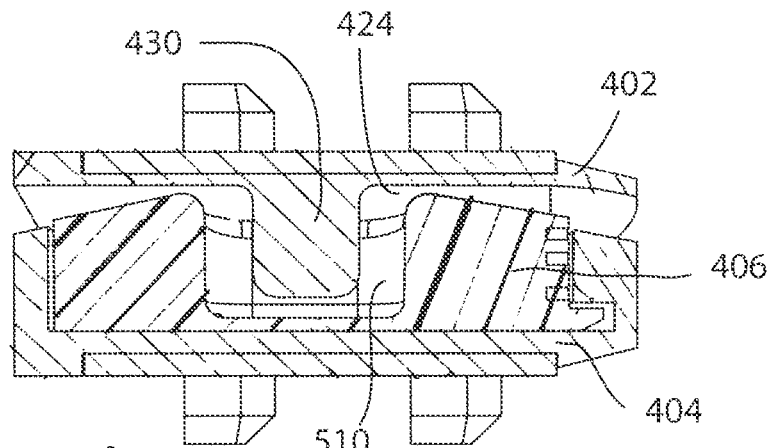
FIG. 17A illustrates a sagittal cross-sectional view of the artificial disc prosthesis of FIG. 14 in a neutral low-energy orientation with respect to the flexion-extension degree of freedom.
Figure 17B:
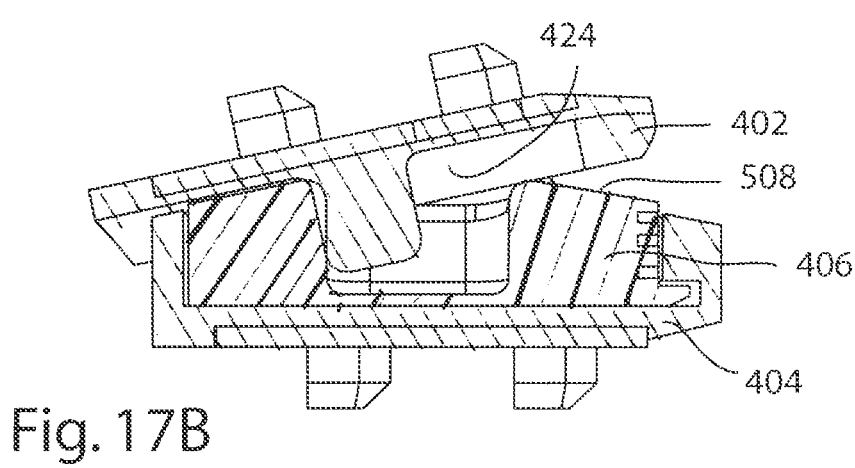
FIG. 17B illustrates a sagittal cross-sectional view of the artificial disc prosthesis of FIG. 14 in flexion.
Figure 17C:
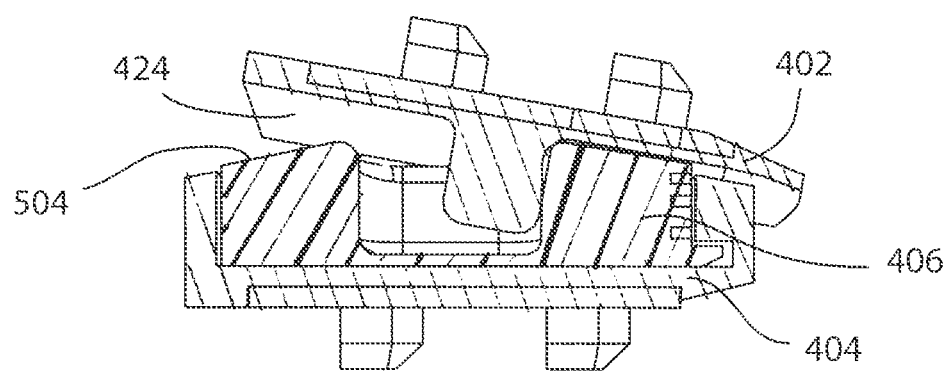
FIG. 17C illustrates a sagittal cross-sectional view of the artificial disc prosthesis of FIG. 14 in extension.

FIG. 17A illustrates a sagittal cross-sectional view of prosthesis 400 in a preferred orientation position, FIG. 17B illustrates the prosthesis in flexion, and FIG. 17C illustrates the prosthesis in extension.

Figure 18:
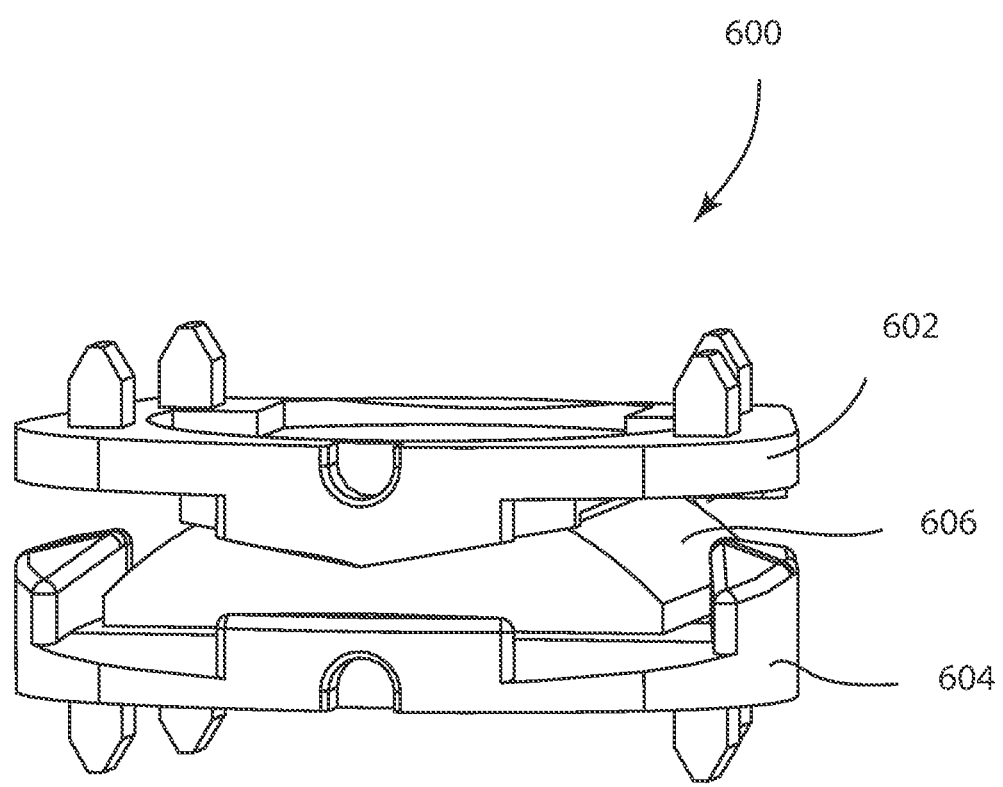
FIG. 18 illustrates an anterior perspective view of an alternative artificial disc prosthesis comprising a superior end plate, a nucleus, a retention element, and an inferior end plate.
Figure 19:
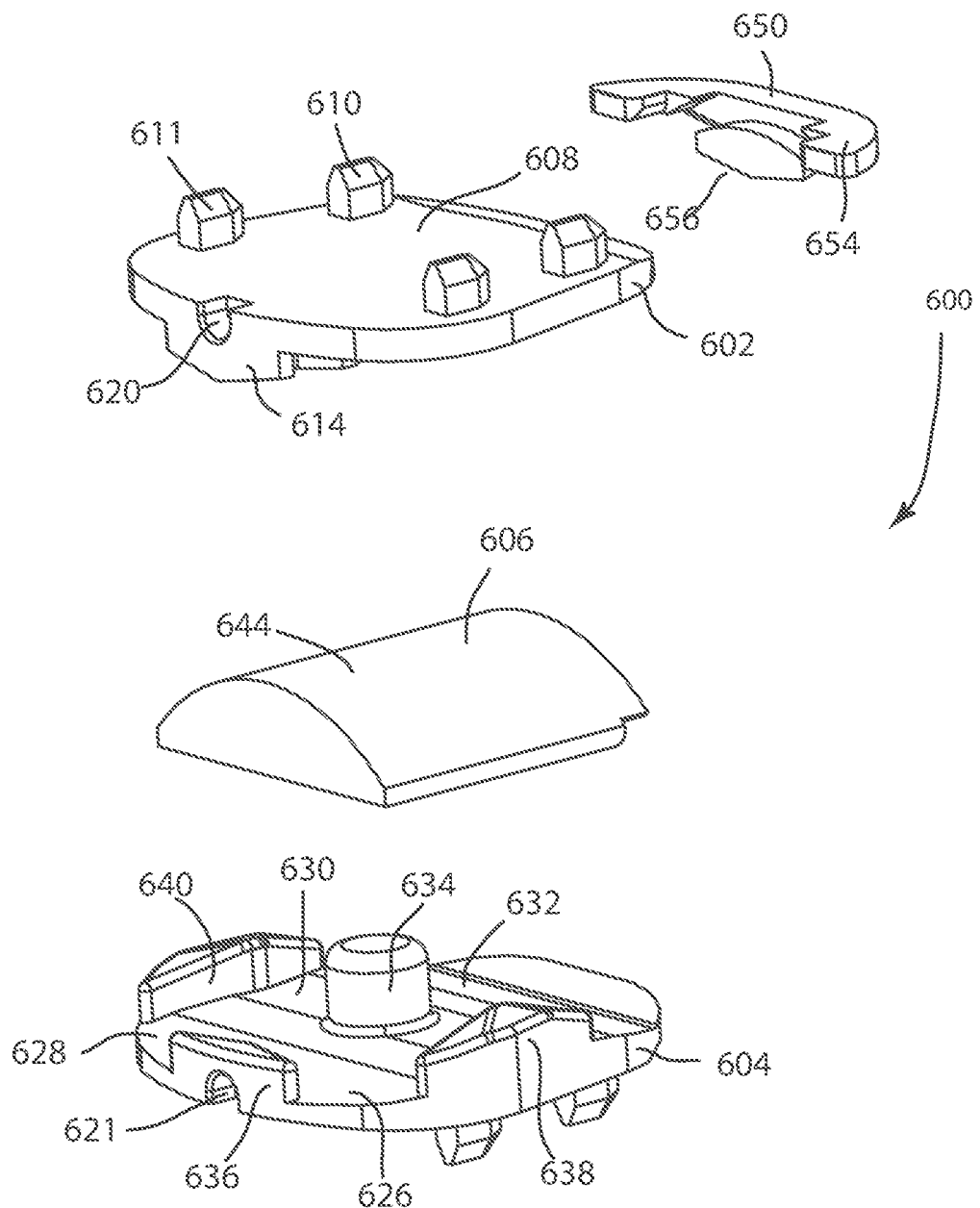
FIG. 19 illustrates an exploded top perspective view of the superior end plate, nucleus, retention element, and inferior end plate of FIG. 18.
Figure 20:
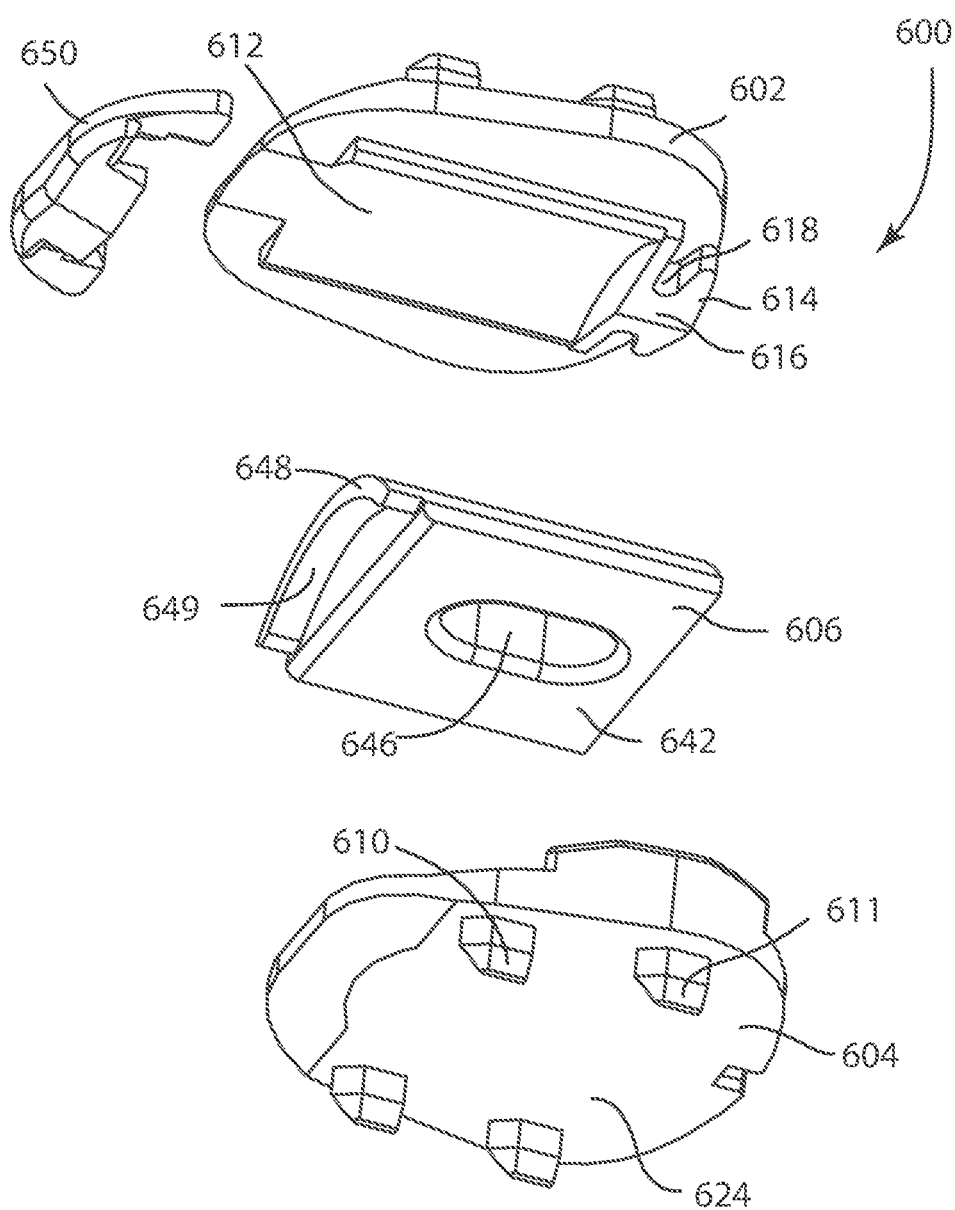
FIG. 20 illustrates an exploded bottom perspective view of the superior end plate, nucleus, retention element, and inferior end plate of FIG. 18.

FIGS. 18-20 illustrate another alternate embodiment of the invention, an artificial disc prosthesis 600. Prosthesis 600 permits the lateral bending degree of freedom on a first upper joint, and the flexion-extension and axial rotation degrees of freedom on a second lower joint. The prosthesis comprises a superior end plate 602, and inferior end plate 604, and a core or nucleus 606 which is positioned between and articulates with the end plates.

FIG. 19 illustrates an exploded view of prosthesis 600 from a superior perspective, and FIG. 20 illustrates an exploded view from an inferior lateral perspective. Superior end plate 602 comprises a planar bone engagement surface 608, and a plurality of self-cutting teeth 610, 611 may be formed on the bone engagement surface. On an inferior side of the end plate 602 is formed a partially cylindrical inferior articular surface 612. An anterior retention member 614 is formed on an anterior end and has an angled surface 616 which is angled medial-laterally to permit lateral bending during flexion. Gripping slots 618 are formed behind the retention member 614 as gripping features for instruments during implantation, revision and/or removal of the prosthesis. A pocket 620 is formed into the anterior portion of the retention member 614 and serves as a receptacle for instrumentation. A posterior end of the end plate 602 may be slightly angled to assist in insertion into the intervertebral space.

Inferior end plate 604 comprises a planar bone engagement surface 624 upon which may be formed a plurality of self-cutting teeth 610, 611. Similar to the superior end plate 602, a posterior end of the end plate may be slightly angled, so that during insertion into the intervertebral space the posterior ends of the end plates form a reduced cephalad-caudal profile. A superior side of the inferior end plate 604 comprises a superior articular surface 626, which in turn comprises three flattened portions separated by curvate transition portions. The flattened portions, anterior planar portion 628, middle planar portion 630, and posterior planar portion 632 are not co-planar with respect to one another and are perpendicular to a sagittal plane of the vertebral bodies when prosthesis 600 is properly implanted in an intervertebral space. Middle planar portion 630 cooperates with a planar inferior surface of the nucleus to provide a neutral low energy position or preferred orientation of the prosthesis in the flexion-extension degree of freedom. The anterior planar portion 628 forms a soft motion stop when it contacts the planar inferior surface of the nucleus during flexion, and the posterior planar portion 632 forms a soft motion stop when it contacts the planar inferior surface of the nucleus during extension. A post 634 protrudes from the superior articular surface 626 and cooperates with a pocket in the nucleus to permit anterior-posterior translation during flexion-extension. An anterior retention member 636 protrudes from the end plate 604 toward the opposite end plate 602, and a pocket 621 is formed in the anterior end of the end plate inferior to the anterior retention member. Left 638 and right 640 lateral motion stops are formed on the lateral edges of the end plate. Each of the left and right lateral motions stops includes a tri-sloped upper surface, to permit flexion-extension during lateral bending, and vice versa. Inside edges of the anterior 636, left 638 and right 640 motion stops are also angled to permit axial rotation of the nucleus about the axis of the post 634. Alternative embodiments of the inferior end plate 604 may incorporate a lordotic or kyphotic correction such that a maximum vertical axis of the end plate is displaced anteriorly or posteriorly from the center of the end plate.

The nucleus comprises a planar inferior articular surface 642 and a semi-cylindrical superior articular surface 644. The planar inferior articular surface 642 articulates with the superior articular surface 626 of the inferior endplate to provide flexion-extension and axial rotation, and the superior articular surface 644 articulates with the inferior articular surface 612 of the superior end plate 602 to provide lateral bending. An elongated pocket 646 is recessed into the inferior side of the nucleus and is shaped to receive the post 634. A curved tab 648 projects posteriorly from the nucleus with an undercut 649 formed under the tab.

A separately formed retention element 650 which is joined to the superior end plate 602 by welding or other means may engage with the nucleus 606 to retain the nucleus 606 in the prosthesis and also to serve as a motion stop. The retention element 650 comprises a body 652, a pair of arms 654 and a projection 656. The projection 656 fits into the undercut 649 on the nucleus, and the arms 654 fit over the curved tab 648. During spinal motion, the retention element moves with the superior end plate. The inferior surfaces of the body 652 and projection 656 are angled to allow both lateral bending and extension.

The intervertebral disc implants depicted in FIGS. 1-20 may be formed of biocompatible materials such as biocompatible metals or other suitable strong materials. An implant may be formed of one biocompatible material while the bearing surface comprises another biocompatible material. The implants may be constructed in a variety of footprint sizes, and a variety of shapes, to fit the variations found in patient vertebral sizes and vertebral shapes. Specifically, each implant may be available in three footprint sizes: small, medium, and large, and in three corrective lordotic angles: 0°, 3°, and 6°.

The implant components may be formed wholly or partially of any biocompatible metal, such as stainless steel, Titanium, Titanium alloys, Cobalt Chrome, CCM (Cobalt Chrome Molybdenum), Aluminum, Zirconium, Nickel Titanium (NiTi/Nitinol), shape memory metals, superelastic metals, metal matrix composites such as Titanium Carbide, Tungsten Carbide, Tantalum, or Chromium, among others. The implant components can be formed wholly or partially of a biocompatible ceramic material such as alumina, zirconia, alumina-zirconia blends, or other ceramic composites. The implant components can be formed wholly or partially of a biocompatible polymer such as PEEK, carbon or glass-fiber reinforced polymers, ABS, polycarbonate, polyethylenes, ultra high molecular weight polyethylene (UHMWPE), nylons, polymer composites, polyurethane, polycarbonate-polyurethane composites, acetals, polyesters, polypropylene, PTFE, ePTFE, absorbable polymers such as poly 1-lactic acid (PLLA), polylactic acid (PLA), polyglycolic acid (PGA), TCP, glycolides, lactides, hydrogels, elastomers such as silicone, nitrile, butyl, thermoplastic elastomers (TPE's), or ethylene vinyl acetate (EVA), among others.

The implant components can be can be formed wholly or partially of another biocompatible material including diamond or diamond-like materials, carbon, hyrdogels, pyrocarbon, pyrolitic carbon, allograft bone, demineralized bone, collagen, cartilage, tricalcium phosphate, calcium phosphate, hydroxyapatite, PMMA—bone cement, proteins, amino acids, nucleic acids, or sugars, among others.

The implant components may also be coated wholly or partially with specialized coatings such as Titanium Nitride, Titanium Boride, Titanium Carbide, ion-based coatings, ceramic coatings, oxide coatings, plasma, PTFE coatings, low-friction coatings, hydrophobic or hydrophilic coatings, or vapor deposition coatings, among others. Bone-contacting portions of implant components may comprise porous or non-porous bone ingrowth surfaces.

In another aspect of the invention, all of the articulating surfaces of the prosthesis can be formed of a polymer. As discussed above, the nucleus can be formed entirely of a polymer such as, for example, ultra-high molecular weight polyethylene ("UHMWPE"), a cross, linked UHMWPE, a ceramic, polyetheretherketone ("PEEK") or other type of suitable polymer. The bony ingrowth surfaces can be made from plasma sprayed metals, hydroxyapatite or similar bone-like coatings, and can include a coating of bone growth factors. The articulating surfaces of the end plates can be formed with inserts of an appropriate polymer, ceramic or the like. The remaining exterior surfaces of the end plates that interface with bone can be formed with bony ingrowth surfaces of the type discussed above.

Figure 21:
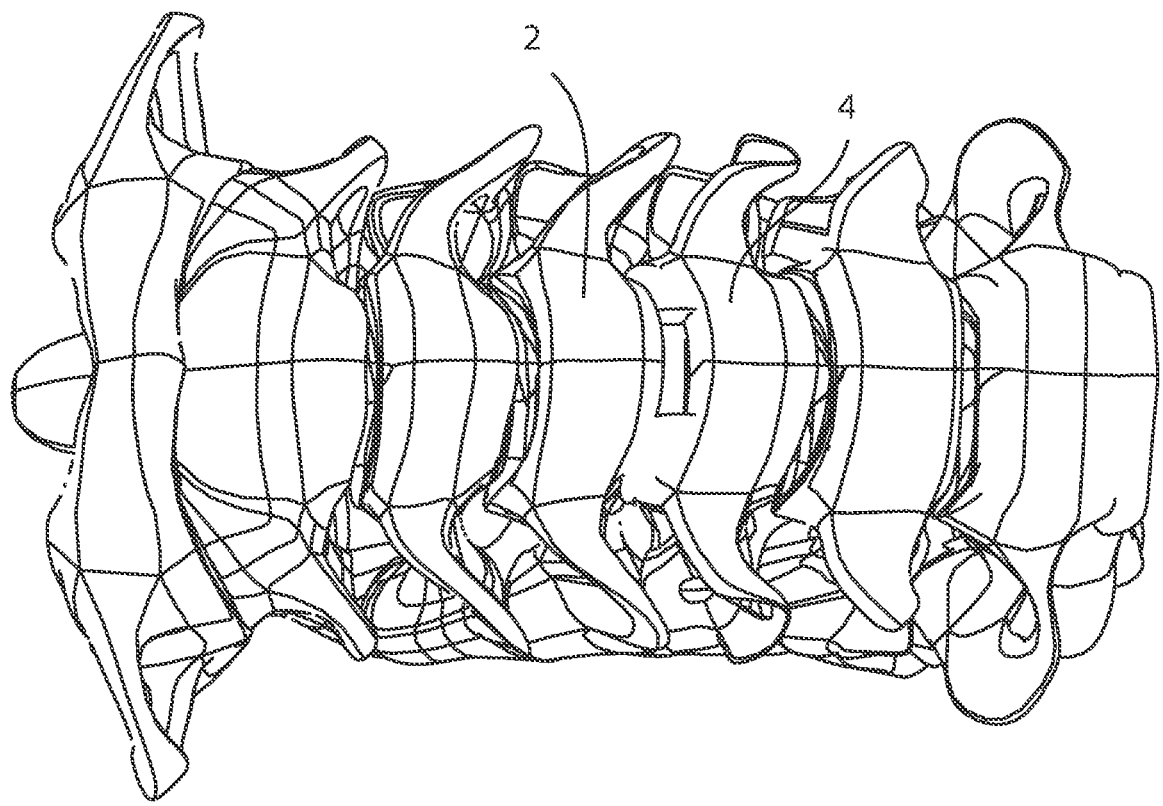
FIG. 21 illustrates a portion of a spine with a partial discectomy between two cervical vertebrae.

FIGS. 21-41 illustrate instrumentation and methods for implanting an artificial disc prosthesis such as prosthesis 100 into a portion of a spine. A kit of tools, including implant trials in a variety of sizes, may be provided. Referring to FIG. 21, the patient is prepared in a neutral posture position, and the target disc level of the spine is exposed from an anterior approach. A partial discectomy is conducted in a targeted intradiscal space between superior vertebral body 2 and inferior vertebral body 4. Although cervical vertebral bodies 2 and 4 are depicted in the illustrations as the C4 and C5 level vertebrae, it is appreciated that the procedure could be performed on other vertebral pairs in the spine.

Figure 22:
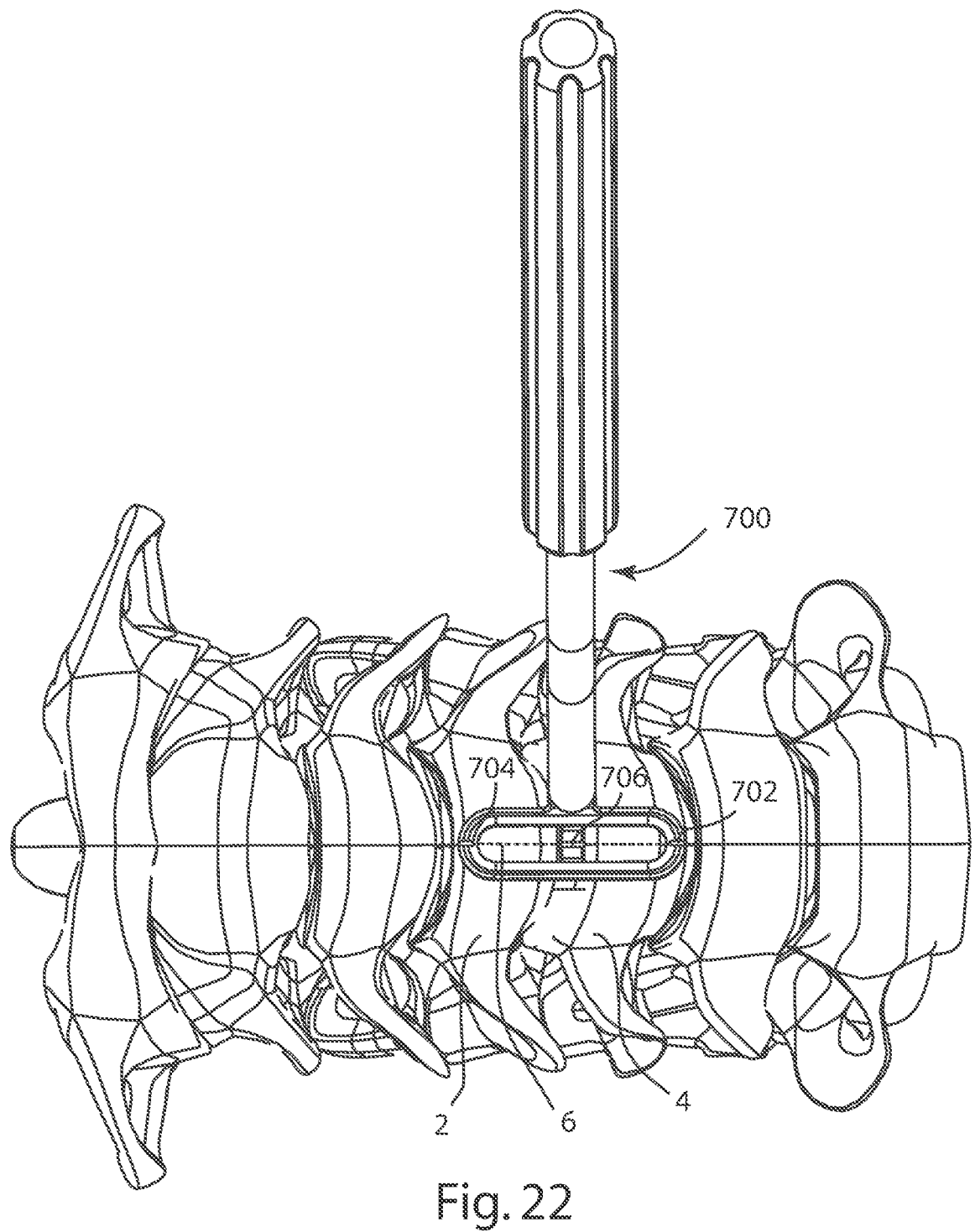
FIG. 22 illustrates a guide tool aligned with the midline of the portion of the spine of FIG. 21.
Figure 23:
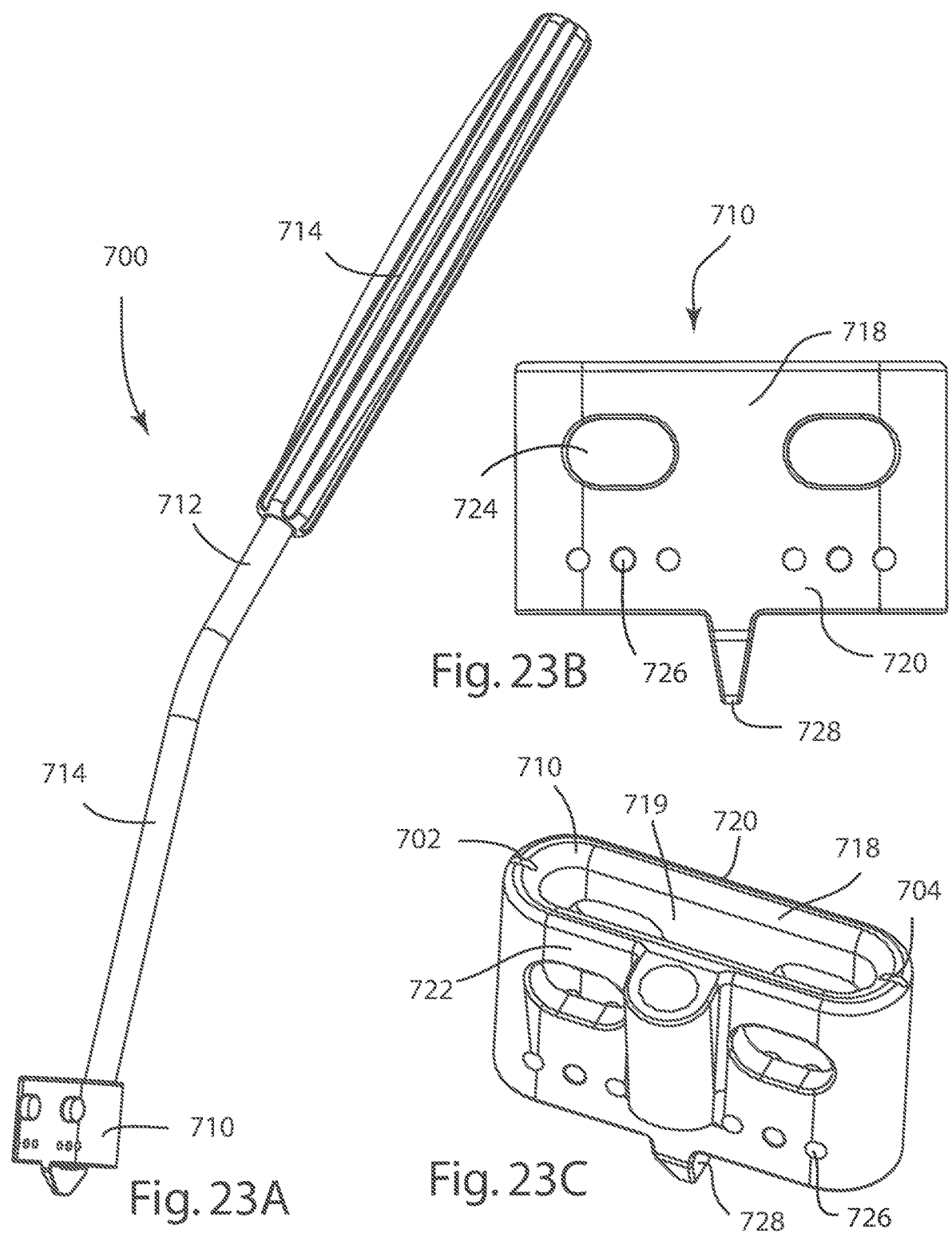
FIG. 23A illustrates a perspective view of the guide tool of FIG. 22.
FIG. 23B illustrates a lateral view of a head of the guide tool of FIG. 22.
FIG. 23C illustrates a perspective lateral view of the head.

Referring to FIG. 22, a sagittal midline 6, or central midline axis of the vertebral bodies is determined and may be marked on the exposed vertebral bodies. A guide tool 700 is preliminarily positioned on the vertebral bodies, aligning sagittal indicators 702, 704, 706 with the sagittal midline 6 when viewed from a viewpoint normal to the coronal plane. Alternatively, a line may be determined which is not on the sagittal midline but is parallel to the sagittal midline, and the guide may be aligned to this offset line instead.

FIG. 23A illustrates guide tool 700 in its entirety, FIG. 23B illustrates an enlarged side view of a guide head 710, and FIG. 23C illustrates an enlarged perspective view of the guide head. Guide tool 700 comprises a handle 712 which comprises a proximal gripping portion 714 and a distal shaft portion 716. The shaft 716 is welded to the head 710. The guide head 710 is shaped as an elongated loop and comprises a circumferential wall 718 which defines a guide lumen 719. The head 710 has a first side 720 and a parallel second side 722, through which ports 724 and lateral alignment holes 726 open. A guide tab 728, which includes the sagittal indicator 706, protrudes distally and is connected to both first 720 and second 722 sides. As seen in FIG. 22, the guide tool 700 may be first positioned such that the guide tab 728 protrudes into the space created by the partial discectomy and the sagittal indicators are lined up with the sagittal midline 6. The guide tool 700 is further manipulated so that the lateral alignment holes 726 on side 720 align with the lateral alignment holes 726 on side 722, appearing concentric with one another when viewed from a viewpoint normal to the sagittal midline. In this way, the guide head is accurately positioned relative to three orthogonal planes, in a preferred orientation parallel to the sagittal plane and perpendicular to the coronal plane of the vertebral bodies. Fluoroscopy may be used to determine and direct the alignment processes. Another embodiment of the invention may comprise a single lateral alignment hole 726 on each side 720, 722.

Figure 24:
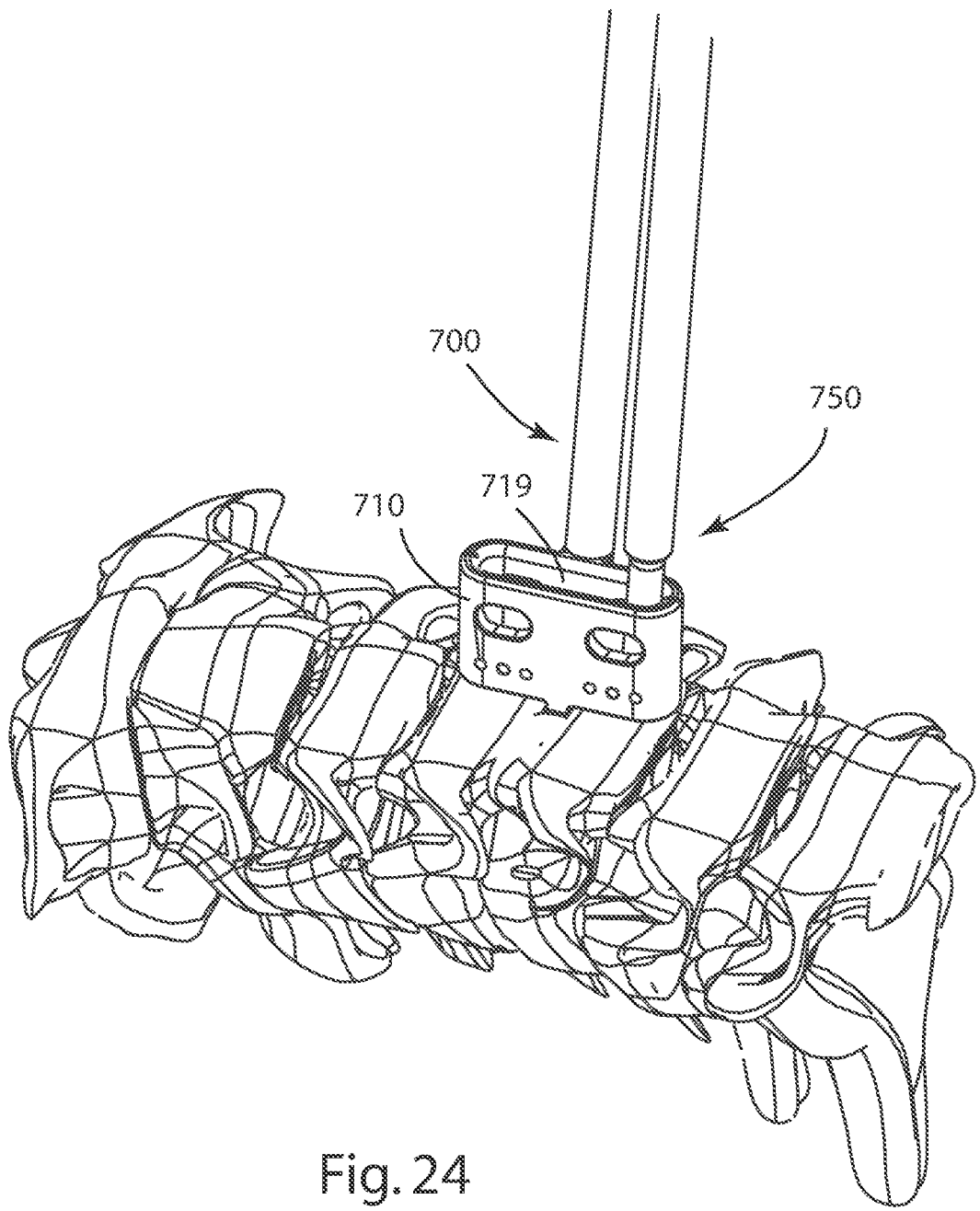
FIG. 24 illustrates an awl inserted through the guide tool of FIG. 22.
Figure 25:
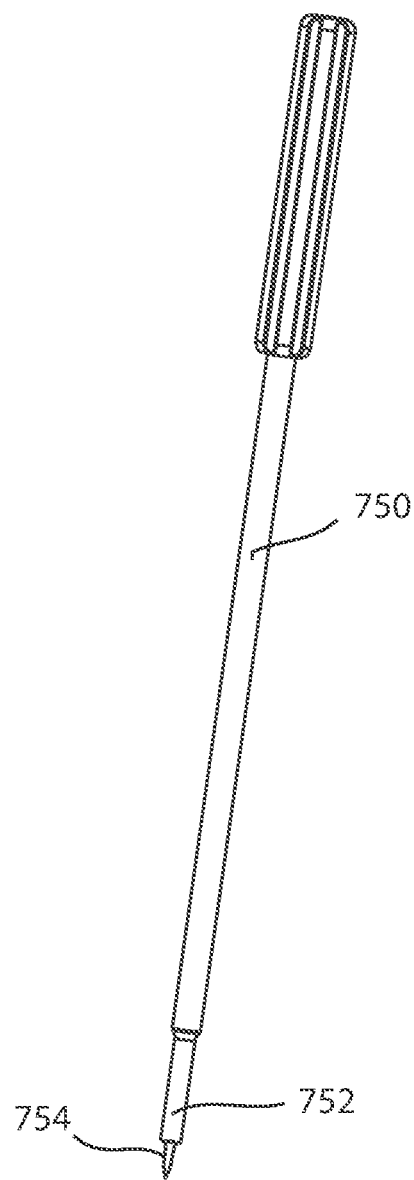
FIG. 25 illustrates a perspective view of the awl of FIG. 24.

Referring to FIGS. 24 and 25, an awl 750 may be used to create pilot holes in the vertebral bodies. A distal end 752 and tip 754 of the awl 750 are shaped to fit through the guide lumen 719. The tip 754 of the awl may be used to penetrate each of the vertebral bodies 2, 4, along the midline and approximately mid-body, creating pilot holes for guide pins.

Figure 26:
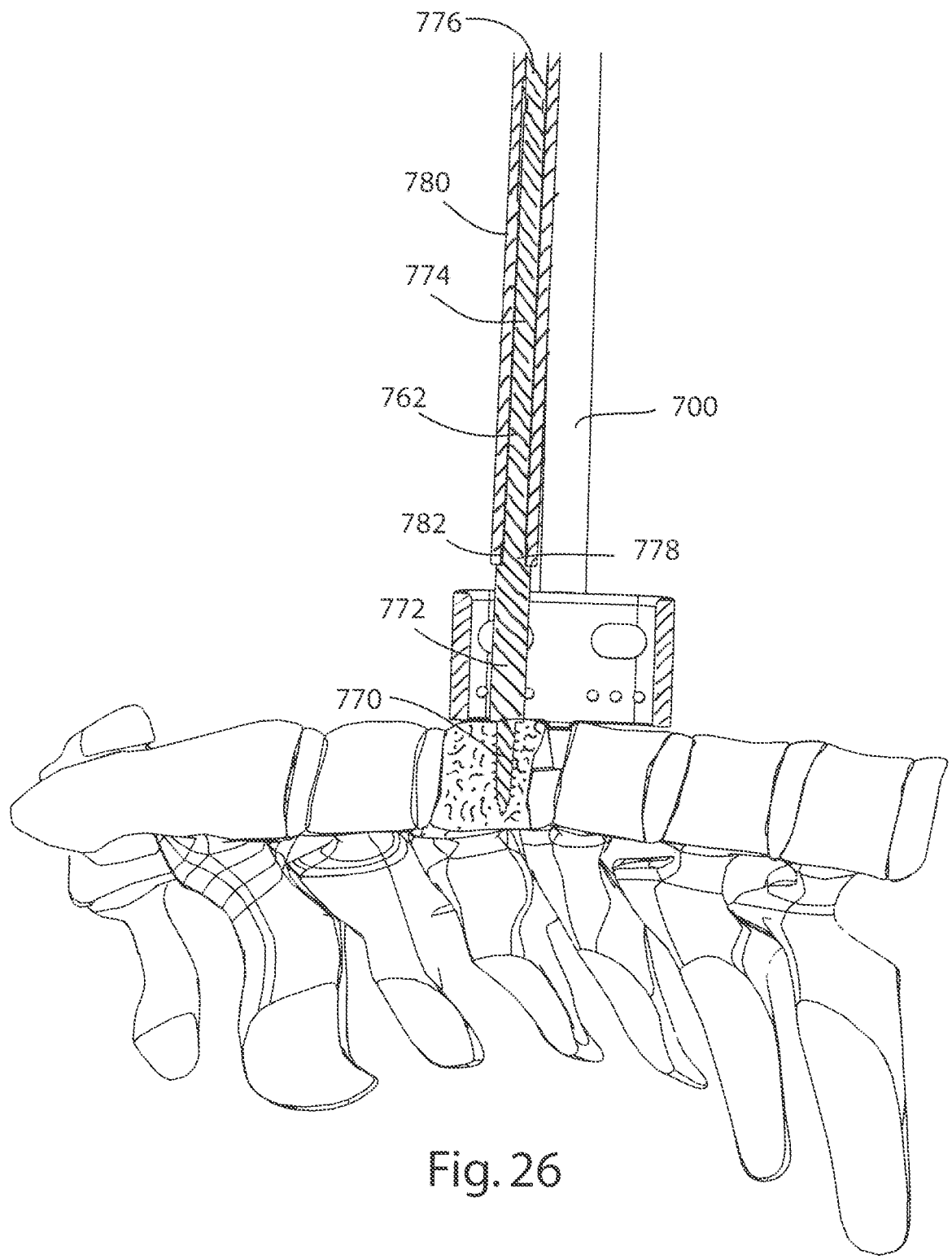
FIG. 26 illustrates a cross-sectional sagittal view of the guide tool and spinal portion of FIG. 22, with a driver tool driving a pin into a vertebral body.
Figure 27:
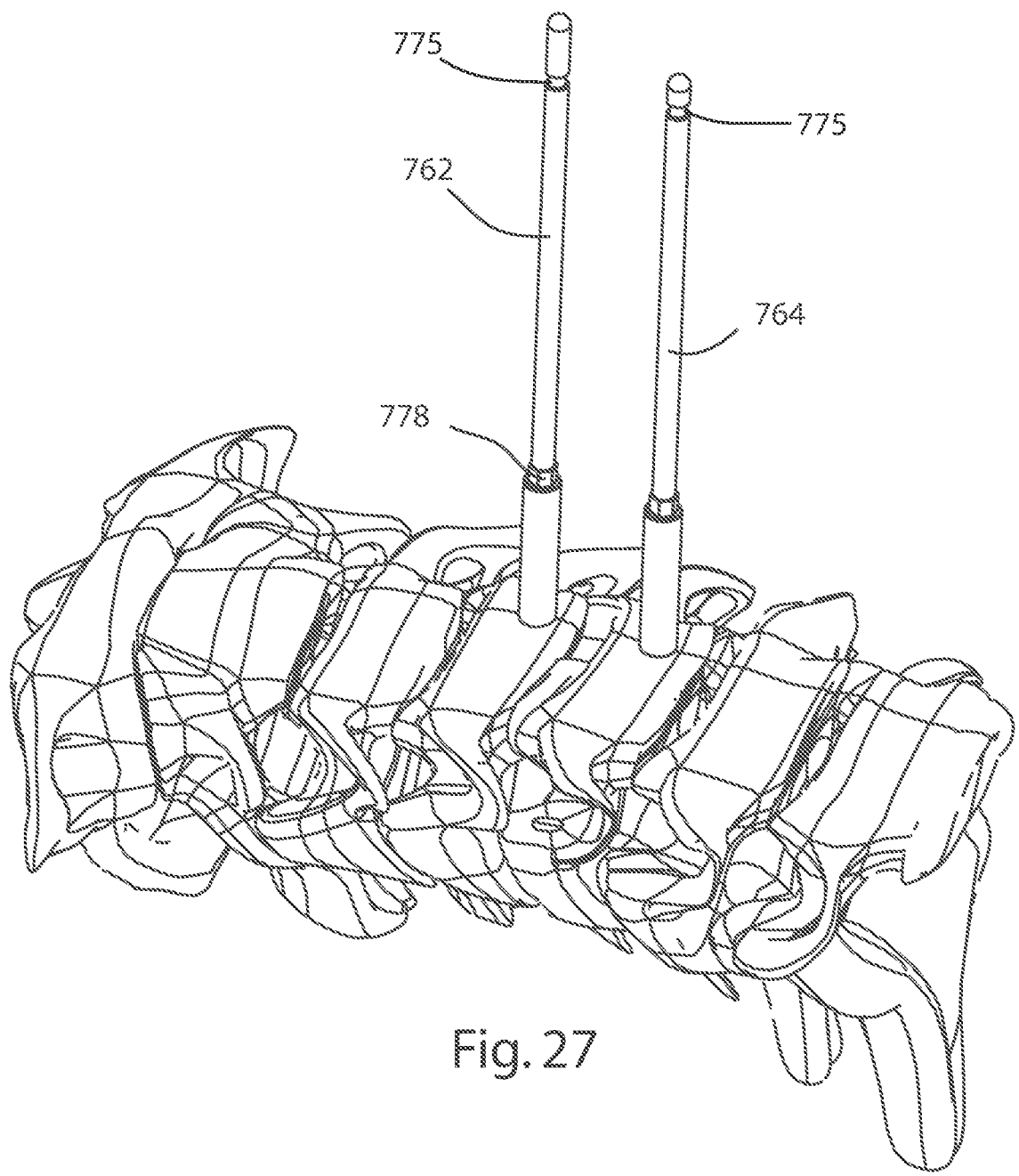
FIG. 27 illustrates the spinal portion of FIG. 21, with two pins driven into adjacent vertebral bodies.

Referring to FIGS. 26 and 27, a guide pin 762 is inserted through the guide lumen 719 of the head 710 and driven into vertebral body 2 on the sagittal midline and a guide pin 764 is driven into the adjacent vertebral body 4 on the sagittal midline, the pins co-planar with one another, using the pilot holes if necessary. Guide pins 762 and 764 may be identical or may differ in length. Guide pins 762, 764 each comprise a distal threaded penetrating tip 770, a distal shaft portion 772, a middle shaft portion 774 and a proximal shaft portion 776. A recessed groove 775 encircles the shaft, providing an interface for connection to other instruments. A driver engagement interface 778 is configured to engage with a corresponding drive feature 782 on a driver tool 780, which is rotated to drive and each pin 762, 764 into its respective vertebral body. The interface 778 and corresponding drive feature 782 may be shaped as a hexagon or another shape. The guide pins 762, 764 are implanted on the sagittal midline approximately mid-body and parallel to the target disc space. Once the guide pins are secured, the guide 700 tool may be removed.

Figure 28:
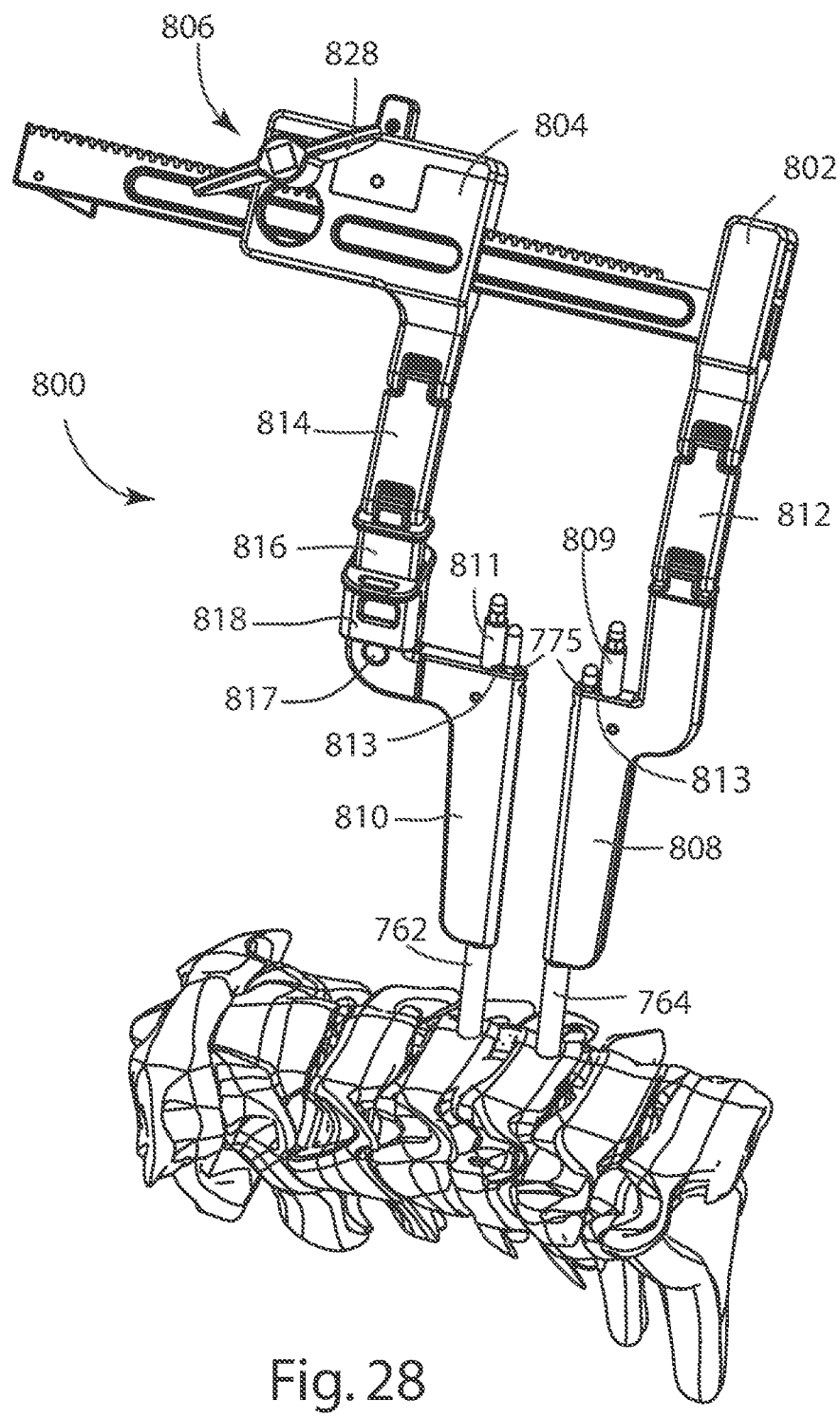
FIG. 28 illustrates an adjustable retainer secured to the pins of FIG. 27.

Referring to FIGS. 28 and 29, a retainer 800 is placed on the pins 762, 764. The retainer 800 is an adjustable bracket system which may be placed in engagement with the pins 762, 764 to adjust and maintain a distance between the pins and the vertebral bodies in which the pins are secured, thereby providing an accessible working area in the intervertebral space between the targeted vertebral bodies. A rack and pinion system provides compressive force or distractive force to urge the pins and therefore the vertebral bodies together or apart. The retainer 800 also provides a guiding framework for additional instruments, permitting the instruments and prostheses to be placed in a preferred orientation with respect to the sagittal midline of the vertebral bodies. Referring to FIG. 28, the retainer 800 comprises a first bracket 802, a second bracket 804, a rack and pinion system 806, and two plates 808, 810 which are configured to fit over and engage the pins 762, 764. Plate 808 may be fit over pin 762 and locked to the pin by engaging a lock 809, and plate 810 may be fit over pin 764 and locked to the pin by engaging a lock 811. Each lock 809, 811 comprises a tab 813 which is rotated in one direction into engagement with the groove 775 on the respective pin to provide a locked configuration and may be rotated in the opposite direction to provide an unlocked configuration. A pair of links 812, 814 hingedly connect the plates 808, 810 to the brackets 802, 804. Between the plate 810 and the second bracket 804 is an additional link 816 and a pivot pin 817, around which plate 810 which may be pivoted to allow angular movement of plate 810 and pin 762 during prosthesis implantation, revision and/or removal procedures. A collar 818 is slidable between a first position, seen in FIG. 28, in which it prevents pivoting of plate 810 around the pivot pin, and a second position in which plate 810 is free to pivot. When plate 810 is allowed to pivot, the angularity of plate 810, pin 762 and associated vertebral body 2, may be adjustable out of a parallel position relative to plate 808, pin 764 and associated vertebral body 4. This adjustability may be useful or necessary during the insertion of trials into the intervertebral space, or during other steps of the implantation procedure.

Figure 29A:
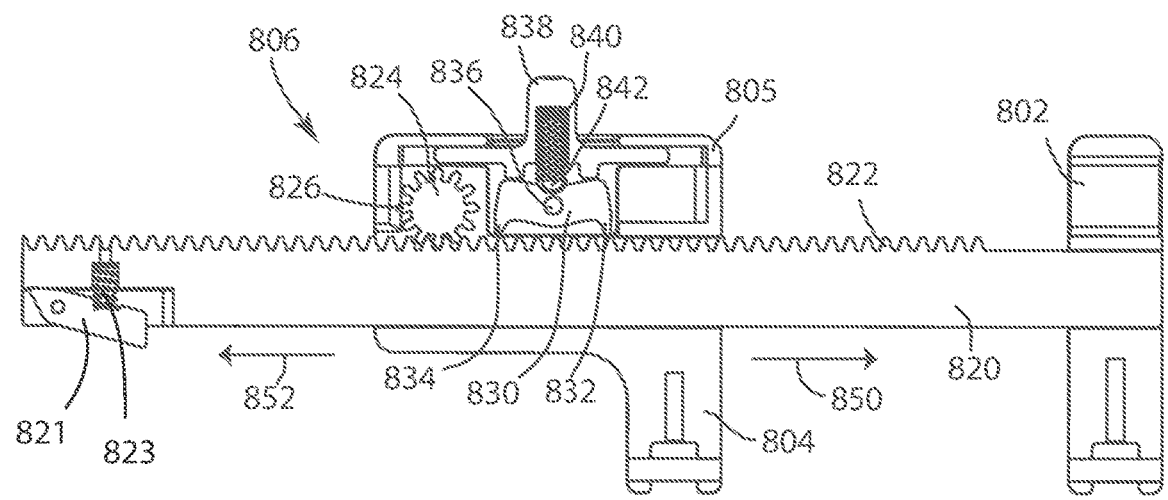
FIG. 29A illustrates a rack and pinion system of the adjustable retainer of FIG. 28, with a pawl in a neutral position.
Figure 29B:
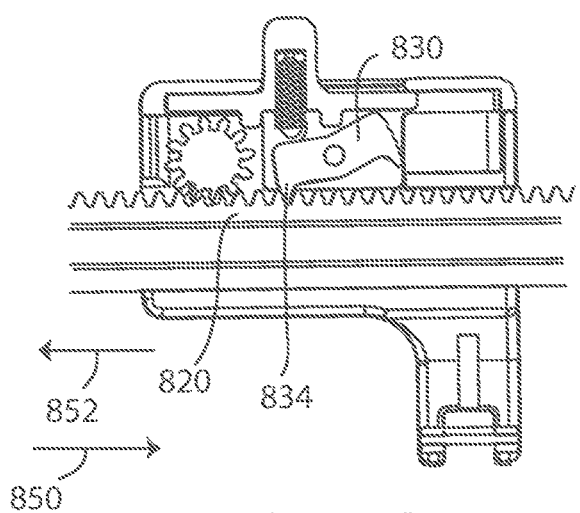
FIG. 29B illustrates the rack and pinion system with the pawl in a position to allow only compression.
Figure 29C:
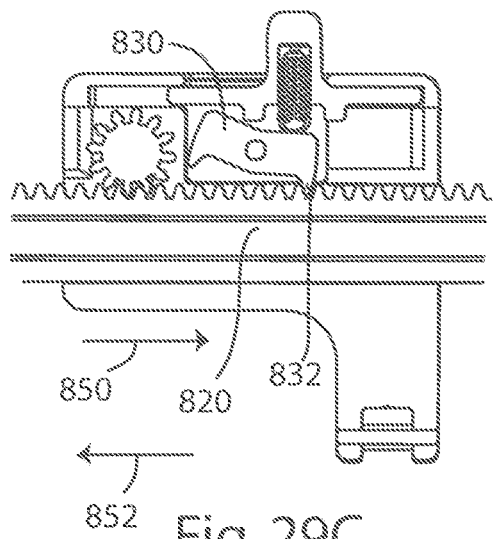
FIG. 29C illustrates the rack and pinion system with the pawl in a position to allow only distraction.

FIGS. 29A-29C illustrate cross-sectional views of the brackets 802, 804 and the rack and pinion system 806. The rack and pinion system 806 is housed inside a bracket housing 805, although the rack may extend out of the housing. The rack and pinion system 806 includes a rack 820 with a row of rack teeth 822. The rack 820 is rigidly connected to the first bracket 802 by welding or other means and passes through the housing 805. A spring-loaded stop arm 821 extends from the rack and prevents the rack from being unintentionally withdrawn from the housing 805. When withdrawal of the rack from the housing is desired, the stop arm 821 may be depressed toward the rack 820, compressing a spring 823. A pinion 824 includes pinion teeth 826 and may be turned by a pinion wing 828 (seen in FIG. 28). The position of a pawl 830 controls whether the retainer provides ratcheting compressive or distractive force to the pins 762, 764, and the pawl is movable between a first position, a second position, and a third neutral position. The pawl 830 comprises a first pawl tooth 832, a second pawl tooth 834, and is pivotable about a pivot pin 836. A toggle 838 may be switched between the first, neutral and second positions, controlling a spring 840 and plunger 842 which engage the pawl 830, moving it between the first, neutral and second positions. FIG. 29A shows the toggle 838 and the pawl 830 in the neutral position. In the neutral position, the pawl is not engaged with the rack teeth 822, and the rack 820 can move in either direction relative to the second bracket 804 by turning the pinion 824 to engage the rack. To attain the first, or distraction, position, the toggle 838 is moved in a first direction 850 such that the plunger 842 may depress the first pawl tooth 832 into engagement with the rack 820, as shown in FIG. 29C. With the pawl in this first position, the rack 820 can only move in direction 852 relative to the second bracket 804 as the pinion 824 is turned to engage the rack. Since the rack 820 is connected to the first bracket 802, first bracket 802 also moves in direction 852 relative to the second bracket 804, moving the brackets 802, 804 away from one another. Since brackets 802, 804 are linked to plates 808, 810 locked to the pins 762, 764, movement of the rack in direction 852 results in distraction of the pins 762, 764 and the vertebral bodies 2, 4.

Referring to FIG. 29B, when the toggle 838 is moved past the neutral position in a second direction 852, plunger 842 may depress the second pawl tooth 834 into engagement with the rack 820, placing the pawl 830 in a second, or compression, position. With the pawl in this second position, the rack 820 can only move in direction 850 relative to the second bracket 804 as the pinion 824 is turned to engage the rack, thereby moving brackets 802, 804 closer together. Movement of the brackets 802, 804 closer together results in compression of the pins 762, 764 and the vertebral bodies 2, 4. Before the retainer is placed on the pins 762, 764, the pawl 830 may be placed in the neutral position, permitting the rack to move freely in either direction, and allowing a distance between the brackets and plates to be adjusted to match a distance between the pins. The plates 810, 808 are place over the pins 762, 764 and the locks 809, 811 are engaged to lock the plates to the pins. The driver tool 780 may be used to engage the locks 810, 811. Then, distraction or compression may be accomplished by the methods described above, i.e., the toggle 838 is moved to the first position and the pinion is turned to provide only distraction, the toggle 838 is moved to the second position and the pinion is turned to provide only compression. Alternatively, the toggle 838 may be placed in the neutral position to allow unconstrained distraction and/or compression. It is appreciated that the retainer 800 may be placed over the pins 762, 764 in either direction, that is, plate 808 may be place over pin 764 and plate 810 over pin 762, or alternately, plate 810 may be placed over pin 764 and plate 808 over pin 762. It is also appreciated that in an alternative embodiment of the invention, each bracket may comprise an adjustable feature such as a rack and pinion system, to provide distraction and compression between the brackets, pins and associated vertebral bodies. In addition, a pivoting feature such as pivot pin 817 and collar 818 could be on either or both platers.

As seen in FIG. 28, link 812 connects plate 808 with bracket 802, and links 814 and 816 connect plate 810 with bracket 804. The links and brackets may be hinged so that they may be rotated about the cephalad-caudal axis of the vertebrae, toward one lateral side or the other, allowing for optimal visibility and access to the surgical site.

Figure 30:
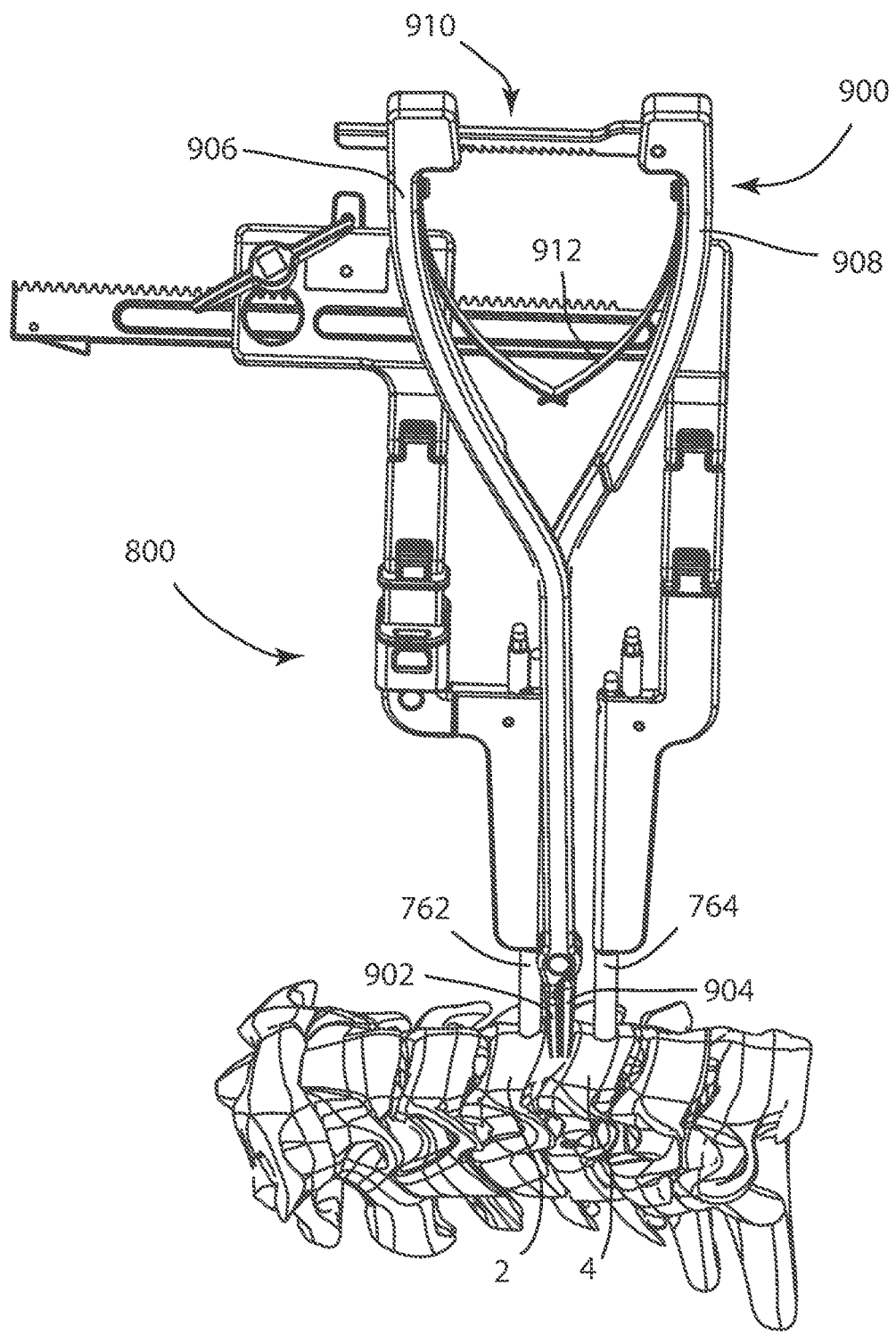
FIG. 30 illustrates the adjustable retainer of FIG. 28 and a separate distractor tool.

As seen in FIG. 30, a distractor 900 may be used with the retainer 800 to aid in providing sufficient distraction between the vertebral bodies 2, 4, if necessary or desired. Prongs 902, 904 of the distractor 900 may be inserted into the intervertebral space, and levers 906, 908 compressed together to provide distraction. A ratcheting mechanism 910 allows the levers to be locked in a fixed position, and a leaf spring 912 provides the resistance for the distraction. Such distraction may be provided while the retainer pawl 830 is in the neutral position or in the first position. Once the vertebral bodies are sufficiently distracted, the retainer pawl 830 may moved to the first position if not already there, to maintain the spacing between the vertebral bodies. Distractor 900 may comprise a locking feature to hold the levers 906, 908 and prongs 902, 904 in a fixed position, until released.

Figure 31:
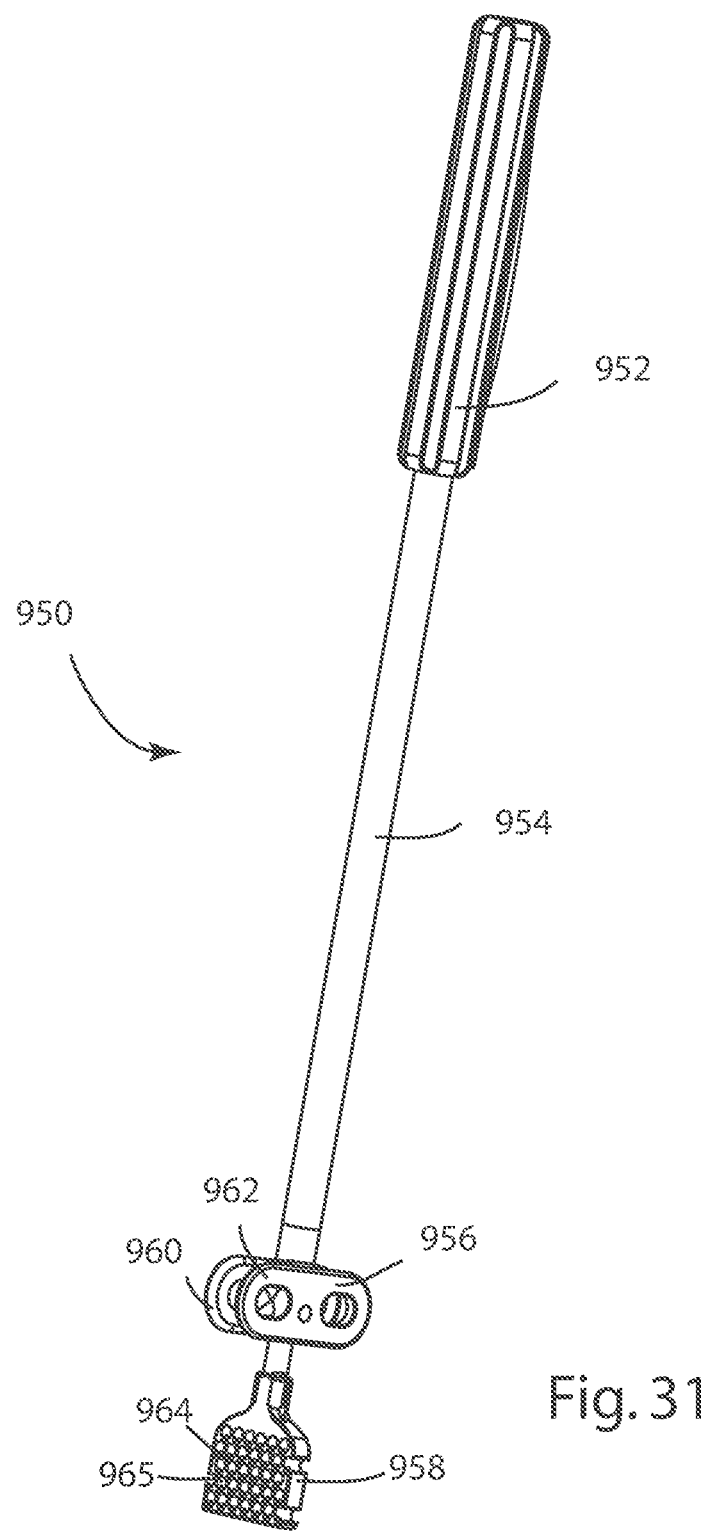
FIG. 31 illustrates a rasp tool which may be used with the adjustable retainer of FIG. 28.
Figure 32:
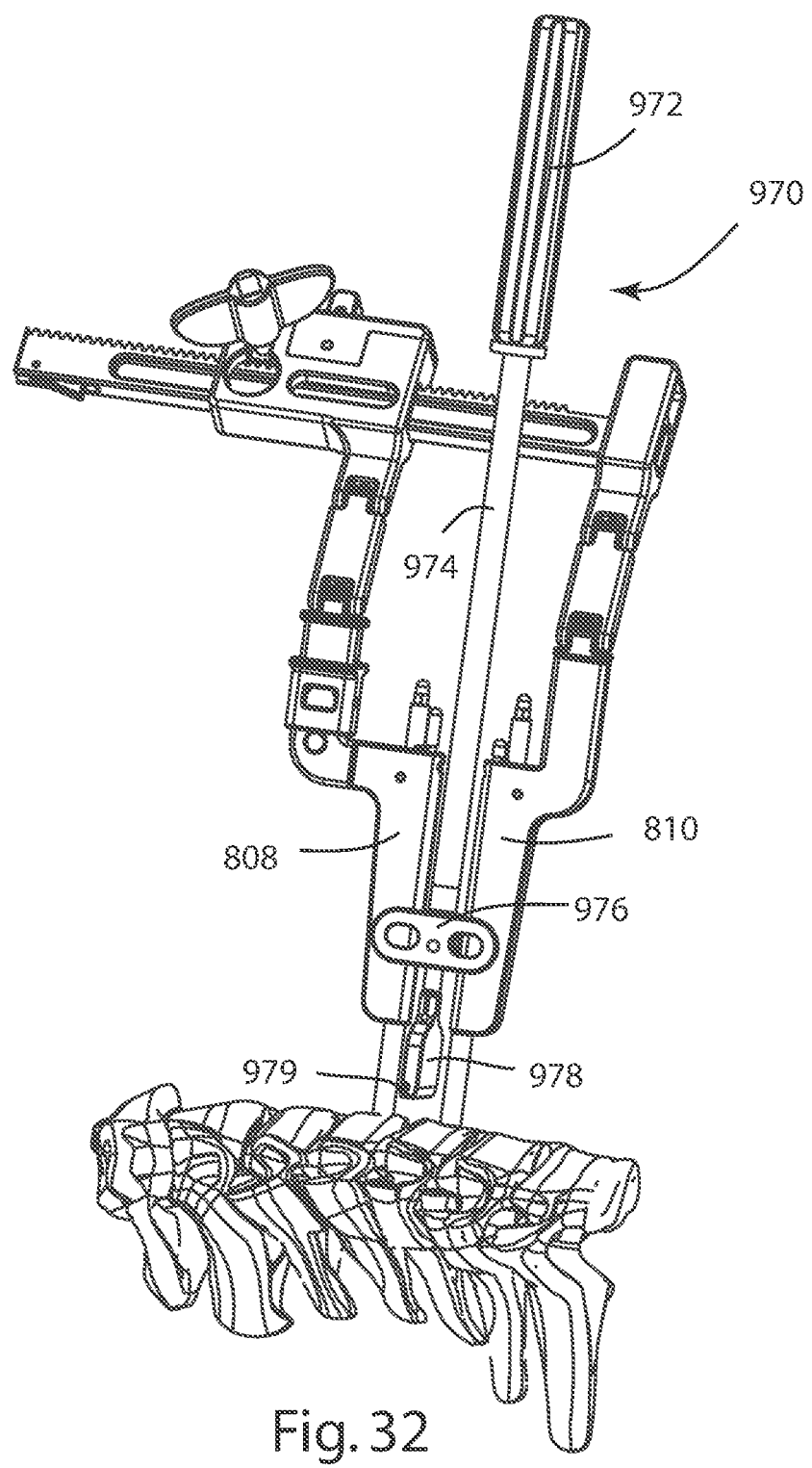
FIG. 32 illustrates the adjustable retainer of FIG. 28 guiding a planer tool.

After the vertebral bodies are sufficiently distracted, a discectomy and decompression may be performed using instruments know in the art such as ronguers, curettes and osteotomes. Bone rongeurs, planers, rasps, burr tools or other instruments may be used to prepare flat surfaces on the vertebral endplates, as flat surfaces may ensure the best interface between the prosthesis end plates and the vertebral endplates. Endplate preparation may also include forming grooves to correspond with teeth or keels of a prosthesis, roughening or smoothing the surface to enhance conformance with the prosthesis or encourage bony ingrowth and stabilization of the prosthesis, and/or contouring the shapes of the endplates. FIG. 31 illustrates a rasp 950 which may be inserted between the vertebral bodies 2, 4 to scrape and flatten the endplates. Rasp 950 comprises a gripping portion 952, a shaft 954, a pair of wings 956 and a rasp head 958. The rasp head comprises a plurality of cutting edges 964, which may be undercut and each of which may be adjacent an opening 965, which during rasping may allow cut material to flow through to the opposite side of the head and not clog the cutting edges. Additionally, the cutting edges may cut only in the posterior-to-anterior direction, making insertion into the intervertebral area easier and less traumatic than it would be with a rasp which cuts in the anterior-posterior direction. The wings 956 comprise wing plates 960, 962 which flank either side of the shaft 954 and are aligned perpendicular to the rasp head 958. The wings 956 are a guiding feature which allow the rasp 950 to be inserted into the intervertebral space in alignment with the retainer 800, along a pathway substantially parallel with the pins 762, 764. With reference to FIG. 28, the rasp 950 may be inserted between the plates 808, 810 such that the wing plates 960, 962 slide over retainer plates 808, 810 in a fixed orientation. With the rasp 950 thus aligned, the rasp head 958 will enter the intervertebral space in a preferred orientation parallel to the vertebral endplates and relative to the sagittal plane. It is appreciated that other instruments including but not limited to a planer, blade, grater, or cutter could have a guiding feature comprising similar wing plates, permitting alignment with the retainer plates 808, 810 and correct orientation of the instrument relative to the sagittal plane. FIG. 32 illustrates a planer which may also be used in endplate flattening and preparation in an alternative embodiment. Planar 970 comprises a gripping portion 972, a shaft 974, a pair of wings 976 and a planer head 978 with a cutting edge 979.

Figure 33:
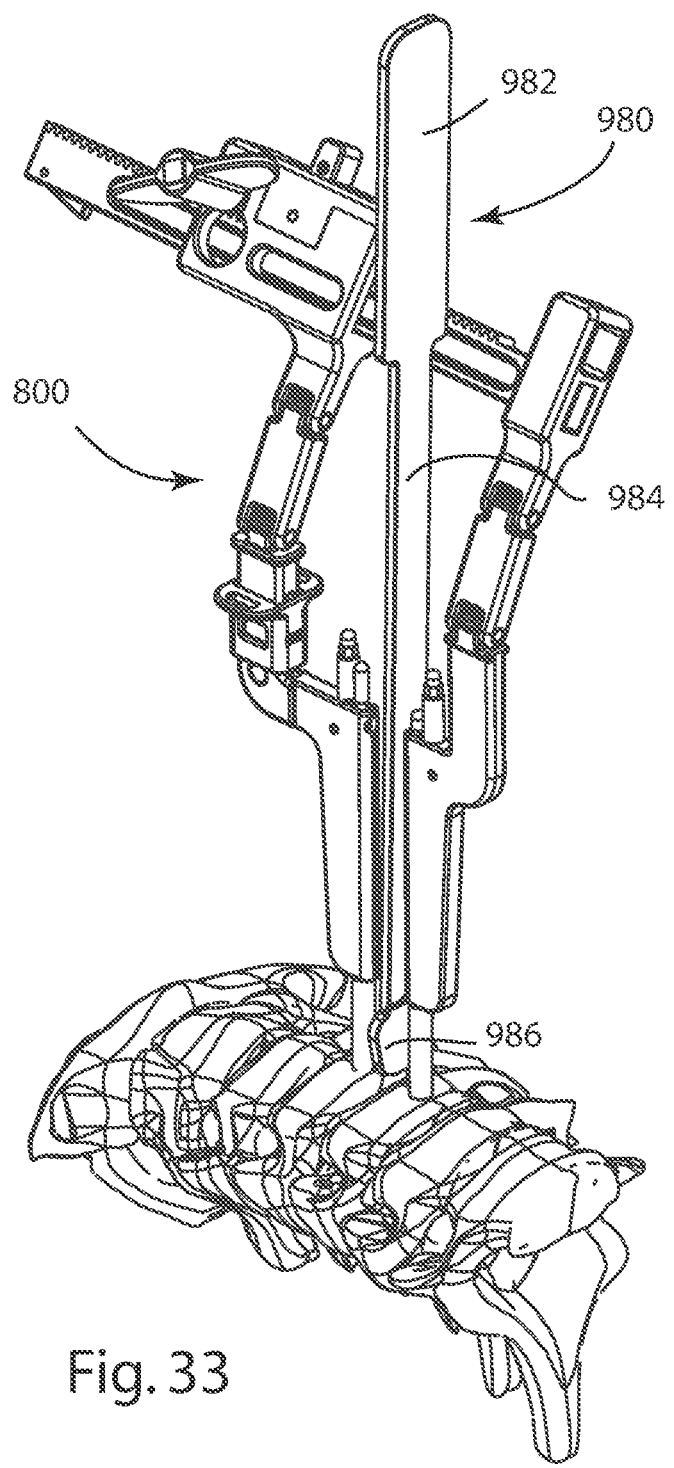
FIG. 33 illustrates the adjustable retainer of FIG. 28 and a feeler tool.

Referring to FIG. 33, a feeler 980 may be employed to evaluate the configuration of the intervertebral space, to assess endplate flatness and determine which implant footprint best fits the space. The feeler 980 comprises a handle 982, a shaft 984 and a paddle 986 with flat sides. The feeler may be available in a plurality of sizes such as small, medium and large, each size comprising a paddle with a comparable footprint size to a prosthesis such as prosthesis 100. As seen in FIG. 33, the feeler may be inserted between the plates 808, 810 of the retainer until the paddle 986 is in the intervertebral space. Visual observation or fluoroscopy may be used to observe the size of the paddle 986 relative to the vertebral endplates, to determine the correct prosthesis footprint size. The paddle 986 may be pressed or rubbed against the prepared vertebral endplates to assess flatness of the endplates, and/or fluoroscopy may be used to observe the profiles of the endplates compared to the profile of the paddle to assess flatness. The feeler may be available in a variety of sizes, and other embodiments of the feeler may include wings such as those on the rasp 950 to allow precise guidance by the retainer 800. Once the flatness of the vertebral body endplates is assessed, additional preparation with a rasp, planer, hammer, burr and/or other tools may occur if necessary to relieve concavities, convexities, or other irregularities on the endplate surfaces. These steps of assessment and preparation may be repeated as needed.

Figure 34:
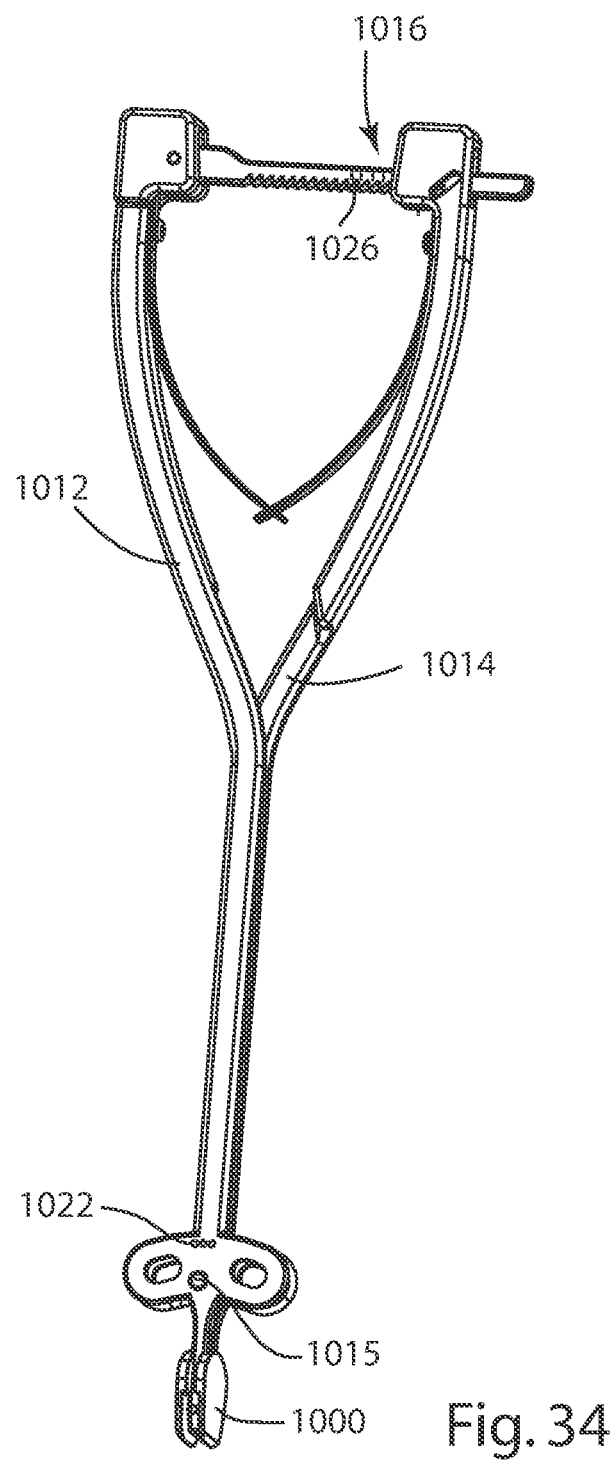
FIG. 34 illustrates a trial.
Figure 35:
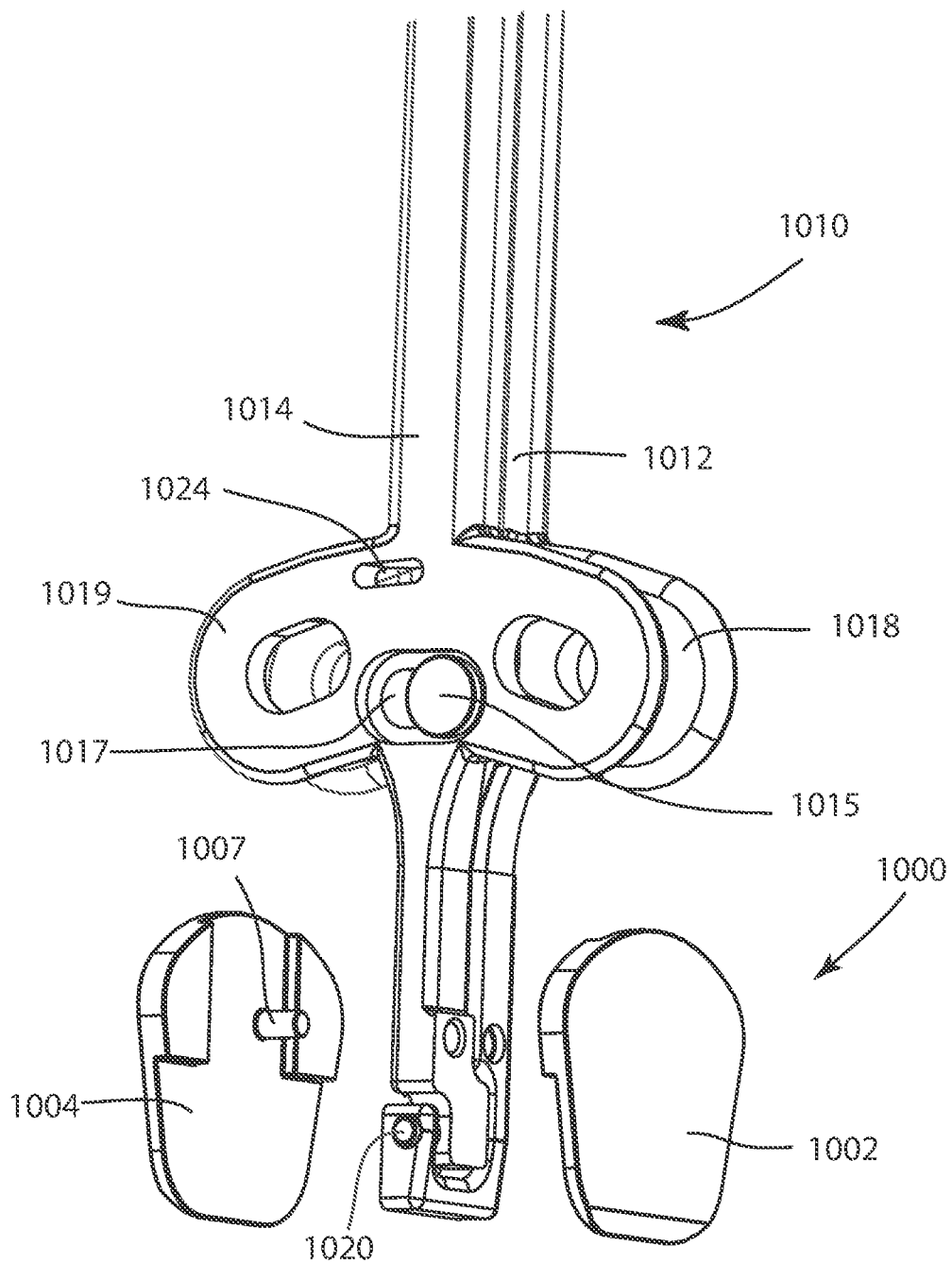
FIG. 35 illustrates an exploded view of the trial of FIG. 34.
Figure 36:
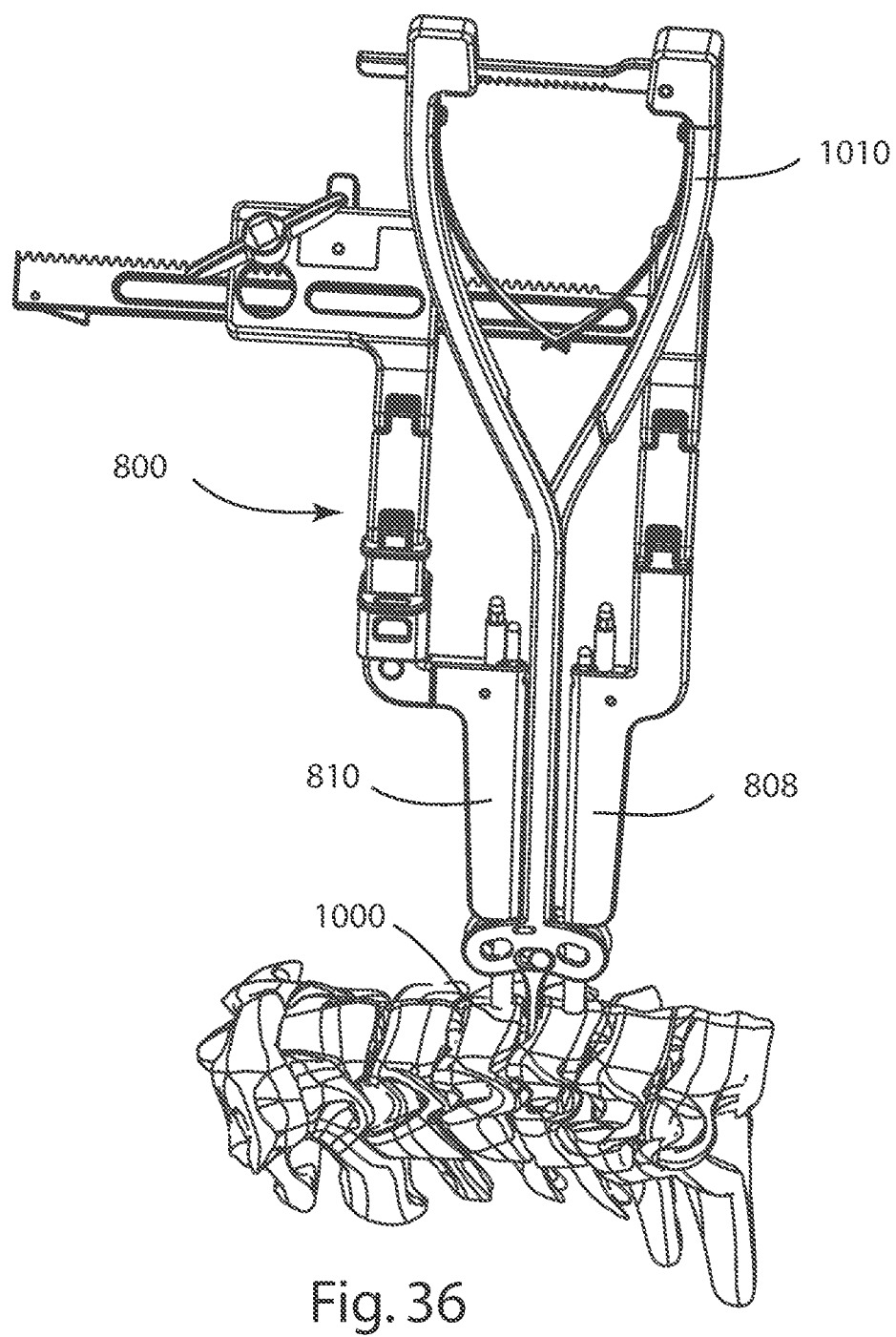
FIG. 36 illustrates the trial of FIG. 34 guided by the adjustable retainer of FIG. 28.

Referring to FIGS. 34-36, a trial or trials may be inserted into the prepared intervertebral space to determine the lordotic correction, if any, that is needed. Trials are available in a variety of footprint sizes, matching the feeler and prosthesis footprint sizes. Alternative embodiments of trials may include those shaped as intervertebral disc replacements, fusion cages, spacers, or other intervertebral implants. FIG. 34 illustrates a trial 1010, and FIG. 35 illustrates a partially exploded view of a distal end of the trial. Trial 1010 comprises a head 1000 with first trial plate 1002 and a second trial plate 1004. Trial plate 1002 has a peg 1006 (not visible in FIG. 35) which joins it to a first lever 1012, and trial plate 1004 has a peg 1007 joining it to a second lever 1014. The plates 1002, 1004 may be secured to the inserter by inserting each peg through a corresponding hole in the distal end of each lever. Alternately, the plates may be permanently welded to the levers.

Trial 1010 further comprises a first lever 1012 and a second lever 1014. At their proximal ends, the levers 1012, 1014 are joined by a ratcheting mechanism 1016. Near their distal ends, the levers are linked by a rivet 1015. Rivet 1015 is joined to lever 1012 and captured in a slot 1017 on lever 1014, such that the levers can move relative to one another, but such movement is constrained by the length of the slot 1017. First lever 1012 comprises a first wing 1018, and second lever 1014 comprises a second wing 1019, the wings positioned so that the inserter may be slid over the plates of the retainer 800, positioning the inserter with respect to the pins 762, 764 and the targeted intervertebral space. A pivot pin 1020 joins the levers 1012, 1014 at their distal ends, allowing the levers to rotate about the pin 1020 and pivot relative to one another.

FIG. 36 illustrates insertion of the trial 1010 into the intervertebral space between the prepared endplates. A trial is chosen with an appropriate footprint size determined by use of the feeler. The proximal ends of the levers are positioned so that the distal ends are approximately parallel to one another, so that the trial plates 1002, 1004 are also parallel with respect to one another. The trial 1010 is inserted between the retainer plates 808, 810, and the levers are positioned so that the wings 1019, 1018 flank the plates 808, 810, thereby positioning the head 1000 in a preferred orientation relative to the sagittal plane. The head 1000 is further inserted, into the intervertebral space. Fluoroscopy may be used to place the head at a desired depth within the intervertebral space.

The desired degree of lordotic correction may be determined by adjusting the angle of the trial plates 1002, 1004 within the intervertebral space. Levers 1012, 1014 are ratcheted together, causing their distal ends to pivot apart around the pivot pin 1020, and causing trial plates 1002, 1004 to pivot apart until the desired angle, or degree of lordotic correction is reached, which may be visualized through fluoroscopy. A reference feature, which may comprise markings and/or alignable holes on the trial 1010 may also be used to measure the degree of lordotic correction. Once the degree of lordotic correction is determined, the trial inserter 1010 may be released, allowing the trial plates 1002, 1004 to return to a parallel position for removal, and the trial 1000 is removed from the intervertebral space. Observations of footprint size and degree of lordotic correction may be used to select a properly configured prosthesis for implantation. Another embodiment of the trial may include a shaft which is distally displaced to pivot the trial plates.

One reference feature on the trial may comprise holes located on the first lever, which may be coaxial with a slot on the second lever to indicate an angulation or degree of lordotic correction. First lever 1012 comprises an array of holes 1022, and second lever 1014 comprises an elongated slot 1024. When the first and second levers are at one position relative to one another, and therefore the plates are at one angle, a first hole in the array 1022 is coaxial with the slot 1024. When the first and second levers are at a second position, and thus the plates at a second angle, two holes in the array 1022 are coaxial with the slot 1024. When the first and second levers are at a third position, and thus the plates at a third angle, three holes in the array 1022 are coaxial with the slot 1024. It is appreciated that in other embodiments of the invention, the array may comprise more or less than three holes, and the array and the slots may be situated at various locations on the trial. The alignment of the array with the slot may is viewed from a viewpoint normal to the array and may be viewed unaided or may be viewed through the use of fluoroscopy. Alternatively, or in addition to the coaxial holes and slot, markings 1026 on the ratcheting mechanism may indicate the angulation or degree of lordotic correction.

Figure 37:
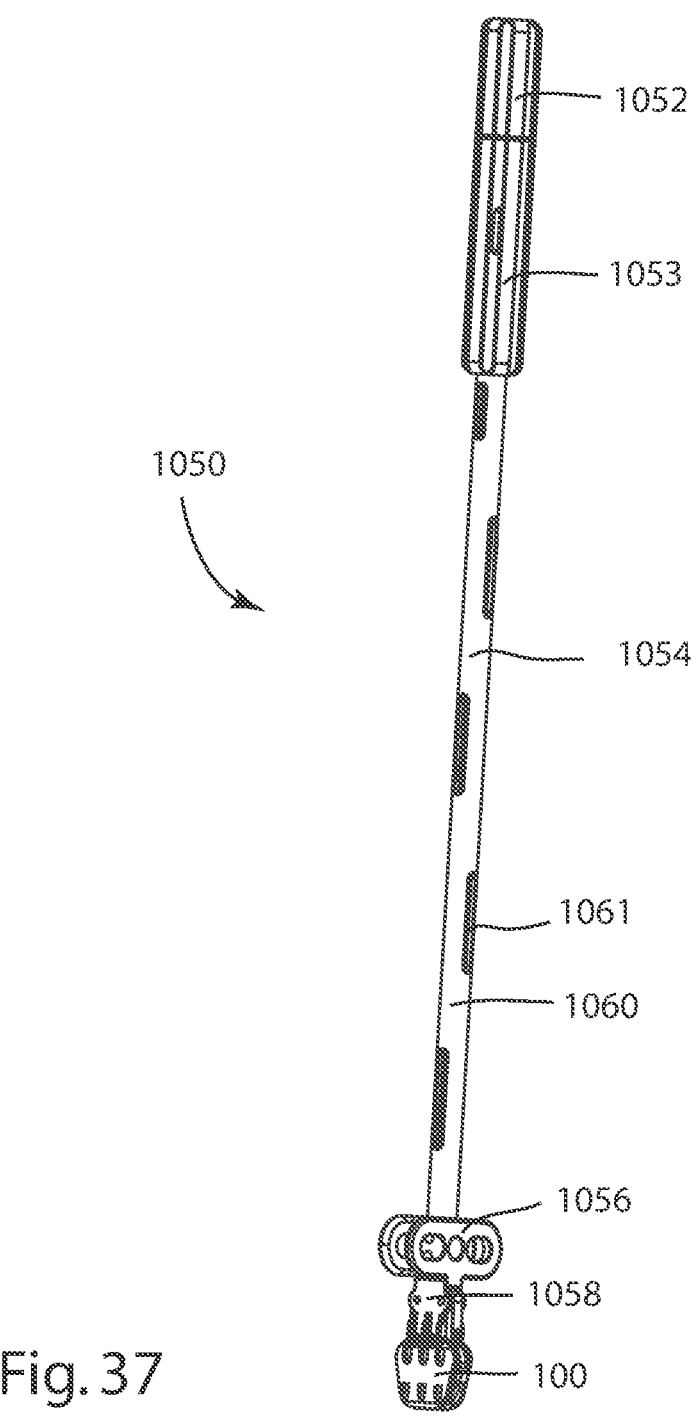
FIG. 37 illustrates an implant inserter gripping the implant of FIG. 1.

FIGS. 37-41 illustrate the insertion of an intervertebral disc prosthesis 100 into the prepared intervertebral space between vertebra 2 and 4. It is appreciated that the methods and instrumentation presented herein could be used to implant prostheses 400, 600 or other similar artificial disc prostheses. Referring to FIG. 37, an implant inserter 1050 is shown, gripping the prosthesis 100. Implant inserter comprises a rotatable handle portion 1052, a fixed handle portion 1053, a shaft 1054, wings 1056, and a gripping mechanism 1058. The shaft 1054 comprises an outer tube 1060 and a rod 1062 positioned inside the tube. The outer tube 1060 may comprise a plurality of cleaning slots 1061. The rotatable handle portion 1052 is connected to the rod 1062 such that turning the rotatable handle portion 1052 moves the rod 1062 distally or proximally. At its distal end, the rod is connected to the gripping mechanism 1058. When the rod 1062 is displaced distally to a first position, it cams the gripping mechanism 1058 into an open position, and when the rod is displaced proximally to a second position, the gripping mechanism is cammed into a closed position in which the prosthesis 100 may be securely gripped for implantation. The wings 1056 are configured to slide over and flank the retainer plates 808, 810 during implantation to place the instrument and prosthesis in a preferred orientation relative to the sagittal plane.

Referring to FIGS. 38A-38D, enlarged views of the distal end of the inserter and the gripping mechanism are shown. The gripping mechanism comprises a first alignment side 1070 and a second alignment side 1072 which is positioned opposite the first. The alignment side 1070, 1072 are oriented perpendicular to the wings 1056, to place the prosthesis in the proper orientation during implantation. Each alignment member comprises a plurality of prongs 1074 which extend past the ends of the alignment sides, and between which the prosthesis is sandwiched when gripped by the gripping mechanism for handling and insertion. The prongs may be positioned to line up with teeth on the prosthesis end plates 102, 104, for ease of insertion. As the prosthesis is mounted to the inserter, the end plates 102, 104 may be compressed together into a preferred orientation to sandwich the prosthesis together and then slid between the prongs; this compression may help prevent the intervertebral space from becoming overstuffed with the insertion of the prosthesis. At its distal end, which is shaped to complement the anterior end of the prosthesis end plate 102, alignment side 1070 comprises a first key 1076, which is shaped to fit coaxially in a pocket 144 on the anterior end of the end plate 102. Alignment side 1072 comprises a second key 1078 larger than the first key, shaped to fit coaxially in a pocket 174 on the anterior end of the end plate 104. The keys and pockets are specifically sized so that the prosthesis can be mounted on the inserter 1050 in only one, correct, position. It is appreciated that other embodiments of the inserter 1050 may include keying features shaped to engage with gripping recesses, pockets, or other features of implants 400 or 600.

Figure 38A:
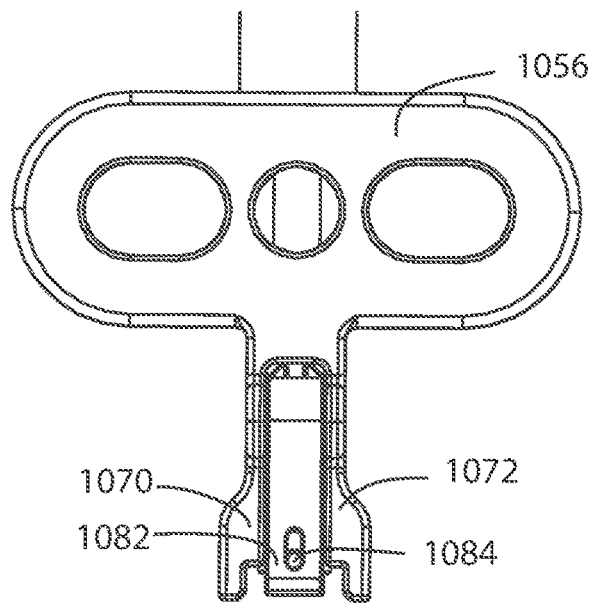
FIG. 38A illustrates a lateral view of a distal end of the implant inserter of FIG. 37.
Figure 38B:
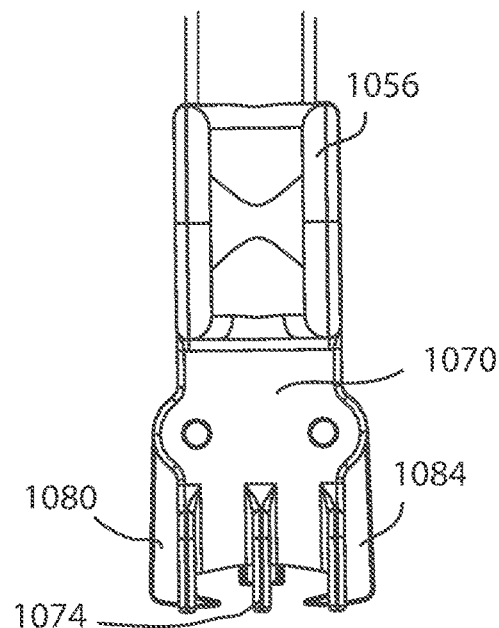
FIG. 38B illustrates a top view of the distal end of the implant inserter.
Figure 38C:
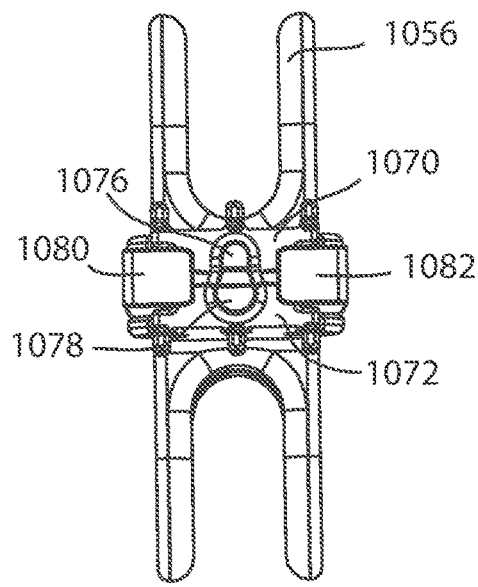
FIG. 38C illustrates an end view of the distal end of the implant inserter.
Figure 38D:
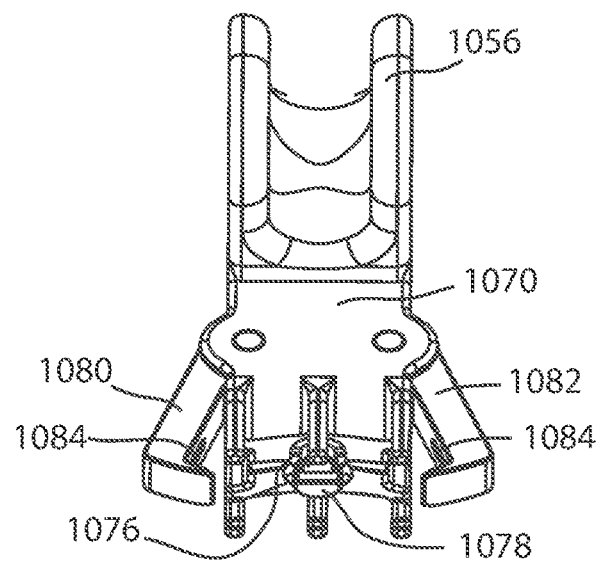
FIG. 38D illustrates a perspective view of the distal end of the implant inserter in an open configuration.
Figure 39:
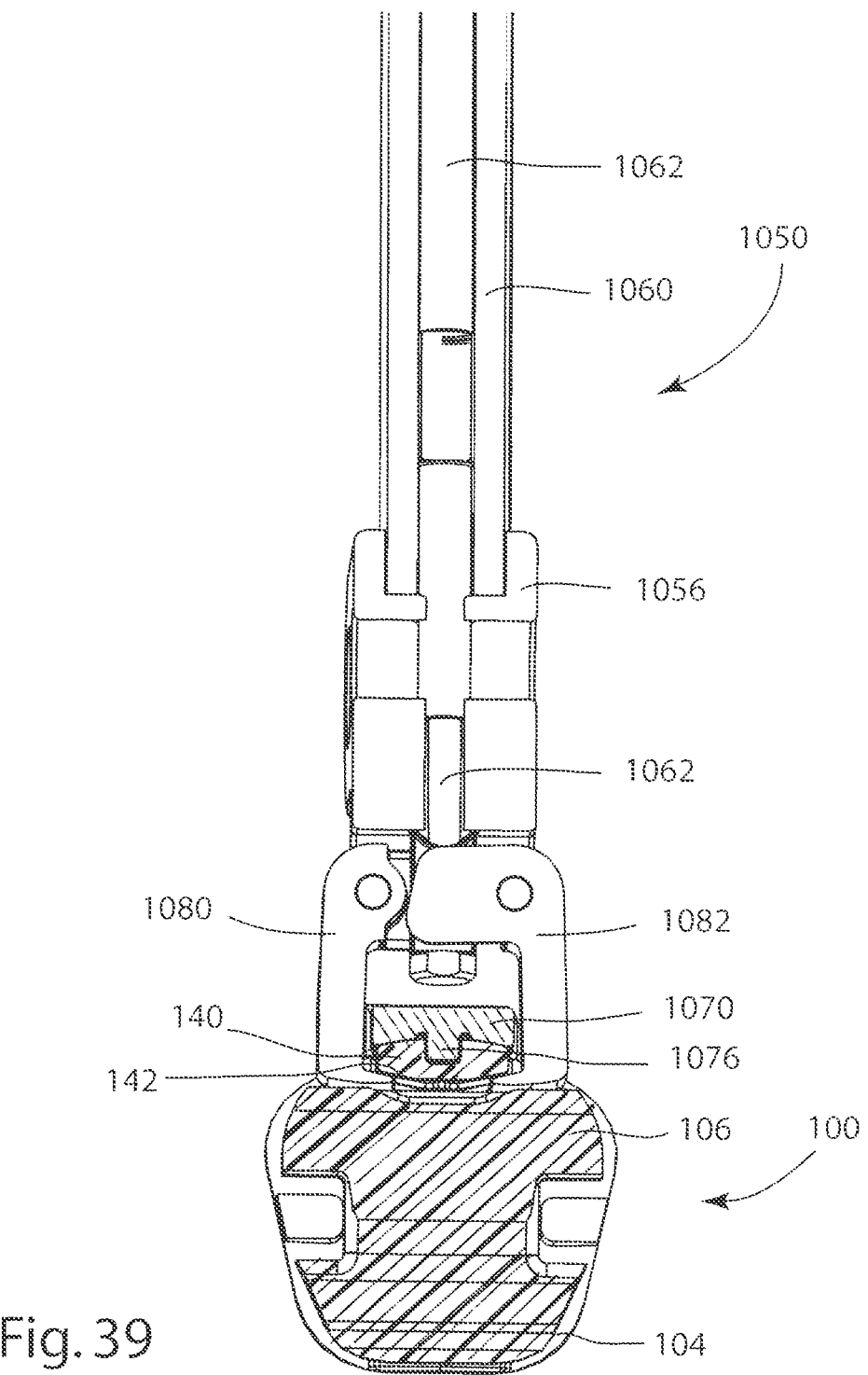
FIG. 39 illustrates a top cross-sectional view of the distal end of the implant inserter and implant of FIG. 37.

The gripping mechanism further comprises two pivotable opposing arms 1080, 1082. When the inner rod 1062 is distally displaced, the arms 1080, 1082 are cammed to an open position to receive the prosthesis 100, as seen in FIG. 38D. The prosthesis is mounted to the inserter such that keys 1076, 1078 on the inserter fit into pockets 144, 174 on the prosthesis 100. Referring also to FIG. 39, the rod is then displaced to a second position to close the arms 1080, 1082, which simultaneously engage with the dovetailed inner edges 142, 172 of motion stops 140, 170, gripping the prosthesis securely. Each arm 1080, 1082 has an aperture 1084. The apertures may be observed with fluoroscopy to monitor the prostheses as it is inserted into the intervertebral space, to monitor and determine the proper depth of implantation.

The desired prosthesis is chosen and mounted on the inserter 1050. The inserter is placed onto the retainer 800, with guiding wings 1056 over the plates 808, 810 of the retainer. The leading (posterior) edge of the prosthesis is inserted into the prepared intervertebral space. At this point, the retainer 800 may be compressed slightly to facilitate endplate fixation. The inserter 1050 may be tapped with a hammer or mallet (not shown) to drive the prosthesis farther into the intervertebral space. As the prosthesis is inserted, the leading self-cutting teeth 130 may cut a track into the vertebral endplates, and the larger second row of teeth 131 enlarge the track. Compression and distraction may be adjusted as needed by the retainer to ensure firm implantation of the teeth 130, 131 into the vertebral endplates. When the implant is adequately placed, the inserter handle 1052 is twisted to release the inserter arms 1080, 1082 from the implant. The retainer 800 and pins 762, 764 are removed and fluoroscopy may be used as needed to assess the final implant placement.

Figures 40A, 40B:
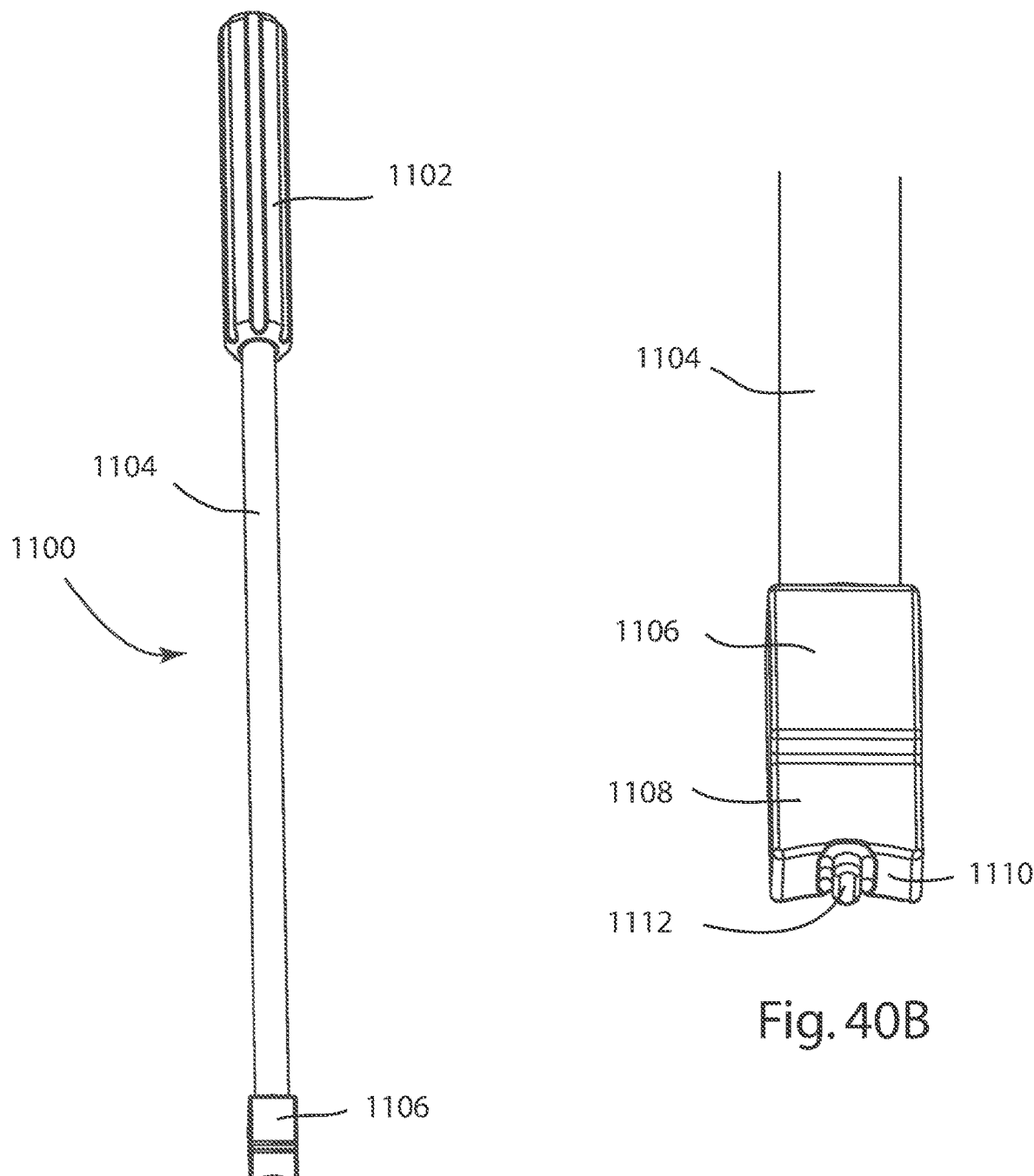
FIG. 40A illustrates a tamp.
FIG. 40B illustrates an enlarged view of the distal end of the tamp.
Figure 41:
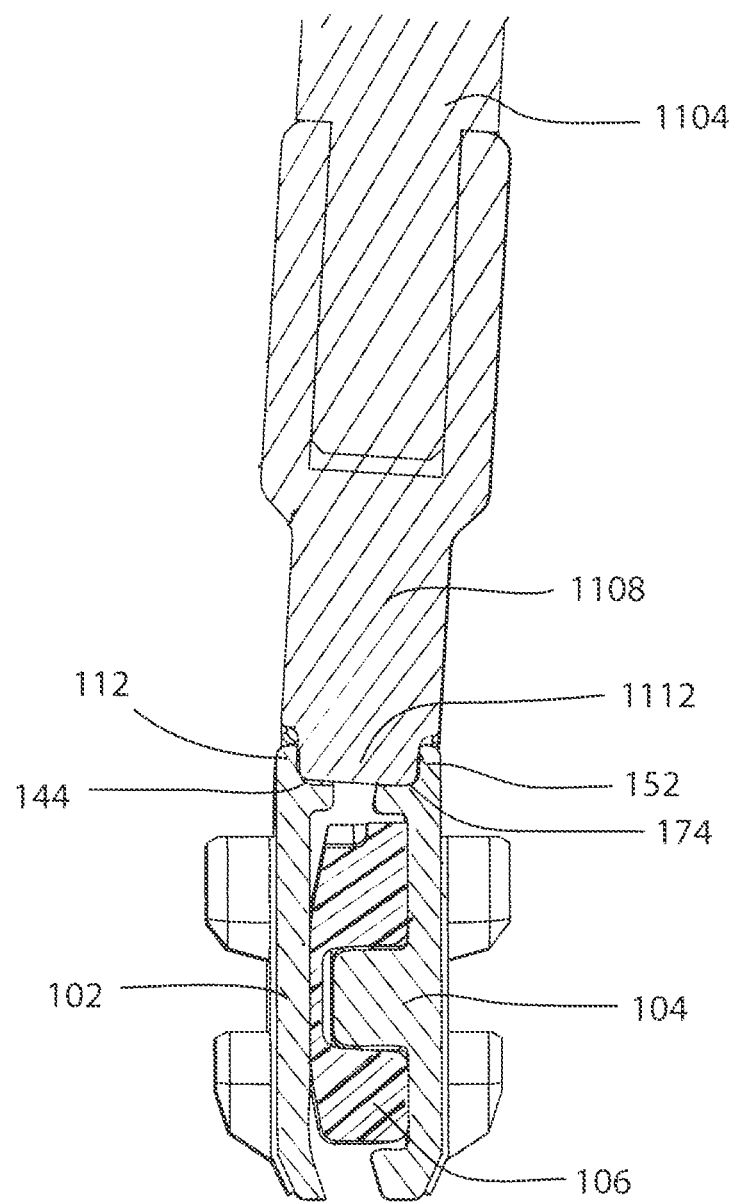
FIG. 41 is a cross-sectional view of the tamp of FIG. 40 fitted to the implant of FIG. 1.

If needed, a tamp may be used to finely adjust the implant until it is fully seated. FIG. 40A illustrates tamp 1100, which comprises handle 1102, shaft 1104 and tamp head 1106. FIG. 40B is an enlarged view of the tamp head 1106, which comprises a body 1108, a distal curved edge 1110 from which protrudes a tab 1112. The body 1108 may comprise a wider upper portion, a taper and narrow lower portion. The taper and wider upper portion may act as a blocking element prevent the tamp and/or prosthesis from being pushed too far into the intervertebral space. The curved edge 1110 is shaped to complement the curved shapes of the anterior ends 112, 152 of the end plates 102, 104 (seen in FIG. 2). As seen in FIG. 41, the tab 1112 is shaped to coaxially mate with the pockets 144, 174 on the end plates. The tamp 1100 may be fitted onto the anterior ends of the end plates 102, 104 with the tab 1112 in the pockets to ensure proper alignment of the end plates relative to one another, and a correct lateral position of the tamp. The tamp may be struck with a hammer or mallet (not shown) to precisely seat the end plates 102, 104 in the vertebral bodies. Other embodiments may include single endplate tamps which are configured to seat each end plate individually. Ensuring proper placement and alignment of the prosthesis will allow the patient to have the optimized range of motion. After the implant is seated in the desired position confirmed by fluoroscopy, all instrumentation may be removed and the surgical site closed.

Figure 42:
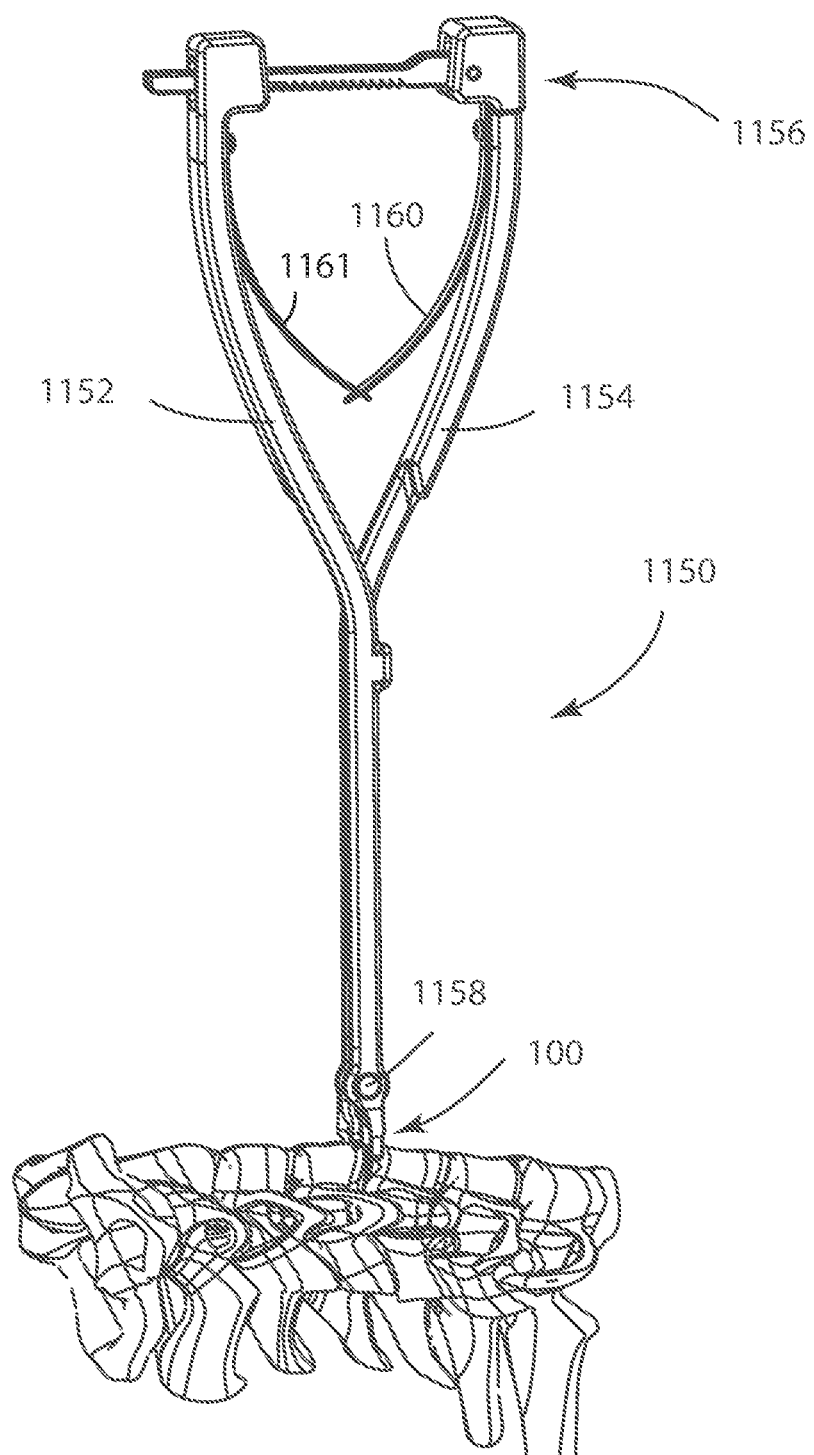
FIG. 42 illustrates a remover tool gripping the implant of FIG. 1.
Figure 43:
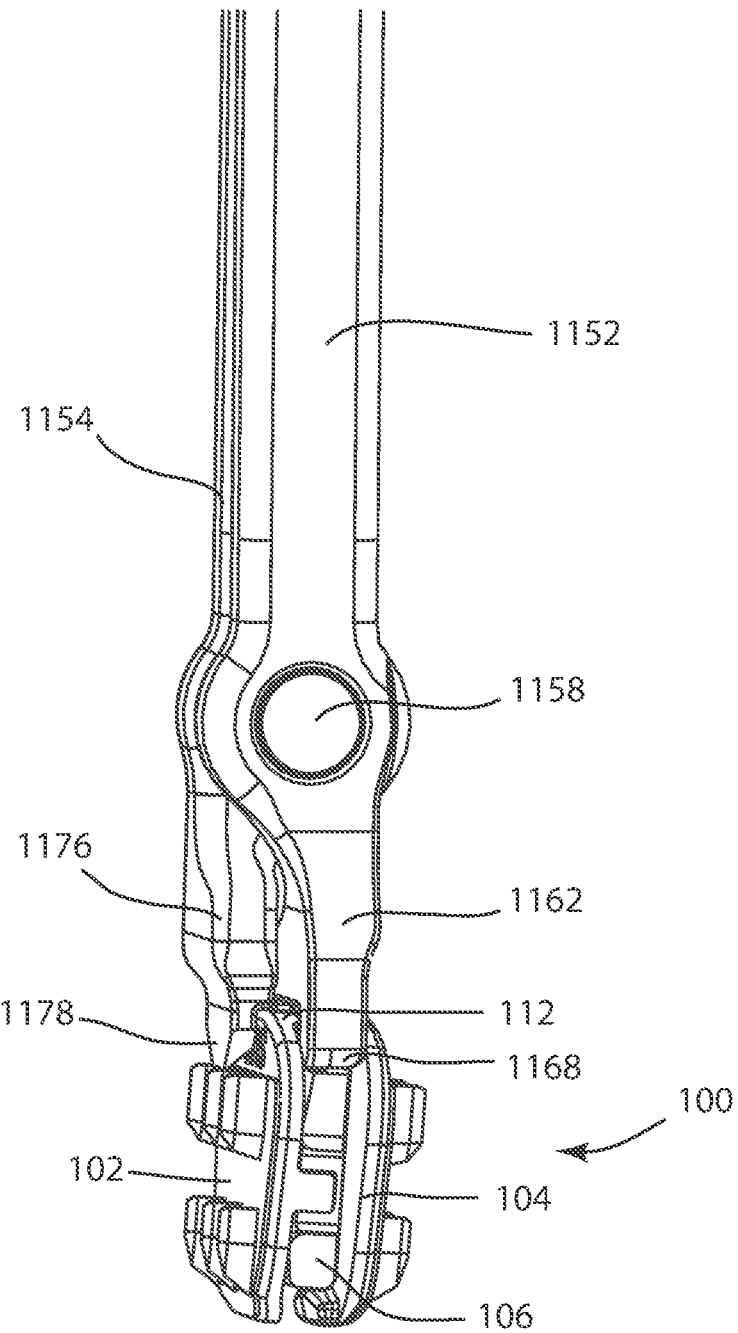
FIG. 43 is an enlarged view of a distal end of the remover tool, and implant of FIG. 42.
Figure 44:
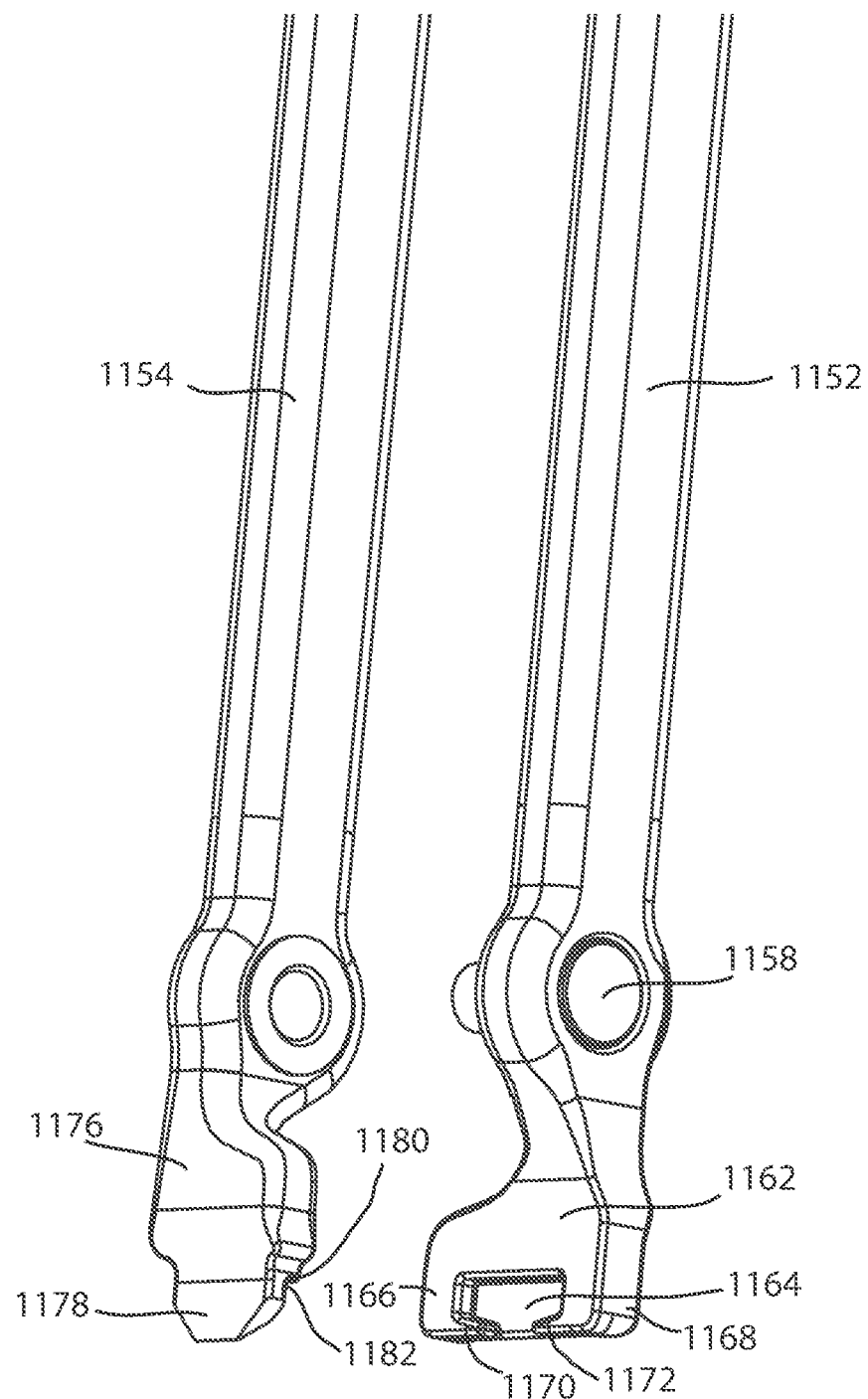
FIG. 44 is an exploded view of the distal end of the remover tool of FIG. 42.

Each implant described herein may be revised or removed in the same or a subsequent procedure. For implant revision or removal, the patient is again prepared in a neutral posture position, and the target disc level of the spine is exposed from an anterior approach. Optionally, the adjustable retainer 800 and pins, or a distractor, may be used to distract the vertebral bodies. FIG. 42 illustrates a remover tool 1150 gripping implant 100 prior to removal. FIG. 43 illustrates a distal end of remover tool 1150 gripping the implant 100, and FIG. 44 is an exploded view of the distal end of the remover tool 1150.

Referring to FIG. 42, remover tool 1150 comprises a first lever 1152 and a second lever 1154 joined at proximal ends by a ratchet mechanism 1156 and joined at distal ends by a rivet 1158. A pair of leaf springs 1160, 1161 provide resistance as the levers are ratcheted together as the implant is gripped. Referring to FIGS. 43 and 44, a distal end of first lever 1152 comprises a body 1162 with a recess 1164 at the distal most end. Two prongs 1166, 1168 enclose the recess from opposing sides such that the tips 1170, 1172 of the prongs oppose one another but do not meet. The tips 1170, 1172 are angled to interface with the dovetailed inner edges 142 of anterior retention member 140 of superior endplate 102 (seen in FIG. 3). The distal end of second lever 1154 comprises a body 1176 with a prying feature comprising a wedge or chisel point 1178. On an inside face of the body, a lip 1180 and a fillet 1182 extend across the body.

The remover tool 1150 may be opened by releasing the ratchet mechanism and moving the levers 1152, 1154 apart at their proximal ends, so that the distal ends, rotating about the rivet 1158, also move apart. The body 1162 of the first lever 1152 is engaged with the implant such that the anterior retention member 140 on the superior end plate 102 fits into the recess 1164, with the prongs 1166, 1168 around the member 140 and the prong tips 1170, 1172 mated with, or interfaced, with the dovetailed inner edges 142. The wedge point 1178 on the second lever 1154 is wedged between the superior end plate 102 and the vertebral body 2, prying them apart. Alternatively, the wedge point 1178 may be utilized before, or simultaneously, with the engagement of the body 1162 with the superior end plate 102. The remover tool is closed by ratcheting the levers together, and the bodies 1162, 1176 move toward one another, sandwiching around the anterior end 112 of the superior end plate 102. The end plate 102 is securely gripped, as the member 140 is fitted into the recess 1164, and the fillet 1182 fits around the superior anterior edge of the end plate. The superior end plate 102 is pulled anteriorly out of the intervertebral space, and the nucleus and inferior end plate are pulled out along with the superior end plate, as a result of the close overlapping juxtaposition of the implant components. As the superior end plate 102 is pulled anteriorly, its lateral motion stops 134, 135 engage the notches 300, 302 on the nucleus 106; the pocket 310 in the nucleus engages the post 180 on the inferior end plate 104; thus, the nucleus and the inferior end plate are pulled out along with the superior end plate. After removal of the implant, a replacement prosthesis may be implanted, or the prosthesis may be replaced with a fusion device or other system.

Alternatively, the remover tool may be turned 180° and used to grip the inferior end plate 104, with the anterior motion stop 170 of the end plate fitting into the recess 1164 of the first lever 1152, and with the wedge point 1178 inserted between the inferior end plate 104 and the vertebral body 4. In other alternative scenarios, if the nucleus is not present or the prosthesis has been distracted such that the components are no longer in close juxtaposition, each end plate 102, 104, may be removed individually.

The present invention may be embodied in other specific forms without departing from its spirit or essential characteristics. For example, above are described various alternative examples of artificial disc prostheses. It is appreciated that various features of the above-described examples can be mixed and matched to form a variety of other alternatives, each of which may have a different bearing surface configuration or preferred relative orientation according to the invention. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. An artificial disc replacement system, comprising:
   an implant having a leading end and a trailing end along a first axis, and two opposing lateral sides along a second axis; the implant further comprising:
   an upper plate, with an outer surface, an inner surface, and a first instrument engagement member;
   a lower plate, with an outer surface, an inner surface, and a second instrument engagement member;
   a nucleus having an upper side and a lower side, positioned between the upper and lower plates, the nucleus being adjacent the inner surface of each of the upper and lower plates;
   wherein the upper side of the nucleus comprises at least two curvate upper transition portions dividing the upper side into three flattened portions,
   wherein the lower side of the nucleus comprises at least two curvate lower transition portions dividing the lower side into three flattened portions;
   the system further comprising:
   an implant inserter comprising a gripping mechanism movable between an open position and a closed position in which the inserter is configured to securely grip the implant, the gripping mechanism having a first arm and a second arm, wherein each of the first and second arms engage the first and second instrument engagement members; and
   a remover tool comprising a first lever with a proximal end and a distal end, a second lever with a proximal end and a distal end, the levers joined at the proximal ends by a ratchet mechanism and the levers rotationally joined near the distal ends; the first lever comprising at the distal end a body with a complimentary recess adapted to engage the instrument engagement member on the lower plate; the second lever comprising at the distal end a second body with a wedge, the wedge adapted to be inserted between the upper plate and a vertebral body.

2. The system of claim 1, wherein the upper and lower plates each have bone engagement surfaces on the outer surface.

3. The system of claim 1, wherein the inner surface of the upper plate has a nucleus retention feature that engages with a complementary recess in the nucleus.

4. The system of claim 1, wherein the inner surface of the lower plate has a nucleus retention feature that engages with a complementary recess in the nucleus.

5. The system of claim 3, wherein the nucleus retention feature is a post in a generally central location on the inner surface.

6. The system of claim 4, wherein the nucleus retention feature is a plurality of flanges on opposing lateral sides of the lower plate.

7. The system of claim 6, wherein the complementary recess in the nucleus is a plurality of notches, which are engaged by the plurality of flanges.

8. The system of claim 1, wherein the at least two curvate upper transition portions are generally transverse to the at least two curvate lower transition portions.

9. An artificial disc replacement system, comprising:
   an implant having a leading end and a trailing end along a first axis, and two opposing lateral sides along a second axis; the implant further comprising:
   an upper plate, with an outer surface, an inner surface, and a first instrument engagement member;
   a lower plate, with an outer surface, an inner surface, and a second instrument engagement member;
   a nucleus having an upper side and a lower side, positioned between the upper and lower plates, the nucleus being adjacent the inner surface of each of the upper and lower plates;
   the system further comprising:
   an implant inserter comprising a gripping mechanism movable between an open position and a closed position in which the inserter is configured to securely grip the implant, the gripping mechanism having a first arm and a second arm, wherein each of the first and second arms engage the first and second instrument engagement members; and
   a remover tool comprising a first lever with a proximal end and a distal end, a second lever with a proximal end and a distal end, the levers rotationally joined between the proximal and distal ends; the first lever comprising at the distal end a first body with a complimentary recess adapted to engage the instrument engagement member on the lower plate; the second lever comprising at the distal end a second body with a wedge, the wedge adapted to be inserted between the upper plate and a vertebral body.

10. The system of claim 9, wherein the upper and lower plates each have bone engagement surfaces on the outer surface.

11. The system of claim 9, wherein the inner surface of the upper plate has a nucleus retention feature that engages with a complementary recess in the nucleus.

12. The system of claim 9, wherein the inner surface of the lower plate has a nucleus retention feature that engages with a complementary recess in the nucleus.

13. The system of claim 11, wherein the nucleus retention feature is a post in a generally central location on the inner surface.

14. The system of claim 12, wherein the nucleus retention feature is a plurality of flanges on opposing lateral sides of the lower plate.

15. The system of claim 14, wherein the complementary recess in the nucleus is a plurality of notches, which are engaged by the plurality of flanges.

16. The system of claim 9, wherein the first and second levers of the remover tool joined at the proximal ends by a ratchet mechanism.

17. The system of claim 9,
   wherein the upper side of the nucleus comprises at least two curvate upper transition portions dividing the upper side into three flattened portions,
   wherein the lower side of the nucleus comprises at least two curvate lower transition portions dividing the lower side into three flattened portions.

18. The system of claim 17, wherein the at least two curvate upper transition portions are generally transverse to the at least two curvate lower transition portions.

* * * * *